(12) United States Patent
Ikeda et al.

(10) Patent No.: US 8,569,327 B2
(45) Date of Patent: Oct. 29, 2013

(54) PHENANTHROINDOLIZIDINE DERIVATIVE AND NFκB INHIBITOR CONTAINING SAME AS ACTIVE INGREDIENT

(75) Inventors: Takashi Ikeda, Tokyo (JP); Seigo Sawada, Tokyo (JP); Takashi Yaegashi, Tokyo (JP); Takeshi Matsuzaki, Tokyo (JP); Shusuke Hashimoto, Tokyo (JP); Ryuta Yamazaki, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 111 days.

(21) Appl. No.: 13/124,554

(22) PCT Filed: Oct. 23, 2009

(86) PCT No.: PCT/JP2009/005593
§ 371 (c)(1),
(2), (4) Date: Apr. 15, 2011

(87) PCT Pub. No.: WO2010/047126
PCT Pub. Date: Apr. 29, 2010

(65) Prior Publication Data
US 2011/0201637 A1    Aug. 18, 2011

(30) Foreign Application Priority Data
Oct. 23, 2008  (JP) ................. 2008-273556

(51) Int. Cl.
*A61K 31/403* (2006.01)
*C07D 221/18* (2006.01)

(52) U.S. Cl.
USPC ............................... 514/280; 546/42

(58) Field of Classification Search
USPC ........................... 546/42; 514/280
See application file for complete search history.

(56) References Cited

U.S. PATENT DOCUMENTS

2005/0222418 A1* 10/2005 Baker et al. .......... 546/138
2006/0014772 A1  1/2006 Lee et al.

FOREIGN PATENT DOCUMENTS

| CN | 101189968 | 6/2008 |
| EP | 1 604 990 A1 | 12/2005 |
| WO | WO 01/23384 A1 | 4/2001 |
| WO | WO 03/070166 A2 | 8/2003 |
| WO | WO 03/070166 A3 | 8/2003 |

OTHER PUBLICATIONS

Wang, et al. Document No. 149:97630, (2008) retrieved from CAPLUS.*
Ganguly, et al. Document No. 138:248082, (2002) retrieved from CAPLUS.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org|wiki|Cancer.*
U.S. Appl. No. 13/125,698, filed Apr. 22, 2011, Ikeda, et al.
Ta-Hsien Chuang et al.; "Expedient synthesis and structure-activity relationships of phenanthroindolizidine and phenanthroquinolizidine alkaloids"; Org. Biomol. Chem., 2006, 4, pp. 860-867.
Cheng-Wei Yang et al.; "Anti-inflammatory effects of 7-methoxycryptopleurine and structure-activity relations of phenanthroindolizidines and phenanthroquinolizidines"; Biochemical and Biophysical Communications 2007, 354, pp. 942-948.
Gerd Dannhardt et al.; "9, 11, 12, 13, 13a, 14-Hexahydro-dibenzo [f, h] pyrrolo [1, 2-b] -isochinoline durch Diels-Alder-Reaktion"; Archiv der Pharmazie, 1977, 310, pp. 802-810.
Wenli Gao et al.; "Structural analogs of tylophora alkaloids may not be functional analogs"; Bioorganic & Medicinal Chemistry Letters, 2008, 18 pp. 704-709.

(Continued)

*Primary Examiner* — Shawquia Young
(74) *Attorney, Agent, or Firm* — Oblon, Spivak, McClelland, Maier & Neustadt, L.L.P.

(57) ABSTRACT

A novel compound having an excellent NFκB inhibitory effect is provided. Specifically disclosed is a compound represented by the following formula (1) or a salt thereof:
wherein, $R^1$ represents a hydrogen atom, a lower alkyl group, or the like;
$R^2$ represents a hydrogen atom, a lower alkyl group, a halogen atom, or the like;
$R^3$ represents a hydrogen atom, a lower alkyl group, a hydroxyl group, or a halogen atom;
$R^4$ represents a hydrogen atom or a lower alkyloxy group;
$R^5$ represents a hydrogen atom, a lower alkyloxy group, a halogen atom, a hydroxyl group, or a methylenedioxy group formed together with $R^6$ or an isopropylidenedioxy group formed together with $R^6$;
$R^6$ represents a hydrogen atom, a lower alkyloxy group, or a methylenedioxy group formed together with $R^5$ or an isopropylidenedioxy group formed together with $R^5$;
$R^7$ represents a hydrogen atom or a lower alkyl group; and
$R^8$ represents a hydrogen atom, a hydroxyl group, an amino group, a lower alkylcarbonyloxy group, or a halogen atom.

(1)

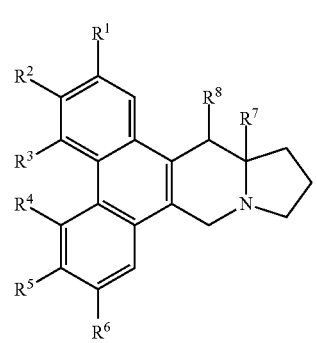

20 Claims, No Drawings

(56) References Cited

OTHER PUBLICATIONS

Timothy S. Blackwell et al.; "The Role of Nuclear Factor-κB in Cytokine Gene Regulation"; Am. J. Respir. Cell Mol. Biol., 1997, 17, pp. 3-9.

Peter J. Barnes et al.; "Nuclear Factor-κB—A Pivotal Transcription Factor in Chronic Inflammatory Diseases"; The New England Journal of Medicine, 1997, 336, pp. 1066-1071.

Gary Nabel et al.; "An inducible transcription factor activates expression of human immunodeficiency virus in T cells"; Nature, 1987, 326, pp. 711-713.

George Mosialos; "The role of Rel/Nf-κB proteins in viral oncogenesis and the regulation of viral transcription"; Seminars in Cancer Biology, 1997, 8, pp. 121-129.

Beatrice Rayet et al.; "Aberrant *rel/nfκb* genes and activity in human cancer"; Oncogene, 1999, 18, pp. 6938-6947.

HJ Kim et al.; "NF-κB and IKK as therapeutic targets in cancer"; Cell Death and Differentiation, 2006, 13, pp. 738-747.

Ryuichi Morishita et al.; "In vivo transfection of *cis* element 'decoy' against nuclear factor-κB binding site prevents myocardial infarction" Nature Medicine, 1997, vol. 3, No. 8, pp. 894-899.

Y. Mizuno et al.; "Advances in Research on Neurodegeneration"; Journal of Neural Transmission Supplementum, 1997, 49, pp. 125-134.

Daniel G. Remick.; "Applied Molecular Biology of Sepsis"; Journal of Critical Care, 1995, vol. 10, No. 4, pp. 198-212.

Gabriele E. Sonnenberg et al.; "A Novel Pathway to the Manifestations of Metabolic Syndrome"; Obesity Research, 2004, vol. 12, No. 2, pp. 180-186.

S. William Pelletier.; "Alkaloids: Chemical and Biological Perspectives"; 1987, 5, pp. 55-132.

Beat Baumgartner et al.; "An Antimicrobial Alkaloid From *Ficus septica*"; Phytochemistry, vol. 29, No. 10, 1990, pp. 3327-3330.

Zaiguo Li et al.; "Isolation, Total Synthesis and Biological Activity of Phenanthroindolizidine and Phenanthroquinolizidine Alkaloids"; Synthesis, 2001, No. 16, pp. 2365-2378.

Matthew Suffness et al.; "Miscellaneous Natural Products with Antitumor Activity"; Anticancer Agents Based on Natural Product Models, 1980, pp. 465-487.

Wenli Gao et al.; "Novel Mode of Action of Tylophorine Analogs as Antitumor Compounds"; Cancer Research, 64, 2004, pp. 678-688.

Hajime Komatsu et al.; "Phenanthroindolizidine Alkaloids as Cytotoxic Substances in a Danaid Butterfly, *Ideopsis similis*, against Human Cancer Cells"; Journal of Medicinal Chemistry, 2001, 44, pp. 1833-1836.

Wenli Gao et al.; "Structure-activity studies of phenanthroindolizidine alkaloids as potential antitumor agents"; Bioorganic & Medicinal Chemistry Letters, 17,. 2007, pp. 4338-4342.

Office Action issued on Dec. 19, 2012 in the corresponding Chinese Patent Application No. 200980141120.0 (with English Translation of summary).

* cited by examiner

PHENANTHROINDOLIZIDINE DERIVATIVE AND NFκB INHIBITOR CONTAINING SAME AS ACTIVE INGREDIENT

TECHNICAL FIELD

The present invention relates to a Nuclear Factor-κB (hereinafter, may be referred to as NFκB) inhibitor. In more detail, the present invention relates to a novel phenanthroindolizidine alkaloid compound or a salt thereof inhibiting NFκB, and a medicine containing the same.

BACKGROUND ART

NFκB exists as a dimer formed by various combinations of p50, p65/RelA, c-Rel, Rel-B, and p52, all of which are members of the NFκB family. Among them, the most well-known dimer is a heterodimer composed of a 50 kDa subunit (p50) and a 65 kDa subunit (p65).

Usually, this heterodimer is present in an inactive state in cytoplasm through binding to an inhibitor of NFκB (IκB). However, once the cells are stimulated by inflammatory cytokines, cell growth factors, and the like, IκB kinase is activated via the AKT signal transduction pathway and the like, leading to phosphorylation of IκB. The phosphorylated IκB is ubiquitinated and then decomposed by proteasome. As a result, NFκB is detached from IκB and migrate into the nucleus, where it binds to the NFκB responsive element to activate transcription of various target genes.

The target genes include many genes associated with inflammation and immune response (Non Patent Document 1), and the activation of NFκB is known to be associated with diseases such as rheumatoid arthritis, osteoarthritis, inflammatory bowel disease, atopic dermatitis, and asthma (Non Patent Document 2).

Also, various viruses such as HIV are known to activate NFκB in host cells, from which NFκB is considered to contribute to viral infection (Non Patent Documents 3 and 4).

Furthermore, recently, NFκB is known to be often constitutively activated in various tumors, and thus it is considered that NFκB may possibly be involved also in the induction of expression of various genes associated with the progression of cancer, such as carcinogenesis, metastasis, anti-apoptosis, and cell proliferation, and the resistance against anticancer agent therapy (Non Patent Documents 5 and 6).

Further, NFκB is also known to be associated with diseases such as ischemic heart disease (Non Patent Document 7), Alzheimer's disease (Non Patent Document 8), ichorrhemia (Non Patent Document 9), and metabolic syndrome (Non Patent Document 10).

Accordingly, a compound inhibiting NFκB is useful as a preventive or therapeutic agent for chronic inflammatory disease, autoimmune disease, viral disease, immune disease, novel cancer therapy, and other diseases attributable to the activation of NFκB, and such a compound is actively developed.

Meanwhile, tylophorine represented by the following formula (A) and an analog thereof are called phenanthroindolizidine alkaloid, which is a compound mainly obtained from a plant belonging to the family Asclepiadaceae (the genera *Tylophora, Vincetoxicum, Pergularia,* and *Cynanchum*) (Non Patent Document 11).

Also, some of the aforementioned plants belonging to the genus *Tylophora* are known as raw materials for anti-inflammatory drugs, antiasthma drugs, and antiameba drugs (Non Patent Document 12). Also, tylophorine is known to exhibit a potent cytotoxic activity, and a research on the synthetic method thereof is also vigorously conducted (Non Patent Document 13). Further, among the above-noted phenanthroindolizidine alkaloid, tylocrebrine represented by the following formula (B) is known to have neurotoxicity (Non Patent Document 14). Also, recently, it is known that tylophorine analogs represented by the following formulas (C) and (D) have consistently exhibited a potent cytotoxic activity in the NCI-60 tumor cell panel study, and that the mechanism of action of those tylophorine analogs is different from that of existing antitumor agents (Non Patent Document 15). Further, a compound represented by the following formula (E), which is phenanthroindolizidine alkaloid derived from the insect, is known to have a potent cytotoxic activity (Non Patent Document 16).

Furthermore, phenanthroindolizidine alkaloid is known to inhibit transcription mediated by NFκB, which is a transcription factor (Non Patent Document 15).

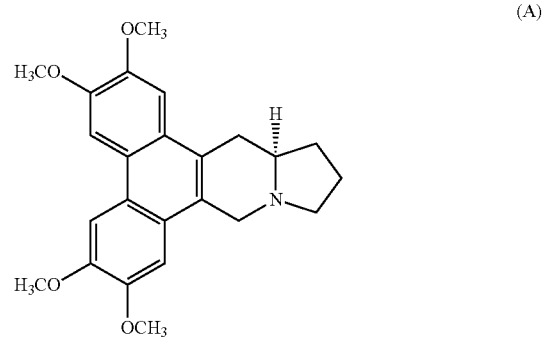

(A)

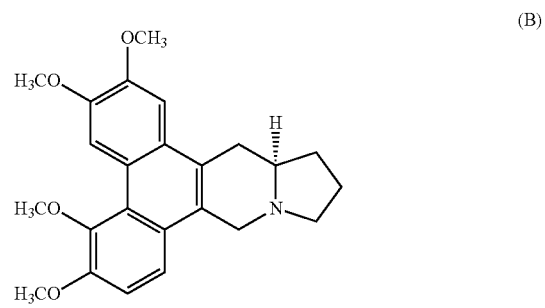

(B)

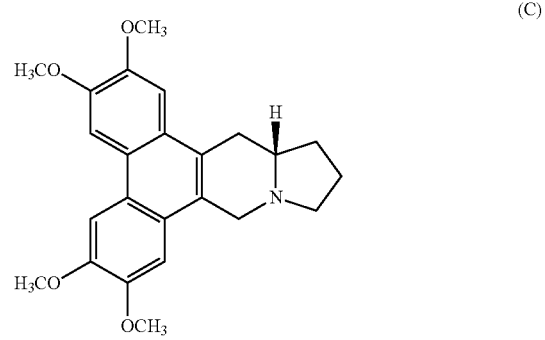

(C)

3

-continued

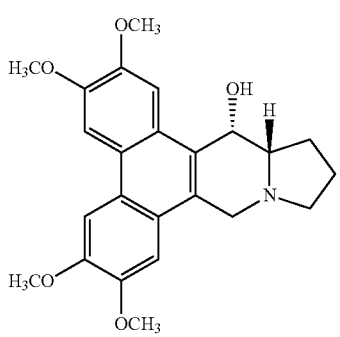

(D)

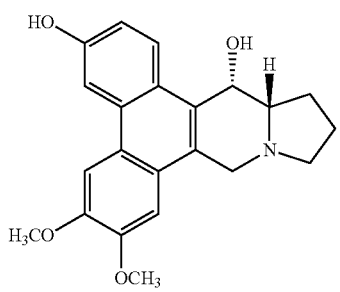

(E)

PRIOR ART DOCUMENT

Non Patent Document

[Non Patent Document 1] Am. J. Respir. Cell Mol. Biol. 1997, 17, 3-9
[Non Patent Document 2] N. Engl. J. Med. 1997, 336, 1066-1071
[Non Patent Document 3] Nature 1987, 326, 711-713
[Non Patent Document 4] Semin. Cancer Biol. 1997, 8, 121-129
[Non Patent Document 5] Oncogene 1999, 18, 6938-6947
[Non Patent Document 6] Cell Death Differ. 2006, 13, 738-747
[Non Patent Document 7] Nat. Med. 1997, 3, 894-899
[Non Patent Document 8] J. Neural Transm. Suppl. 1997, 49, 125-134
[Non Patent Document 9] J Crit. Care. 1995, 10, 198-212
[Non Patent Document 10] Obes Res. 2004, 12, 180-186.
[Non Patent Document 11] The Alkaloids, Chemistry and Biological Perspectives 1987, pp 55-132
[Non Patent Document 12] Phytochemisty 1990, 3327-3330
[Non Patent Document 13] Synthesis 2001, 2365-2378
[Non Patent Document 14] Anticancer Agents Based on Natural Product Models 1980, pp 465-487
[Non Patent Document 15] Cancer Research 2004, 678-688
[Non Patent Document 16] J. Med. Chem. 2001, 1833-1836
[Non Patent Document 17] Bioorg. Med. Chem. Lett. 2007, 4338-4342

SUMMARY OF THE INVENTION

Problem to be Solved by the Invention

Accordingly, it is an object of the present invention to provide a novel compound having an excellent NFκB inhibitory action.

4

Means of Solving the Problem

Despite the fact that phenanthroindolizidine alkaloid has a potent cytotoxic activity and an interesting mechanism of action as described above, there are very few reports on the systemic and comprehensive assessment of the biological activity, particularly the assessment of the in vivo antitumor activity, of such alkaloid (Non Patent Documents 15 and 17).

Under such a circumstance, the present inventors conducted an intensive research to achieve the aforementioned object. As a result, they have found that a compound represented by the following formula (1) or a salt thereof have excellent NFκB inhibitory action, antitumor action, and anti-inflammatory action, while having few side effects and excellent solubility, and thus is useful as a medicine such as an anticancer agent, whereby completing the present invention.

That is, the present invention provides a compound represented by the following formula (1) or a salt thereof:

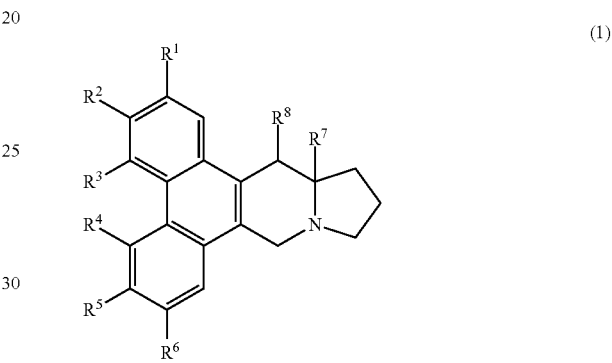

(1)

wherein, $R^1$ represents a hydrogen atom, a lower alkyl group, a hydroxyl group, a lower alkyloxy group, or a halogen atom;
$R^2$ represents a hydrogen atom, a lower alkyl group, a halogen atom, a lower alkylcarbonyloxy group optionally having a substituent, a heterocyclic carbonyloxy group, a lower alkyloxycarbonyloxy group, a lower alkyl-substituted aminocarbonyloxy group, an amino group optionally having a substituent, a lower alkyl-substituted amino group optionally having a substituent, a heterocyclic group, a lower alkyloxycarbonylamino group optionally having a substituent, a lower alkylcarbonylamino group, a formamide group, or a hydroxy lower alkyl group;
$R^3$ represents a hydrogen atom, a lower alkyl group, a hydroxyl group, or a halogen atom;
$R^4$ represents a hydrogen atom or a lower alkyloxy group;
$R^5$ represents a hydrogen atom, a lower alkyloxy group, a halogen atom, a hydroxyl group, or a methylenedioxy group formed together with $R^6$ or an isopropylidenedioxy group formed together with $R^6$;
$R^6$ represents a hydrogen atom, a lower alkyloxy group, or a methylenedioxy group formed together with $R^5$ or an isopropylidenedioxy group formed together with $R^5$;
$R^7$ represents a hydrogen atom or a lower alkyl group; and
$R^8$ represents a hydrogen atom, a hydroxyl group, an amino group, a lower alkylcarbonyloxy group, or a halogen atom.

The present invention also provides a medicine containing a compound represented by the above formula (1) or a salt thereof as an active ingredient.

The present invention also provides a pharmaceutical composition containing a compound represented by the above formula (1) or a salt thereof and a pharmaceutically acceptable carrier.

The present invention further provides use of a compound represented by the above formula (1) or a salt thereof for the production of a medicine.

The present invention further provides a method for preventing or treating diseases associated with accelerated NFκB activity or cancer characterized by administering a compound represented by the above formula (1) or a salt thereof.

Effects of the Invention

The compound represented by the formula (1) or the salt thereof of the present invention has excellent NFκB inhibitory action, antitumor action, and anti-inflammatory action, while having few side effects and excellent solubility, thus it is useful as a medicine, an NFκB inhibitor, a preventive or therapeutic agent for diseases associated with accelerated NFκB activity including proliferation or metastasis of cancer, resistance against anticancer agents, inflammatory disease (rheumatoid arthritis, osteoarthritis, atopic dermatitis, bronchial asthma, psoriasis, inflammatory bowel disease, and the like), cardiovascular disease (ischemic disease, vascular restenosis after percutaneous transluminal coronary angioplasty (PTCA), and the like), pulmonary fibrosis, diabetes, autoimmune disease, viral disease, Alzheimer's disease, ichorrhemia, metabolic syndrome, and the like.

MODE FOR CARRYING OUT THE INVENTION

In the general formula (1), examples of $R^1$ include a hydrogen atom, a lower alkyl group, a hydroxyl group, a lower alkyloxy group, and a halogen atom. Among these, a hydrogen atom, a hydroxyl group, or the following functional groups are particularly preferable.

Examples of the lower alkyl group include an alkyl group with a carbon number of 1 to 6. Specific examples thereof include a methyl group, an ethyl group, a propyl group, a butyl group, a pentyl group, and a hexyl group. Among these, a methyl group is particularly preferable.

Examples of the lower alkyloxy group include an alkyloxy group with a carbon number of 1 to 6. Specific examples thereof include a methoxy group, an ethoxy group, a propoxy group, a butoxy group, a pentyloxy group, and a hexyloxy group. Among these, a methoxy group is particularly preferable.

Also, examples of the halogen atom include a chlorine atom, a bromine atom, a fluorine atom, and an iodine atom. Among these, a chlorine atom and a fluorine atom are particularly preferable.

That is, in the general formula (1), as $R^1$, a hydrogen atom, a methyl group, a hydroxyl group, a methoxy group, a chlorine atom, or a fluorine atom is particularly preferable.

In the general formula (1), examples of $R^2$ include a hydrogen atom, a lower alkyl group, a halogen atom, a lower alkylcarbonyloxy group optionally having a substituent, a heterocyclic carbonyloxy group, a lower alkyloxycarbonyloxy group, a lower alkyl-substituted aminocarbonyloxy group, an amino group optionally having a substituent, a lower alkyl-substituted amino group optionally having a substituent, a heterocyclic group, a lower alkyloxycarbonylamino group optionally having a substituent, a lower alkylcarbonylamino group, a formamide group, and a hydroxy lower alkyl group. Among these, a hydrogen atom, a formamide group, or the following functional groups are particularly preferable.

Examples of the lower alkyl group include an alkyl group with a carbon number of 1 to 6. Specific examples thereof include a methyl group, an ethyl group, a propyl group, a butyl group, a pentyl group, and a hexyl group. Among these, an ethyl group is particularly preferable.

Also, examples of the halogen atom include a chlorine atom, a bromine atom, a fluorine atom, and an iodine atom. Among these, a fluorine atom is particularly preferable.

Examples of the lower alkylcarbonyloxy group optionally having a substituent include an alkylcarbonyloxy group with a carbon number of 1 to 6 optionally having a substituent. Particularly, an acetoxy group, a propionyloxy group, an isobutyryloxy group, a valeroyloxy group, a 3-methoxycarbonylpropionyloxy group, a pivaloyloxy group, a butyryloxy group, and a 6-carbo[(12aS,13S)-13-hydroxy-6,7-dimethoxy-9,10,11,12,12a,13-hexahydro-9a-aza-cyclopenta[b]triphenylene-3-yloxy]heptanoyloxy group are preferable.

Also, as the heterocyclic carbonyloxy group, a nicotinoyloxy group, an isonicotinoyloxy group, a piperidinopiperidinylcarbonyloxy group, a 2-thiophenecarbonyloxy group, a 3-thiophenecarbonyloxy group, a 2-furoyloxy group, and a 3-furoyloxy group are particularly preferable.

Examples of the lower alkyloxycarbonyloxy group include an alkyloxycarbonyloxy group with a carbon number of 1 to 6. Specific examples thereof include a methoxycarbonyloxy group, a 2-propynyloxycarbonyloxy group, an ethoxycarbonyloxy group, a propionyloxycarbonyloxy group, a vinyloxylcarbonyloxy group, a propenyloxycarbonyloxy group, and an ethinyloxycarbonyloxy group. Among these, a methoxycarbonyloxy group, a 2-propynyloxycarbonyloxy group, and an ethoxycarbonyloxy group are particularly preferable.

Examples of the lower alkyl-substituted aminocarbonyloxy group include an alkyl-substituted aminocarbonyloxy group with a carbon number of 1 to 6. Specific examples thereof include a dimethylaminocarbonyloxy group and a diethylaminocarbonyloxy group. Among these, a dimethylaminocarbonyloxy group is particularly preferable.

Also, as the amino group optionally having a substituent, an amino group and a methanesulfonamide group are particularly preferable.

Examples of the lower alkyl-substituted amino group optionally having a substituent include an alkyl-substituted amino group with a carbon number of 1 to 6 optionally having a substituent and an alkyl-substituted amino group with a carbon number of 1 to 6 optionally having an aromatic group. Specific examples thereof include a diphenylmethylamino group, an ethylamino group, and a methylamino group. Among these, a diphenylmethylamino group and an ethylamino group are preferable.

Examples of the heterocyclic group include a pyrrolidinyl group and a piperidino group. Among these, a pyrrolidinyl group is particularly preferable.

Examples of the lower alkyloxycarbonylamino group optionally having a substituent include an alkyloxycarbonylamino group with a carbon number of 1 to 6 optionally having a substituent and an alkyloxycarbonylamino group with a carbon number of 1 to 6 optionally having an aromatic group. Specific examples thereof include an isobutyloxycarbonylamino group, a benzyloxycarbonylamino group, a methoxycarbonylamino group, and an ethoxycarbonylamino group. Among these, an isobutyloxycarbonylamino group, a benzyloxycarbonylamino group, and a methoxycarbonylamino group are particularly preferable.

Examples of the lower alkylcarbonylamino group include an alkylcarbonylamino group with a carbon number of 1 to 6. Specific examples thereof include an acetamide group, a propionylamide group, a butyrylamide group, a trifluoroacetamide group, and a benzamide group. Among these, an acetamide group, a trifluoroacetamide group, and a benzamide group are preferable.

Examples of the hydroxy lower alkyl group include a hydroxyalkyl group with a carbon number of 1 to 6. Specific examples thereof include a hydroxymethyl group and a hydroxyethyl group. Among these, a hydroxymethyl group is particularly preferable.

That is, in the general formula (1), as $R^2$, a hydrogen atom, an ethyl group, a fluorine atom, an acetoxy group, a propionyloxy group, an isobutyryloxy group, a valeroyloxy group, a 3-methoxycarbonylpropionyloxy group, a pivaloyloxy group, a butyryloxy group, a 6-carbo[(12aS,13S)-13-hydroxy-6,7-dimethoxy-9,10,11,12,12a,13-hexahydro-9a-azacyclopenta[b]triphenylene-3-yloxy]heptanoyloxy group, a nicotinoyloxy group, an isonicotinoyloxy group, a piperidinopiperidinylcarbonyloxy group, a 2-thiophenecarbonyloxy group, a 3-thiophenecarbonyloxy group, a 2-furoyloxy group, a 3-furoyloxy group, a methoxycarbonyloxy group, a 2-propynyloxycarbonyloxy group, an ethoxycarbonyloxy group, a dimethylaminocarbonyloxy group, an amino group, a methanesulfonamide group, a diphenylmethylamino group, an ethylamino group, a pyrrolidinyl group, an isobutyloxycarbonylamino group, a benzyloxycarbonylamino group, a methoxycarbonylamino group, an acetamide group, a trifluoroacetamide group, a benzamide group, a formamide group, or a hydroxymethyl group is particularly preferable.

In the general formula (1), examples of $R^3$ include a hydrogen atom, a lower alkyl group, a hydroxyl group, and a halogen atom. Among these, a hydrogen atom, a hydroxyl group, or the following functional groups are particularly preferable.

Examples of the lower alkyl group include an alkyl group with a carbon number of 1 to 6. Specific examples thereof include a methyl group, an ethyl group, a propyl group, a butyl group, a pentyl group, and a hexyl group. Among these, a methyl group is particularly preferable.

Examples of the halogen atom include a fluorine atom, a chlorine atom, a bromine atom, and an iodine atom. Among these, a fluorine atom and a chlorine atom are particularly preferable.

That is, in the general formula (1), as $R^3$, a hydrogen atom, a methyl group, a hydroxyl group, a fluorine atom, or a chlorine atom is particularly preferable.

In the general formula (1), examples of $R^4$ include a hydrogen atom and a lower alkyloxy group. Among these, a hydrogen atom or the following functional groups are particularly preferable.

Examples of the lower alkyloxy group include an alkyloxy group with a carbon number of 1 to 6. Specific examples thereof include a methoxy group, an ethoxyl group, a propoxy group, a butoxy group, a pentyloxy group, and a hexyloxy group. Among these, a methoxy group is particularly preferable.

That is, in the general formula (1), as $R^4$, a hydrogen atom or a methoxy group is particularly preferable.

In the general formula (1), examples of $R^5$ include a hydrogen atom, a lower alkyloxy group, a halogen atom, a hydroxyl group, a methylenedioxy group formed together with $R^6$, and an isopropylidenedioxy group formed together with $R^6$, and among these, a hydrogen atom, a hydroxyl group, a methylenedioxy group formed together with $R^6$, and an isopropylidenedioxy group formed together with $R^6$, or the following functional groups are particularly preferable.

Examples of the lower alkyloxy group include an alkyloxy group with a carbon number of 1 to 6. Specific examples thereof include a methoxy group, an ethoxygroup, a propoxy group, a butoxy group, a pentyloxy group, and a hexyloxy group, of which a methoxy group and an ethoxy group are particularly preferable.

Also, examples of the halogen atom include a chlorine atom, a bromine atom, a fluorine atom, and an iodine atom, and among these, a fluorine atom is particularly preferable.

That is, in the general formula (1), as $R^5$, a hydrogen atom, a methoxy group, an ethoxy group, a fluorine atom, a hydroxyl group, a methylenedioxy group formed together with $R^6$, or an isopropylidenedioxy group formed together with $R^6$ is particularly preferable.

In the general formula (1), examples of $R^6$ include a hydrogen atom, a lower alkyloxy group, a methylenedioxy group formed together with $R^5$, or an isopropylidenedioxy group formed together with $R^5$, and among these, a hydrogen atom, a methylenedioxy group formed together with $R^5$, an isopropylidenedioxy group formed together with $R^5$, or the following functional groups are particularly preferable.

Examples of the lower alkyloxy group include an alkyloxy group with a carbon number of 1 to 6. Specific examples thereof include a methoxy group, an ethoxy group, a propoxy group, a butoxy group, a pentyloxy group, and a hexyloxy group, and among these, a methoxy group and an ethoxy group are particularly preferable.

That is, in the general formula (1), as $R^6$, a hydrogen atom, a methoxy group, an ethoxy group, a methylenedioxy group formed together with $R^5$, or an isopropylidenedioxy group formed together with $R^5$ is particularly preferable.

In the general formula (1), examples of $R^7$ include a hydrogen atom and a lower alkyl group, and among these, a hydrogen atom or the following functional groups are particularly preferable.

Examples of the lower alkyl group include an alkyl group with a carbon number of 1 to 6. Specific examples thereof include a methyl group, an ethyl group, a propyl group, a butyl group, a pentyl group, and a hexyl group, and among these, a methyl group is particularly preferable.

That is, in the general formula (1), as $R^7$, a hydrogen atom or a methyl group is particularly preferable.

In the general formula (1), examples of $R^8$ include a hydrogen atom, a hydroxyl group, an amino group, a lower alkylcarbonyloxy group, and a halogen atom. Particularly, a hydrogen atom, a hydroxyl group, an amino group, or the following functional groups are particularly preferable.

Examples of the lower alkylcarbonyloxy group include an alkylcarbonyloxy group with a carbon number of 1 to 6. Specific examples thereof include an acetoxy group, a propionyloxy group, and a butyryloxy group, and among these, an acetoxy group is particularly preferable.

Also, examples of the halogen atom include a chlorine atom, a bromine atom, a fluorine atom, and an iodine atom, and among these, a fluorine atom is particularly preferable.

That is, in the general formula (1), as $R^8$, a hydrogen atom, a hydroxyl group, an amino group, an acetoxy group, or a fluorine atom is particularly preferable.

A compound of the general formula (1), wherein $R^1$ is a hydrogen atom; $R^2$ is an acetoxy group or a 3-methoxycarbonylpropionyloxy group; $R^3$ is a hydrogen atom; $R^4$ is a hydrogen atom; $R^5$ is a methoxy group; $R^6$ is a methoxy group; $R^7$ is a hydrogen atom; and $R^8$ is a hydrogen atom or a hydroxyl group is more preferable.

In the present invention, the compound of the above formula (1) has two stereocenters (carbon atoms at which $R^7$ and $R^8$ are substituted). Because these stereocenters could take either an R configuration or an S configuration, four kinds of stereoisomers are possible. However, all of such stereoisomers and a mixture of various combinations of stereoisomers are encompassed by the scope of the present invention.

Examples of the isomer include (a configuration in which $R^7$=S, $R^8$=S), (a configuration in which $R^7$=R, $R^8$=R), (a configuration in which $R^7$=S, $R^8$=R), and (a configuration in which $R^7$=R, $R^8$=S); and among these, (a configuration in which $R^7$=S, $R^8$=S) is particularly preferable since a compound having such a configuration strongly inhibits NFκB without inducing unfavorable side effects.

In the present invention, a compound of the following formula (2) or a pharmaceutically acceptable salt thereof is more preferable since such a compound or salt strongly inhibits NFκB without inducing unfavorable side effects.

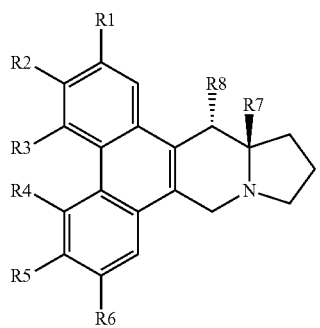

(2)

wherein, $R^1$, $R^2$, $R^3$, $R^4$, $R^5$, $R^6$, $R^7$, and $R^8$ are the same as above.

In the present invention, a compound of the following formula (3) or a pharmaceutically acceptable salt thereof is further preferable since such a compound or salt strongly inhibits NFκB without inducing unfavorable side effects.

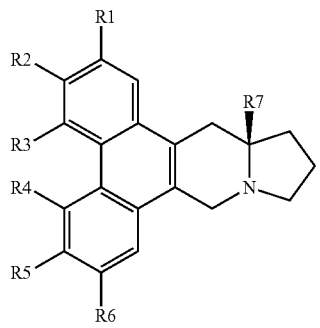

(3)

wherein, $R^1$, $R^2$, $R^3$, $R^4$, $R^5$, $R^6$, and $R^7$ are the same as above.

In the present invention, specific examples of a particularly preferable compound or a salt thereof include one selected from the group consisting of (12aS,13S)-6,7-dimethoxy-9,10,11,12,12a,13-hexahydro-9a-aza-cyclopenta[b]triphenylene-13-ol;

(12aR,13R)-6,7-dimethoxy-9,10,11,12,12a,13-hexahydro-9a-aza-cyclopenta[b]triphenylene-13-ol;

(12aS,13S)-3-ethyl-6,7-dimethoxy-9,10,11,12,12a,13-hexahydro-9a-aza-cyclopenta[b]triphenylene-13-ol;

(12aR,13R)-3-ethyl-6,7-dimethoxy-9,10,11,12,12a,13-hexahydro-9a-aza-cyclopenta[b]triphenylene-13-ol;

(12aS,13S)-3-fluoro-6,7-dimethoxy-9,10,11,12,12a,13-hexahydro-9a-aza-cyclopenta[b]triphenylene-13-ol;

(12aR,13R)-3-fluoro-6,7-dimethoxy-9,10,11,12,12a,13-hexahydro-9a-aza-cyclopenta[b]triphenylene-13-ol;

acetic acid(12aS,13S)-13-hydroxy-6,7-dimethoxy-9,10,11,12,12a,13-hexahydro-9a-aza-cyclopenta[b]triphenylene-3-yl ester;

acetic acid(12aS,13S)-3-acetoxy-6,7-dimethoxy-9,10,11,12,12a,13-hexahydro-9a-aza-cyclopenta[b]triphenylene-13-yl ester;

isobutyric acid(12aS,13S)-13-hydroxy-6,7-dimethoxy-9,10,11,12,12a,13-hexahydro-9a-aza-cyclopenta[b]triphenylene-3-yl ester;

2,2-dimethyl-propionic acid(12aS,13S)-13-hydroxy-6,7-dimethoxy-9,10,11,12,12a,13-hexahydro-9a-aza-cyclopenta[b]triphenylene-3-yl ester;

nicotinic acid (12aS,13S)-13-hydroxy-6,7-dimethoxy-9,10,11,12,12a,13-hexahydro-9a-aza-cyclopenta[b]triphenylene-3-yl ester;

isonicotinic acid(12aS,13S)-13-hydroxy-6,7-dimethoxy-9,10,11,12,12a,13-hexahydro-9a-aza-cyclopenta[b]triphenylene-3-yl ester;

[1,4']bipiperidinyl-1'-carboxylic acid(12aS,13S)-13-hydroxy-6,7-dimethoxy-9,10,11,12,12a,13-hexahydro-9a-aza-cyclopenta[b]triphenylene-3-yl ester;

acetic acid(S)-13-fluoro-6,7-dimethoxy-9,10,11,12,12a,13-hexahydro-9a-aza-cyclopenta[b]triphenylene-3-yl ester;

propionic acid(12aS,13S)-13-hydroxy-6,7-dimethoxy-9,10,11,12,12a,13-hexahydro-9a-aza-cyclopenta[b]triphenylene-3-yl ester;

succinic acid(12aS,13S)-13-hydroxy-6,7-dimethoxy-9,10,11,12,12a,13-hexahydro-9a-aza-cyclopenta[b]triphenylene-3-yl ester methyl ester;

carbonic acid(12aS,13S)-13-hydroxy-6,7-dimethoxy-9,10,11,12,12a,13-hexahydro-9a-aza-cyclopenta[b]triphenylene-3-yl ester methyl ester;

((12aS,13S)-13-hydroxy-6,7-dimethoxy-9,10,11,12,12a,13-hexahydro-9a-aza-cyclopenta[b]triphenylene-3-yl)-carbamic acid isobutyl ester;

thiophene-2-carboxylic acid(12aS,13S)-13-hydroxy-6,7-dimethoxy-9,10,11,12,12a,13-hexahydro-9a-aza-cyclopenta[b]triphenylene-3-yl ester;

furan-2-carboxylic acid(12aS,13S)-13-hydroxy-6,7-dimethoxy-9,10,11,12,12a,13-hexahydro-9a-aza-cyclopenta[b]triphenylene-3-yl ester;

dimethyl-carbamic acid(12aS,13S)-13-hydroxy-6,7-dimethoxy-9,10,11,12,12a,13-hexahydro-9a-aza-cyclopenta[b]triphenylene-3-yl ester;

furan-3-carboxylic acid(12aS,13S)-13-hydroxy-6,7-dimethoxy-9,10,11,12,12a,13-hexahydro-9a-aza-cyclopenta[b]triphenylene-3-yl ester;

thiophene-3-carboxylic acid(12aS,13S)-13-hydroxy-6,7-dimethoxy-9,10,11,12,12a,13-hexahydro-9a-aza-cyclopenta[b]triphenylene-3-yl ester;

octanedionic acid(9S,12S)-13-hydroxy-6,7-dimethoxy-9,10,11,12,12a,13-hexahydro-9a-aza-cyclopenta[b]triphenylene-3-yl ester(12aS,13S)-13-hydroxy-6,7-dimethoxy-9,10,11,12,12a,13-hexahydro-9a-aza-cyclopenta[b]triphenylene-3-yl ester;

(12aS,13S)-3-amino-6,7-dimethoxy-9,10,11,12,12a,13-hexahydro-9a-aza-cyclopenta[b]triphenylene-13-ol;

((12aS,13S)-13-hydroxy-6,7-dimethoxy-9,10,11,12,12a,13-hexahydro-9a-aza-cyclopenta[b]triphenylene-3-yl)-carbamic acid benzyl ester;

carbonic acid(12aS,13S)-13-hydroxy-6,7-dimethoxy-9,10,11,12,12a,13-hexahydro-9a-aza-cyclopenta[b]triphenylene-3-yl ester-propyn-2-yl ester;
carbonic acid ethyl ester(12aS,13S)-13-hydroxy-6,7-dimethoxy-9,10,11,12,12a,13-hexahydro-9a-aza-cyclopenta[b]triphenylene-3-yl ester;
(12aS,13S)-6,7-dimethoxy-9,10,11,12,12a,13-hexahydro-9a-aza-cyclopenta[b]triphenylene-2,13-diol;
(12aS,13S)-6,7-dimethoxy-9,10,11,12,12a,13-hexahydro-9a-aza-cyclopenta[b]triphenylene-4,13-diol;
(S)-3-fluoro-6,7-dimethoxy-9,10,11,12,12a,13-hexahydro-9a-aza-cyclopenta[b]triphenylene;
(S)-6,7-dimethoxy-9,10,11,12,12a,13-hexahydro-9a-aza-cyclopenta[b]triphenylene;
(S)-6,7-dimethoxy-9,10,11,12,12a,13-hexahydro-9a-aza-cyclopenta[b]triphenylene-2-ol;
acetic acid(S)-6,7-dimethoxy-9,10,11,12,12a,13-hexahydro-9a-aza-cyclopenta[b]triphenylene-3-yl ester;
2,2-dimethyl-propionic acid(S)-6,7-dimethoxy-9,10,11,12,12a,13-hexahydro-9a-aza-cyclopenta[b]triphenylene-3-yl ester;
succinic acid(S)-6,7-dimethoxy-9,10,11,12,12a,13-hexahydro-9a-aza-cyclopenta[b]triphenylene-3-yl ester methyl ester;
carbonic acid(S)-6,7-dimethoxy-9,10,11,12,12a,13-hexahydro-9a-aza-cyclopenta[b]triphenylene-3-yl ester methyl ester;
furan-2-carboxylic acid(S)-6,7-dimethoxy-9,10,11,12,12a,13-hexahydro-9a-aza-cyclopenta[b]triphenylene-3-yl ester;
nicotinic acid(S)-6,7-dimethoxy-9,10,11,12,12a,13-hexahydro-9a-aza-cyclopenta[b]triphenylene-3-yl ester;
(S)-6,7-dimethoxy-9,10,11,12,12a,13-hexahydro-9a-aza-cyclopenta[b]triphenylene-4-ol;
(S)-3-ethyl-6,7-dimethoxy-9,10,11,12,12a,13-hexahydro-9a-aza-cyclopenta[b]triphenylene;
((S)-6,7-dimethoxy-9,10,11,12,12a,13-hexahydro-9a-aza-cyclopenta[b]triphenylene-3-yl)-carbamic acid isobutyl ester;
pentanoic acid(S)-6,7-dimethoxy-9,10,11,12,12a,13-hexahydro-9a-aza-cyclopenta[b]triphenylene-3-yl ester;
butyric acid(S)-6,7-dimethoxy-9,10,11,12,12a,13-hexahydro-9a-aza-cyclopenta[b]triphenylene-3-yl ester;
propionic acid(S)-6,7-dimethoxy-9,10,11,12,12a,13-hexahydro-9a-aza-cyclopenta[b]triphenylene-3-yl ester;
(S)-3-amino-6,7-dimethoxy-9,10,11,12,12a,13-hexahydro-9a-aza-cyclopenta[b]triphenylene;
N-((S)-6,7-dimethoxy-9,10,11,12,12a,13-hexahydro-9a-aza-cyclopenta[b]triphenylene-3-yl)-acetamide;
(S)-6,7-dimethoxy-3-pyrrolidine-9,10,11,12,12a,13-hexahydro-9a-aza-cyclopenta[b]triphenylene;
benzhydryl-((S)-6,7-dimethoxy-3-pyrrolidine-9,10,11,12,12a,13-hexahydro-9a-aza-cyclopenta[b]triphenylene-3-yl)-amine;
((S)-6,7-dimethoxy-9,10,11,12,12a,13-hexahydro-9a-aza-cyclopenta[b]triphenylene-3-yl)-methanol;
N-((S)-6,7-dimethoxy-9,10,11,12,12a,13-hexahydro-9a-aza-cyclopenta[b]triphenylene-3-yl)-2,2,2-trifluoro-acetamide;
((S)-6,7-dimethoxy-9,10,11,12,12a,13-hexahydro-9a-aza-cyclopenta[b]triphenylene-3-yl)-ethyl-amine;
((S)-6,7-dimethoxy-9,10,11,12,12a,13-hexahydro-9a-aza-cyclopenta[b]triphenylene-3-yl)-carbamic acid methyl ester;
N-((S)-6,7-dimethoxy-9,10,11,12,12a,13-hexahydro-9a-aza-cyclopenta[b]triphenylene-3-yl)-methanesulfonamide;
N-((S)-6,7-dimethoxy-9,10,11,12,12a,13-hexahydro-9a-aza-cyclopenta[b]triphenylene-3-yl)-formamide; and
N-((S)-6,7-dimethoxy-9,10,11,12,12a,13-hexahydro-9a-aza-cyclopenta[b]triphenylene-3-yl)-benzamide.

In the present invention, a salt of a compound represented by the general formulas (1) to (3) may be a pharmaceutically acceptable salt. Examples thereof include an inorganic acid salt such as hydrochloride, sulfate, phosphate, hydrobromate, hydroiodide, nitrate, pyrosulfate, and metaphosphate; an organic acid salt such as citrate, oxalate, benzoate, acetate, trifluoroacetate, propionate, succinate, fumarate, lactate, maleate, tartrate, glutarate, citrate, sulfonate (for example, methanesulfonate, p-toluenesulfonate, and naphthalenesulfonate); and a metal salt such as a lithium salt, a sodium salt, a potassium salt, a magnesium salt, and a calcium salt.

The compound of the present invention can be produced, for example, in accordance with the following reaction formula (a compound in which $R^7$=H, $R^8$=OH (compound j) and a compound in which $R^7$=$R^8$=H (compound l) in the general formula (1) or (2) will be shown as examples).

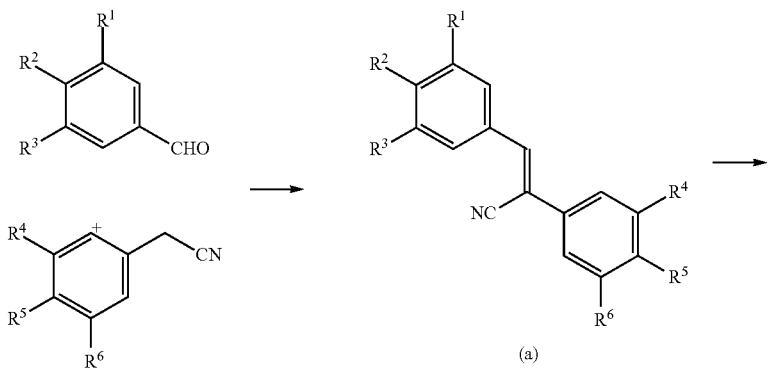

(a)

-continued
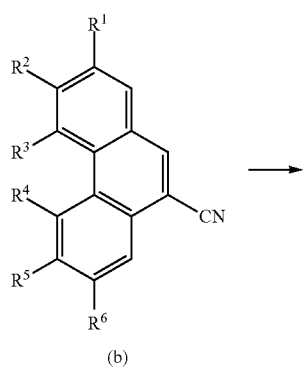
(b)
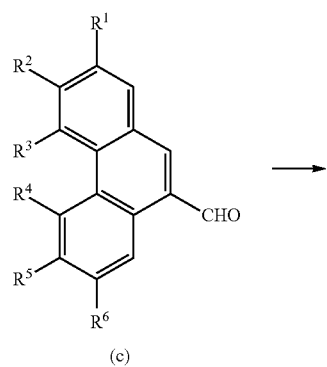
(c)
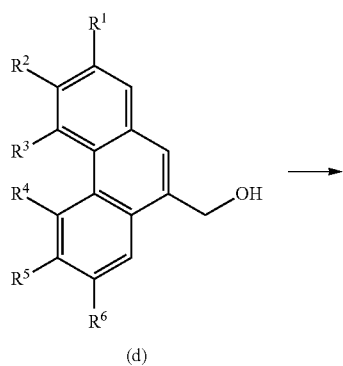
(d)
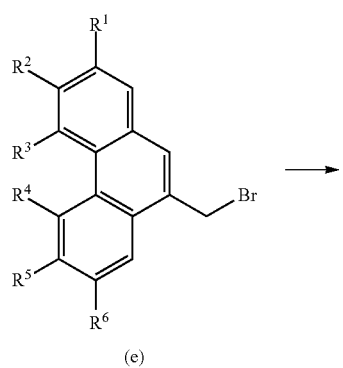
(e)
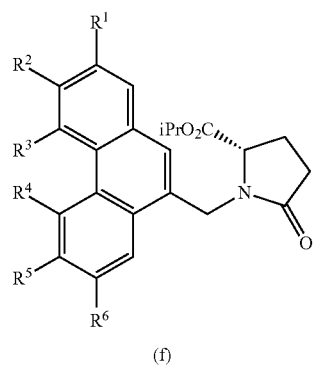
(f)
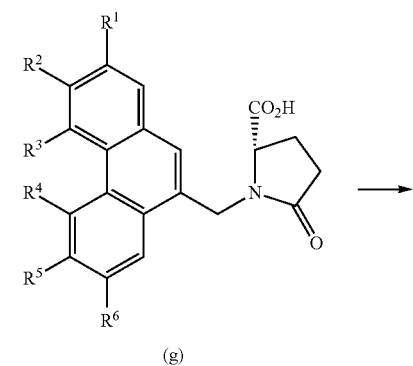
(g)
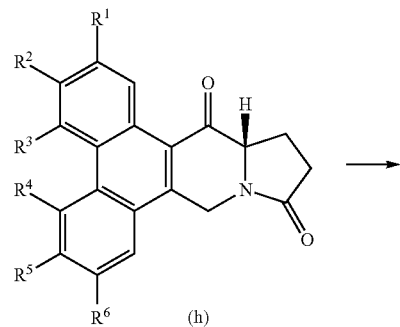
(h)

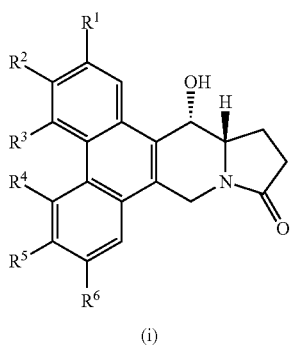

(i)

-continued

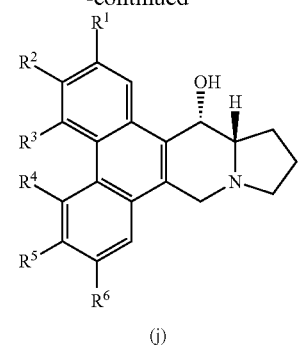

(j)

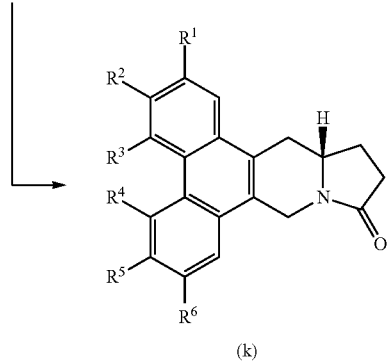

(k)

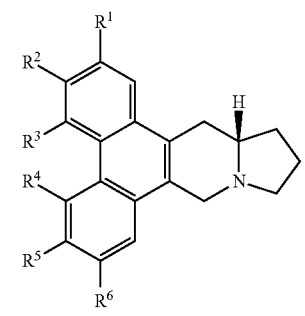

(l)

wherein, the groups $R^1$ to $R^6$ represent the same groups as mentioned above, or if there is a functional group involved in the reaction, such a group may be appropriately protected.

That is, benzaldehyde was reacted with benzyl cyanide to give a compound (a), which was cyclized to give a compound (b). Subsequently, a cyano group was reduced, whereby aldehyde (c) was obtained. Then, a carbonyl group was reduced to give alcohol (d), which was brominated to give a compound (e). Subsequently, the compound (e) was reacted with glutamic acid ester, followed by cyclization, whereby a compound (f) was obtained. The compound (f) was hydrolyzed to give a compound (g), from which a compound (h) was obtained through intramolecular acylation. And then, a carbonyl group was reduced to give a compound (i), followed by reduction of lactam, whereby phenanthroindolizidine (j) having a hydroxyl group at $R^8$ was obtained. The hydroxyl group at $R^8$ of the compound (i) was reductively removed to give (k), followed by reduction of lactam, whereby phenanthroindolizidine (l) having a hydrogen atom at $R^8$ was obtained.

The reaction of benzaldehyde with benzyl cyanide is preferably carried out in alcohol in the presence of a base. At this point, specific examples of the base include sodium methoxide and sodium ethoxide.

The cyclization of the compound (a) is preferably carried out by photoirradiation in the presence of iodine and propylene oxide. Also, a cyclization reaction involving treatment with vanadium (V) or thallium (III) may be employed.

The reduction of the compound (b) is preferably carried out by reacting diisobutylaluminum hydride. Also, the reduction of the compound (c) is preferably carried out by reacting sodium borohydride.

The bromination of the compound (d) is preferably carried out by reacting phosphorous tribromide in the presence of triethylamine. Also, the bromination may be carried out by allowing carbon tetrabromide to act in the presence of triphenylphosphine.

The amination-lactamization of the compound (e) with L-glutamic acid diisopropyl ester is preferably carried out in a solvent such as dimethylformamide in the presence of a base such as potassium carbonate, and allowing an acid such as acetic acid to act on the resulting aminated product in alcohol such as methanol. At this point, when D-glutamic acid diisopropyl ester is used, a corresponding enantiomer is obtained.

The hydrolysis of the compound (f) is preferably carried out using a base in a solvent such as methanol. At this point, specific examples of the base include potassium hydroxide and sodium hydroxide.

The intramolecular Friedel-Crafts reaction of the compound (g) is preferably carried out in a solvent such as methylene chloride by converting the compound (g) to acid chloride by oxalyl chloride within a system, followed by treatment with a Lewis acid. At this point, specific examples of the Lewis acid include tin chloride and aluminum chloride.

The reduction of the compound (h) is preferably carried out using a reducing agent such as sodium borohydride and lithium tri-secondary butyl borohydride. For stereoselective reduction, the reduction is preferably carried out using a reducing agent such as lithium tri-secondary butyl borohydride.

The reduction of the lactam of the compound (i) is preferably carried out using a reducing agent such as borane and lithium aluminum hydride.

The reduction of the hydroxyl group of the compound (i) is preferably carried out by a combination of an acid and a reducing agent. As the acid, trifluoroacetic acid, a boron trifluoride-diethyl ether complex, and the like are preferable. As the reducing agent, triethylsilane is preferable.

The reduction of the lactam of the compound (k) is preferably carried out using a reducing agent such as borane and lithium aluminum hydride.

As will be shown in the following Examples, a compound represented by the formula (1) or a salt thereof have excellent NFκB inhibitory action and antitumor action.

Accordingly, the compound or the salt thereof of the present invention is useful as a medicine, an NFκB inhibitor, an anticancer agent (proliferation or metastasis of cancer), and a preventive or therapeutic agent for diseases associated with accelerated NFκB activity including resistance against anticancer agents, inflammatory disease (rheumatoid arthritis, osteoarthritis, atopic dermatitis, bronchial asthma, psoriasis, inflammatory bowel disease, and the like), cardiovascular disease (ischemic disease, vascular restenosis after percutaneous transluminal coronary angioplasty (PTCA), and the like), pulmonary fibrosis, diabetes, autoimmune disease, viral disease, Alzheimer's disease, sepsis, metabolic syndrome, and the like.

In the present invention, no particular limitation is imposed on the "NFκB inhibitor" as long as it has an inhibitory action on NFκB. More specifically, an NFκB inhibitor exhibits an $IC_{50}$ value of the inhibitory action on NFκB of preferably 2000 ng/mL or less, more preferably 500 ng/mL or less, and particular preferably 100 ng/mL or less, as measured by the method of Example 1 described below.

Also, an NFκB inhibitor exhibits an $IC_{50}$ value of the inhibitory action on cancer proliferation of preferably 2000 ng/mL or less, more preferably 500 ng/mL or less, and particular preferably 100 ng/mL or less, as measured by the method of Example 2 described below.

When a compound represented by the formula (1) or a salt thereof is used as a medicine, one kind of the compound or the salt thereof may be used alone or plural kinds thereof may be used in combination. Further, a compound represented by the formula (1) or a salt thereof may also be used in combination with other therapeutically advantageous compounds, and the mechanism of action of these therapeutically advantageous compounds may be the same as or different from that of the compound of the present invention.

When the compound of the present invention is used as a medicine, it can be administered in any dosage form. Examples thereof include an orally administered agent such as a tablet, a capsule, a granule, a sugar-coated tablet, a pill, a fine granule, powder, a dust formulation, a sustained-release formulation, a suspension, an emulsion, syrup, an emulsified formulation, a lyophilized preparation, a liquid, and an elixir; and a parenterally administered agent including an injection such as an intravenous injection, an intramuscular injection, a subcutaneous injection, or a drip infusion, an external agent such as an endermic liniment or a patch, a suppository, an infusion solution, a percutaneous agent, a transmucosal agent, a nasal agent, an inhalant, a bolus, and the like.

Further, when the compound is used as a medicine, a preparation can be produced by an ordinary method, in which the compound represented by the formula (1) or the salt thereof of the present invention may be employed alone or in combination with a pharmaceutically acceptable carrier. Examples of the pharmaceutically acceptable carrier include an excipient, a binder, a disintegrant, a surfactant, a lubricant, a fluidity promoter, a corrigent, a colorant, a flavor, a diluent, a disinfecting agent, an osmotic pressure adjuster, a pH adjuster, an emulsifying agent, a preservative, a stabilizer, an absorption aid, an antioxidant, an ultraviolet absorber, a humectant, a viscosity enhancer, a glazing agent, an activity enhancer, an anti-inflammatory agent, a tonicity agent, a soothing agent, and a flavoring agent.

Examples of the binder include starch, dextrin, powder gum arabic, gelatin, hydroxypropyl starch, methylcellulose, sodium carboxymethylcellulose, hydroxypropylcellulose, crystalline cellulose, ethylcellulose, polyvinylpyrrolidone, and macrogol.

Examples of the disintegrant include starch, hydroxypropyl starch, sodium carboxymethylcellulose, calcium carboxymethylcellulose, carboxymethylcellulose, low-substituted hydroxypropylcellulose.

Examples of the surfactant include sodium lauryl sulfate, soy lecithin, sucrose fatty acid ester, and polysorbate 80.

Examples of the lubricant include talc, waxes, hydrogenated vegetable oil, sucrose fatty acid ester, magnesium stearate, calcium stearate, aluminum stearate, and polyethylene glycol.

Examples of the fluidity promoter include light anhydrous silicic acid, dried aluminum hydroxide gel, synthesized aluminum silicate, and magnesium silicate.

Examples of the diluent include distilled water for injection, physiological saline, an aqueous solution of glucose, olive oil, sesame oil, peanut oil, soybean oil, corn oil, propylene glycol, and polyethylene glycol.

Further, when a medicine containing a compound represented by the formula (1) or a salt thereof as an active ingredient is systemically administered, a preferable dosage form is an injection or an orally administered agent, and as the injection, an intravenous injection is particularly preferable. In that case, the medicine can be administered via other injection routes such as a subcutaneous, intramuscular, or intraperitoneal injection, or the medicine may be administered transmucosally or percutaneously using a penetrant such as bile salt or fuchsin acid, or other surfactants. The aforementioned administration of a pharmaceutical composition may be given locally or in the form of an ointment, a paste, a gel, and the like.

Also, the NFκB inhibitor of the present invention may be used not only as the pharmaceutical products as described above but also as foods, drinks, and the like. In that case, the phenanthroindolizidine alkaloid compound or the salt thereof of the present invention may be contained in foods and drinks as-is or together with various nutritional components. The foods and drinks thus obtained can be utilized as food products for health use or foodstuff which are useful for improvement, prevention, etc. of proliferation or metastasis of cancer, resistance against anticancer agents, inflammatory disease (rheumatoid arthritis, osteoarthritis, atopic dermatitis, bronchial asthma, psoriasis, inflammatory bowel disease, and the like), cardiovascular disease (ischemic disease, vascular restenosis after percutaneous transluminal coronary angioplasty (PTCA), and the like), pulmonary fibrosis, diabetes, autoimmune disease, viral disease, Alzheimer's disease, sepsis, metabolic syndrome, and the like. These foods and drinks or a container thereof may display that the foods and drinks have the aforementioned effects. Specifically, when the NFκB inhibitor of the present invention is added to foods and drinks, they may be shaped into a form suitable for ingestion, for example, a granule, a grain, a tablet, a capsule, and a paste, by ordinary means using additives permitted for use in foods and drinks, if desired. Also, the NFκB inhibitor of the present invention may be added to various food products, for example, a processed meat product such as ham and sausage, a processed seafood product such as cooked minced fish or fish sausage, bread, confectionary, butter, dry milk, and fermented foods and drinks, or the NFκB inhibitor of the present invention may also be added to drinks such as water, fruit juice, milk, a soft drink, and a tea drink. It is to be noted that the foods and drinks also include feed for the animal.

Further, as the foods and drinks, fermented milk products such as fermented milk, fermented bacterial drinks, fermented soymilk, fermented fruit juice, and fermented vegetable juice containing the phenanthroindolizidine alkaloid compound or a salt thereof as an active ingredient are preferably employed. These fermented milk foods and drinks may be produced by an ordinary method. For example, fermented milk is obtained by inoculating lactic acid bacteria and bifidobacteria into a sterilized milk medium and culturing them, and subjecting the resulting product to homogenization treatment to give a fermented milk base. Subsequently, a separately-prepared syrup solution and the phenanthroindolizidine alkaloid compound or a salt thereof are added and mixed, and the resulting product is homogenized using a homogenizer and the like, and a flavor is further added to prepare the final product. The fermented milk foods and drinks obtained in this manner may also be provided in the form of, for example, any of plain type, soft type, fruit-flavored type, solid, and liquid products.

No strict limitation is imposed on the dosage amount of the phenanthroindolizidine alkaloid compound or a salt thereof, which is the active ingredient of the NFκB inhibitor of the present invention. Because the effects achieved vary depending on various usage patterns involving the subject of administration, indication, and the like, the dosage amount is desirably determined for each case, and a dosage amount of the phenanthroindolizidine alkaloid compound or a salt thereof is preferably 1 mg to 10 g, more preferably 10 mg to 1 g, per day.

Furthermore, the NFκB inhibitor of the present invention can be applied to all kinds of mammals including human.

EXAMPLES

The present invention will be further described in detail with Examples as described below, but, the present invention is not limited thereto.

The phenanthroindolizidine alkaloid of the present invention was synthesized in accordance with a reaction pathway including the following steps 1 to 10. When any of the substituents represented by R needed to be protected for the reaction to proceed, a suitable protecting group was used to carry out the reaction.

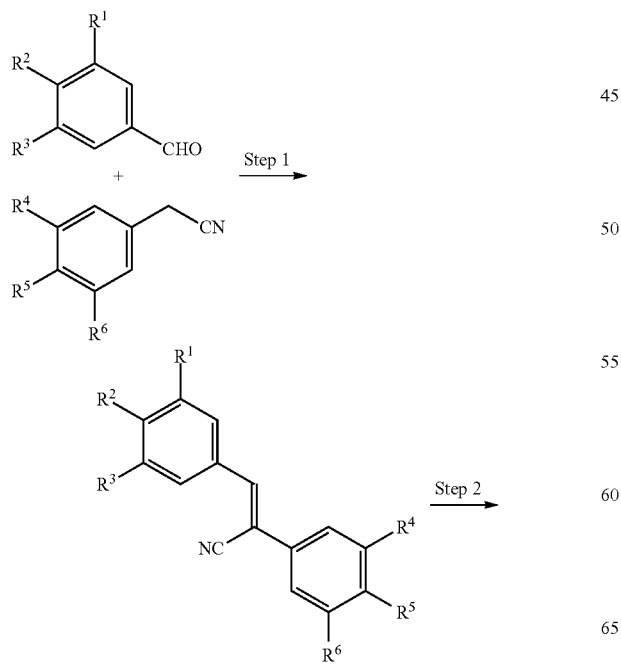

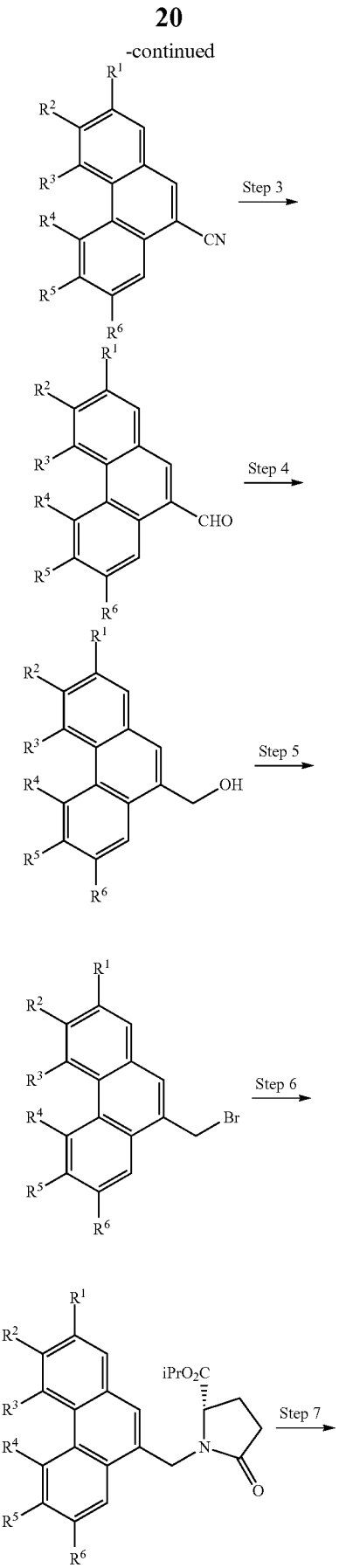

-continued

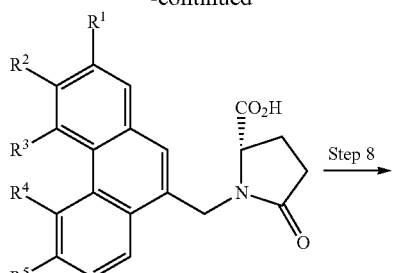

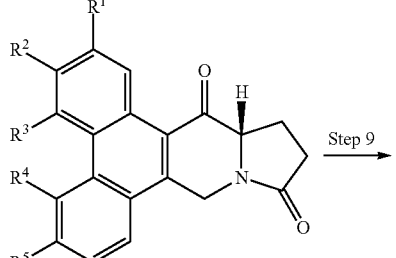

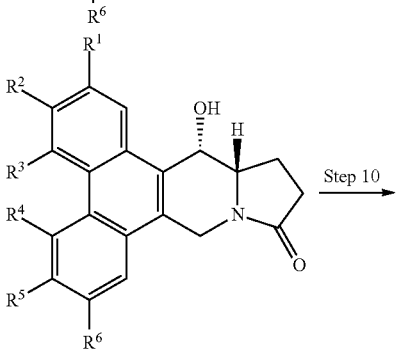

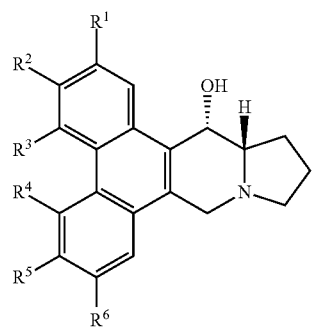

Synthesis Example 1

A compound having the following groups at $R^1$ to $R^6$ was synthesized. The operations of the steps 1 to 10 will be described below.

TABLE 1

| Compound 1 | | | | | |
|---|---|---|---|---|---|
| $R^1$ | $R^2$ | $R^3$ | $R^4$ | $R^5$ | $R^6$ |
| H | H | H | H | $OCH_3$ | $OCH_3$ |

Step 1: Synthesis of Stilbene

In a round-bottom flask, 380 mg (5.64 mmol, 0.1 eq.) of sodium ethoxide was added to a suspension of 10.0 g (56.43 mmol) of 3,4-dimethoxybenzyl cyanide and 5.99 g (56.43 mmol, 1.0 eq.) of benzaldehyde in 150 mL of ethanol under an argon atmosphere at room temperature while stirring, and the resulting mixture was heated to reflux (the oil bath temperature: 85° C.). After three hours, the disappearance of the raw materials was confirmed, and the resulting reaction liquid was cooled on ice to precipitate a solid. The solid was then collected by suction filtration using a Büchner funnel and a filtering flask, which was then washed with 100 mL of methanol twice. The solid was dried under reduced pressure at 60° C. to give 13.70 g (92%) of light yellow powder.

$^1$HNMR (400 MHz, $CDCl_3$) δ 3.94 (s, 3H), 3.97 (s, 3H), 6.93 (d, J=8.8 Hz, 1H), 7.16 (d, J=2.4 Hz, 1H), 7.27 (dd, J=8.8, 2.4 Hz, 1H), 7.39-7.49 (m, 3H), 7.44 (s, 1H), 7.83-7.92 (m, 2H)

Step 2: Synthesis of Phenanthrene by Photoinduced Electrocyclic Reaction

In a photoreaction container, argon was infused into a solution of 5.5 g (20.75 mmol) of stilbene in 7 L of acetonitrile at room temperature while stirring. After 10 minutes, 5.27 g (20.75 mmol, 1.0 eq.) of iodine and 58 mL (830 mmol, 40 eq.) of propylene oxide were added, followed by irradiation of light at room temperature while stirring. After 72 hours of irradiation, the disappearance of the raw materials was confirmed, and the resulting reaction liquid was concentrated. The residual product was dissolved in 500 mL of chloroform, followed by washing with 1 L of saturated sodium thiosulfate and 500 mL of brine. The organic layer was dried over magnesium sulfate, and then the solvent was distilled under reduced pressure to give a solid. The solid was collected by suction filtration using a Büchner funnel and a filtering flask, which was then washed with 50 mL of methanol twice. The solid was dried under reduced pressure at 60° C. to give 4.70 g (86.0%) of light brown powder.

$^1$HNMR (400 MHz, $CDCl_3$) δ 4.11 (s, 3H), 4.14 (s, 3H), 7.56-7.66 (m, 2H), 7.72-7.82 (m, 1H), 7.92 (d, J=8.3 Hz, 1H), 8.01 (s, 1H), 8.17 (s, 1H), 8.54 (d, J=8.3 Hz, 1H)

Step 3: Reduction of a Cyano Group by Diisobutylaluminum Hydride

In a round-bottom flask, a 14.8 mL of 1.0 M solution of diisobutylaluminum hydride in methylene chloride (14.8 mmol, 1.3 eq.) was added dropwise to a solution of 3.0 g (11.41 mmol) of cyanide in 200 mL of methylene chloride under an argon atmosphere while stirring with cooling on ice. During the dropwise addition, the mixture turned into a yellow suspension. The suspension was stirred for one hour on ice, and then for three hours at room temperature, after then the disappearance of the raw materials was confirmed. The resulting reaction liquid was cooled on ice, to which 100 mL of 10% hydrochloric acid was slowly added. The reaction liquid turned into a suspension, which was dissolved in a solution of chloroform-methanol=4:1. The organic layer was separated and the aqueous layer was extracted with a solution of chloroform-methanol=4:1. The organic layer was combined and the resulting mixture was dried over magnesium sulfate. The solvent was then distilled under reduced pressure to give 2.38 g (78%) of a yellow solid.

$^1$HNMR (400 MHz, $CDCl_3$) δ 4.12 (s, 3H), 4.14 (s, 3H), 7.60-7.66 (m, 1H), 7.76-7.84 (m, 1H), 8.03 (s, 1H), 8.02-8.07 (m, 1H), 8.19 (s, 1H), 8.54-8.57 (m, 1H), 8.98 (s, 1H), 10.33 (s, 1H)

Step 4: Reduction of Aldehyde by Sodium Borohydride

In a recovery flask, 344 mg (9.10 mmol, 1.1 eq.) of sodium borohydride was added to a suspension of 2.2 g (8.27 mmol) of aldehyde in 40 mL of methanol and 80 mL of 1,4-dioxane under an argon atmosphere while stirring with cooling on ice. After one hour, the disappearance of the raw materials was confirmed, and 100 mL of brine was added to the resulting reaction liquid. Further, a solution of chloroform-methanol=4:1 was added to give a complete solution. And then, the organic layer was separated and the aqueous layer was extracted with a solution of chloroform-methanol=4:1. The organic layer was combined and the resulting mixture was dried over magnesium sulfate. The solvent was then removed under reduced pressure to give 2.04 g (92%) of a light brown solid.

$^1$HNMR (400 MHz, CDCl$_3$) δ 4.07 (s, 3H), 4.13 (s, 3H), 5.14-5.16 (m, 2H), 7.52-7.65 (m, 2H), 7.57 (s, 1H), 7.69 (s, 1H), 7.87 (dJ=7.8 Hz, 1H), 8.05 (s, 1H), 8.51 (d, J=8.3 Hz, 1H)

Step 5: Bromination of a Hydroxyl Group

In a round-bottom flask, 521 μL (3.73 mmol, 1 eq.) of triethylamine was added to a suspension of 1 g (3.73 mmol) of alcohol in 50 mL of chloroform under an argon atmosphere. Subsequently, while stirring with cooling on ice, 356 μL (3.73 mmol, 1.0 eq.) of phosphorus tribromide was slowly added dropwise. After two hours, the disappearance of the raw materials was confirmed, and 30 mL of water was slowly added dropwise to precipitate a solid. After 30 minutes, the solid was dissolved in a solution of chloroform-methanol=4:1. And then, the organic layer was separated and the aqueous layer was extracted with a solution of chloroform-methanol=4:1. The organic layer was collected and dried over magnesium sulfate. After that, the solvent was removed under reduced pressure to give 1.09 g (88%) of the reaction product.

$^1$HNMR (400 MHz, CDCl$_3$) δ 4.11 (s, 3H), 4.14 (s, 3H), 5.00 (s, 2H), 7.50-7.56 (m, 1H), 7.56 (s, 1H), 7.60-7.66 (m, 1H), 7.77 (s, 1H), 7.82-7.86 (m, 1H), 8.06 (s, 1H), 8.49-8.52 (m, 1H)

Step 6: Introduction of a Glutamic Acid Unit

In a round-bottom flask, 550 mg (2.38 mmol, 1.25 eq.) of L-glutamic acid diisopropyl ester and 657 mg (4.75 mmol, 2.5 eq.) of potassium carbonate were added to a solution of 543 mg (1.9 mmol) of bromide in 20 mL of DMF and 20 mL of benzene, followed by stirring while heating at 80° C. After two hours, the disappearance of the raw materials was confirmed. The resulting reaction liquid was cooled on ice, and 100 mL of water and 100 mL of brine were added thereto. Further, 200 mL of ethyl acetate was added, and then the organic layer was washed with each of a saturated aqueous solution of sodium bicarbonate and brine. The resulting solution was dried over magnesium sulfate, and the solvent was removed under reduced pressure to give an aminated crude product.

A solution of the crude product obtained in this manner in 16 mL of methanol, 16 mL of 1,4-dioxane, and 8 mL of acetic acid was stirred at 45° C. After 16 hours, the disappearance of the raw materials was confirmed. The resulting reaction liquid was allowed to stand to cool, and 100 mL of brine was added thereto. Further, a saturated aqueous solution of sodium bicarbonate was gradually added to make the aqueous layer weakly basic. The aqueous layer was extracted with ethyl acetate, and the organic layer was dried over magnesium sulfate. The solvent was then removed under reduced pressure. The residual product was purified by silica gel column chromatography (hexane:ethyl acetate=1:1) to give 532 mg (77%) of a white solid.

$^1$HNMR (400 MHz, CDCl$_3$) δ 1.19 (d, J=6.4 Hz, 3H), 1.20 (d, J=6.4 Hz, 3H), 1.92-2.01 (m, 1H), 2.06-2.16 (m, 1H), 2.34-2.44 (m, 1H), 2.54-2.66 (m, 1H), 3.70-3.75 (m, 1H), 4.05 (s, 3H), 4.12 (s, 3H), 4.35 (d, J=14.6 Hz, 1H), 5.02 (heptet, J=6.4 Hz, 1H), 5.64 (d, J=14.6 Hz, 1H), 7.50 (s, 1H), 7.52-7.56 (m, 1H), 7.61-7.66 (m, 1H), 7.64 (s, 1H), 8.03 (s, 1H), 8.50-8.53 (m, 1H)

90.8% ee (HPLC condition A), $[α]_D^{24}$+98.34 (c=0.10, CH$_3$Cl)

Also, by a similar operation to the above, synthesis of an enantiomer can be achieved by using D-glutamic acid diisopropyl ester instead of L-glutamic acid diisopropyl ester. The reactions were carried out similarly to steps 7 to 10 in the subsequent steps to give an enantiomer of the compound 1 (compound 2). The following enantiomers were also produced similarly.

yield: 83%, 97.5% ee, $[α]_D^{26}$−98.17 (c=0.11, CH$_3$Cl)

Step 7: Hydrolysis of pyroglutamic acid ester

In a round-bottom flask, an aqueous solution of potassium hydroxide (KOH: 303 mg (5.4 mmol, 4.5 eq.), H$_2$O: 5 mL) was added to a solution of 500 mg (1.2 mmol) of ester in 10 mL of methanol and 20 mL of 1,4-dioxane at room temperature while stirring. After one hour, the disappearance of the raw materials was confirmed, and the solvent was removed under reduced pressure. To the remaining aqueous solution, 1 mol/L hydrochloric acid was added little by little while stirring with cooling on ice to achieve a pH of 2 to 3 to precipitate a white solid. The white solid was collected by suction filtration using a Büchner funnel and a filtering flask, which was washed with 50 mL of purified water twice. The receiver was replaced by another filtering flask, and the solid was dissolved in a solution of chloroform-methanol=4:1. The resulting solution was transferred to a separatory funnel, and the organic layer was separated and dried over magnesium sulfate. Thereafter, the solvent was distilled under reduced pressure to give 416 mg (92%) of a light pink to white solid.

$^1$HNMR (400 MHz, DMSO-d$_6$) δ 1.82-1.94 (m, 1H), 2.08-2.20 (m, 1H), 2.26-2.48 (m, 2H), 3.64-3.72 (m, 1H), 3.87 (s, 3H), 4.01 (s, 3H), 4.28 (d, J=14.9 Hz, 1H), 5.42 (d, J=14.9 Hz, 1H), 7.52-7.57 (m, 3H), 7.60-7.65 (m, 1H), 7.88-7.91 (m, 1H), 8.19 (s, 1H), 8.73-8.76 (m, 1H)

Step 8: Intramolecular Friedel-Crafts Acylation Reaction

In a round-bottle flask, 210 μL (2.4 mmol, 2.0 eq.) of oxalyl chloride and one drop of DMF were added to a suspension of 416 mg (1.2 mmol) of carboxylic acid in 200 mL of methylene chloride under an argon atmosphere at room temperature while stirring. After one hour, a 3.6 mL of 1.0 M solution of tin chloride (IV) in methylene chloride (3.6 mmol, 3.0 eq.) was slowly added. Upon completion of the dropwise addition, the resulting mixture was heated to reflux. After four hours, the disappearance of the raw materials was confirmed. The resulting reaction mixture (a brown to orange suspension) was cooled on ice, and 50 mL of 1 mol/L hydrochloric acid was added, followed by stirring for 30 minutes. A solution of chloroform-methanol=4:1 was added to turn the mixture into a solution, and subsequently the organic layer was washed with each of 1 mol/L hydrochloric acid, a saturated aqueous solution of sodium bicarbonate, and brine. The organic layer was dried over magnesium sulfate and the solvent was removed under reduced pressure. The residual product was purified by silica gel column chromatography (chloroform-methanol=50:1) to give 274 mg (63%) of a yellow solid.

99.9% ee (HPLC condition B)

$^1$HNMR (400 MHz, CDCl$_3$) δ 2.25-2.68 (m, 4H), 4.10 (s, 3H), 4.17 (s, 3H), 4.44-4.48 (m, 1H), 4.73 (d, J=18.2 Hz, 1H), 5.77 (d, J=18.2 Hz, 1H), 7.36 (s, 1H), 7.63-7.70 (m, 2H), 8.03 (s, 1H), 8.52-8.56 (m, 1H), 9.35-9.41 (m, 1H)

<Enantiomer>
yield: 60%, 99.9% ee

Step 9: Diastereoselective Reduction of Ketone by Lithium Tri-Secondary Butyl Borohydride In a round-bottom flask, a 1.35 ml of 1.0 M solution of lithium tri-secondary butyl borohydride in THF (1.35 mmol, 2.0 eq.) was added to a solution of 240 mg (0.67 mmol) of ketone in 20 mL of THF at −78° C. under an argon atmosphere. After one hour, the disappearance of the raw materials was confirmed, and saturated aqueous ammonium chloride was then added to the resulting reaction liquid to quench the reaction. The aqueous layer was extracted with ethyl acetate, and the organic layer was dried over anhydrous magnesium sulfate. The solvent was removed under reduced pressure, and the residual product was purified by silica gel column chromatography (chloroform-methanol=100:1) to give 145 mg (63%) of a yellow solid.

99.9% ee (HPLC condition A), $[\alpha]_D^{22}$+163.20 (c=0.10, CH$_3$Cl)

$^1$HNMR (400 MHz, CDCl$_3$) δ 2.30-2.41 (m, 1H), 2.52-2.66 (m, 1H), 2.72-2.82 (m, 1H), 3.97-4.02 (m, 1H), 4.00 (s, 3H), 4.13 (s, 3H), 4.55 (d, J=17.8 Hz, 1H), 5.32 (d, J=2.2 Hz, 1H), 5.43 (d, J=17.8 Hz, 1H), 7.16 (s, 1H), 7.62-7.70 (m, 1H), 8.02 (s, 2H), 8.27-8.32 (m, 1H), 8.54-8.60 (m, 1H)

<Enantiomer>
yield: 78%, 97.6% ee, $[\alpha]_D^{24}$−153.09 (c=0.03, CH$_3$Cl)

Step 10: Reduction of Lactam

In a round-bottom flask, a 1.6 mL of 1.0 M solution of BH$_3$.THF in THF (1.6 mmol, 4.0 eq.) was added dropwise to a solution of 135 mg (0.38 mmol) of lactam in 30 mL of THF under an argon atmosphere while stirring with cooling on ice. After two hours, the disappearance of the raw materials was confirmed. The resulting reaction liquid was cooled on ice, and 242 μL (1.6 mmol, 4.0 eq.) of N,N,N',N'-tetramethylethylenediamine was added thereto while stirring. After 16 hours, the disappearance of an amine-borane complex was confirmed, and the solvent was removed under reduced pressure. And then, the residual product was purified by silica gel column chromatography (chloroform-methanol=50:1) to give 88 mg (74%) of a white solid.

yield: 49%, 99.9% ee (HPLC condition B), $[\alpha]_D^{28}$+115.11 (c=0.10, CH$_3$Cl)

$^1$HNMR (400 MHz, DMSO-d$_6$) δ 1.76-1.90 (m, 3H), 2.14-2.24 (m, 1H), 2.32-2.48 (m, 2H), 3.28-3.36 (m, 1H), 3.51 (d, J=15.4 Hz, 1H), 3.94 (s, 3H), 4.01 (s, 3H), 4.61 (d, J=15.4 Hz, 1H), 4.66-4.67 (m, 1H), 4.96-5.01 (m, 1H), 7.26 (s, 1H), 7.55-7.60 (m, 2H), 8.16 (s, 1H), 8.26-8.32 (m, 1H), 8.72-8.76 (m, 1H)

The yield and the specific optical rotation of compound 2 are shown below.

<Enantiomer> (Compound 2)
yield: 60%, 99.7% ee, $[\alpha]_D^{28}$−114.13 (c=0.05, CH$_3$Cl)

Under similar reaction conditions, derivatives in which the phenanthrene rings have different substituents can be synthesized by changing the starting material. Each of the derivatives will be described hereinbelow, but in a case in which the same reaction operation was repeated, the description of the operation was omitted.

Synthesis Example 2

A compound having the following groups at R$^1$ to R$^6$ was synthesized. The operations and the yield of each operation are shown below.

TABLE 2

| Compound 29 | | | | | |
|---|---|---|---|---|---|
| R$^1$ | R$^2$ | R$^3$ | R$^4$ | R$^5$ | R$^6$ |
| OH | H | H | H | OCH$_3$ | OCH$_3$ |

Step 1
yield: quant
$^1$HNMR (400 MHz, CDCl$_3$) δ: 3.93 (3H, s), 3.96 (3H, s), 5.14 (2H, s), 6.92 (1H, dd, J=8.5 Hz), 7.01-7.07 (1H, m), 7.14 (1H, d, J=2.4 Hz), 7.26 (1H, dd, J=2.4, 8.5 Hz), 7.31-7.48 (8H, m), 7.53-7.56 (1H, m)

Step 2
yield: 88.7%
A mixture of regioisomers with respect to a benzyloxy group on the aromatic ring (an isomer ratio of 66:34) was isolated.

Step 3
yield: 97.6%
A mixture of regioisomers with respect to a benzyloxy group on the aromatic ring (an isomer ratio of 66:34) was isolated.

Step 4
yield: quant
A mixture of regioisomers with respect to a benzyloxy group on the aromatic ring (an isomer ratio of 66:34) was isolated.

Step 5
yield: 87.8%
A mixture of regioisomers with respect to a benzyloxy group on the aromatic ring (an isomer ratio of 66:34) was isolated.

Step 6
yield: 38.9%, $[\alpha]_D^{29}$+96.37 (c=0.18, CHCl$_3$)
$^1$HNMR (400 MHz, CDCl$_3$) δ: 1.18 (6H, d, J=6.2 Hz), 1.90-1.99 (1H, m), 2.07-2.17 (1H, m), 2.34-2.44 (1H, m), 2.54-2.65 (1H, m), 3.74 (1H, dd, J=3.7, 9.3 Hz), 4.03 (3H, s), 4.10 (3H, s), 4.32 (1H, d, J=14.4 Hz), 5.01 (1H, heptet, J=6.2 Hz), 5.21 (2H, s), 5.62 (1H, d, J=14.4 Hz), 7.25 (1H, d, J=2.7 Hz), 7.35 (1H, dd, J=2.7, 9.0 Hz), 7.34-7.38 (1H, m), 7.39-7.45 (3H, m), 7.48-7.53 (2H, m), 7.60 (1H, s), 7.93 (1H, s), 8.43 (1H, d, J=9.0 Hz)

Step 7
yield: 72.2%
$^1$HNMR (400 MHz, DMSO-d$_6$) δ: 1.84-1.95 (1H, m), 2.02-2.20 (1H, m), 2.27-2.44 (2H, m), 3.62-3.70 (1H, m), 3.85 (3H, s), 3.99 (3H, s), 4.24 (1H, d, J=14.6 Hz), 5.41 (1H, d, J=14.6 Hz), 5.24 (2H, s), 7.31 (1H, dd, J=2.4, 9.0 Hz), 7.32-7.38 (1H, m), 7.39-7.55 (7H, m), 8.09 (1H, s), 8.66 (1H, d, J=9.0 Hz)

Step 8
yield: 75.9%, $[\alpha]_D^{29}$+97.90 (c=0.1, CHCl$_3$)
$^1$HNMR (400 MHz, CDCl$_3$) δ: 2.52-2.68 (4H, m), 4.09 (3H, s), 4.15 (3H, s), 4.42-4.48 (1H, m), 4.74 (1H, d, J=18.1 Hz), 5.27 (2H, s), 5.78 (1H, d, J=18.1 Hz), 7.31-7.46 (5H, m), 7.38 (1H, dd, J=2.7, 9.0 Hz), 7.53-7.59 (2H, m), 7.93 (1H, s), 8.46 (1H, d, J=9.0 Hz), 9.17 (1H, d, J=2.7 Hz)

Step 9
yield: 54.9%, $[\alpha]_D^{29}$+111.51 (c=0.11, CHCl$_3$)
$^1$HNMR (400 MHz, CDCl$_3$) δ: 2.20-2.37 (1H, m), 2.48-2.67 (2H, m), 2.70-2.81 (1H, m), 3.68 (3H, s), 3.85-3.93 (1H, m), 3.68 (3H, s), 3.85-3.93 (1H, m), 4.07 (3H, s), 4.35 (1H, d, J=17.6 Hz), 5.08 (1H, d, J=17.6 Hz), 5.12 (1H, s), 5.22-5.32

(2H, m), 6.70-6.75 (1H, m), 7.31-7.38 (2H, m), 7.39-7.45 (2H, m), 7.51-7.57 (2H, m), 7.76-7.79 (2H, m), 8.41 (1H, dd, J=9.3 Hz)

Step 10 yield: 66.9%, $[\alpha]_D^{29}$+104.86 (c=0.3, CHCl$_3$)

$^1$HNMR (400 MHz, DMSO-d$_6$) δ: 1.75-1.93 (3H, m), 2.11-2.28 (1H, m), 2.30-2.46 (2H, m), 3.92 (3H, s), 3.99 (3H, s), 3.20-3.35 (1H, m), 3.49 (1H, d, J=15.9 Hz), 4.60 (1H, d, J=15.9 Hz), 4.73 (1H, d, J=9.8 Hz), 4.95 (1H, d, J=9.8 Hz), 5.21-5.31 (2H, m), 7.23 (1H, s), 7.29 (1H, dd, J=2.4, 9.0 Hz), 7.31-7.37 (1H, m), 7.38-7.45 (2H, m), 7.49-7.58 (2H, m), 7.84 (1H, d, J=2.4 Hz), 8.07 (1H, s), 8.67 (1H, d, J=9.0 Hz)

A phenolic hydroxyl group was protected as benzyl ether. It was deprotected by hydrogenolysis in the final stage.

Step 11: Hydrogenolysis of Benzyl Ether

Into a suspension of 53 mg (0.12 mmol) of the compound obtained by the step 10 in 10 mL of methanol, 5 mg of 10% palladium on carbon was added, followed by stirring under a hydrogen atmosphere. After three hours, the disappearance of the raw materials was confirmed, and the palladium on carbon was removed by filtration. The resulting filtrate was distilled under reduced pressure and the residual product was purified by column chromatography (chloroform:methanol=40:1) to give 32 mg (75.3%) of a white solid.

$[\alpha]_D^{28}$+137.83 (c=0.11, CHCl$_3$: CH$_3$OH=1:1)

$^1$HNMR (400 MHz, DMSO-d$_6$) δ: 1.78-1.91 (3H, m), 2.10-2.26 (1H, m), 2.28-2.45 (2H, m), 3.47 (1H, d, J=15.6 Hz), 3.90 (3H, s), 3.98 (3H, s), 3.20-3.35 (1H, m), 4.52 (1H, d, J=10.0 Hz), 4.57 (1H, d, J=15.6 Hz), 4.80 (1H, dd, J=2.0, 10.0 Hz), 7.09 (1H, dd, J=2.6, 8.9 Hz), 7.19 (1H, s), 7.62 (1H, d, J=2.6 Hz), 8.0 (1H, s), 8.55 (1H, d, J=8.9 Hz), 9.62 (1H, brs)

Synthesis Example 3

A compound having the following groups at R$^1$ to R$^6$ was synthesized. The operations and the yield of each step are shown below.

TABLE 3

| Compound 30 | | | | | |
| --- | --- | --- | --- | --- | --- |
| R$^1$ | R$^2$ | R$^3$ | R$^4$ | R$^5$ | R$^6$ |
| H | H | OH | H | OCH$_3$ | OCH$_3$ |

Step 1 yield: quant $^1$HNMR (400 MHz, CDCl$_3$) δ: 3.93 (3H, s), 3.96 (3H, s), 5.14 (2H, s), 6.92 (1H, dd, J=8.5 Hz), 7.01-7.07 (1H, m), 7.14 (1H, d, J=2.4 Hz), 7.26 (1H, dd, J=2.4, 8.5 Hz), 7.31-7.48 (8H, m), 7.53-7.56 (1H, m)

Step 2 yield: 88.7%

A mixture of regioisomers with respect to a benzyloxy group on the aromatic ring (an isomer ratio of 66:34) was isolated.

Step 3 yield: 97.6%

A mixture of regioisomers with respect to a benzyloxy group on the aromatic ring (an isomer ratio of 66:34) was isolated.

Step 4 yield: quant

A mixture of regioisomers with respect to a benzyloxy group on the aromatic ring (an isomer ratio of 66:34) was isolated.

Step 5 yield: 87.8%

A mixture of regioisomers with respect to a benzyloxy group on the aromatic ring (an isomer ratio of 66:34) was isolated.

Step 6 yield: 53.0%, $[\alpha]_D^{23}$+54.73 (c=0.11, CHCl$_3$)

$^1$HNMR (400 MHz, CDCl$_3$) δ: 1.20 (3H, d, J=6.2 Hz), 1.21 (3H, d, J=6.2 Hz), 1.90-1.99 (1H, m), 2.01-2.12 (1H, m), 2.28-2.44 (1H, m), 2.54-2.65 (1H, m), 3.26 (3H, s), 3.62-3.70 (1H, m), 3.99 (3H, s), 4.30 (1H, d, J=14.6 Hz), 5.04 (1H, heptet, J=6.2 Hz), 5.26 (2H, s), 5.68 (1H, d, J=14.4 Hz), 7.22-7.26 (1H, m), 7.39-7.50 (6H, m), 7.55 (1H, s), 7.52-7.62 (2H, m), 9.12 (1Hs,)

Step 7 yield: 90.7%

$^1$HNMR (400 MHz, DMSO-d$_6$) δ: 1.80-1.95 (1H, m), 2.02-2.20 (1H, m), 2.24-2.44 (2H, m), 3.14 (3H, s), 3.57-3.66 (1H, m), 3.82 (3H, s), 4.26 (1H, d, J=14.6 Hz), 5.27-5.35 (2H, m), 5.39 (1H, d, J=14.6 Hz), 7.36-7.56 (8H, m), 7.62-7.70 (2H, m), 9.03 (1H, s)

Step 8 yield: 44.5%, $[\alpha]_D^{29}$+226.62 (c=0.1, CHCl$_3$)

$^1$HNMR (400 MHz, CDCl$_3$) δ: 2.52-2.68 (4H, m), 3.24 (3H, s), 4.04 (3H, s), 4.42-4.50 (1H, m), 4.70 (1H, d, J=17.9 Hz), 5.20-5.30 (2H, m), 5.75 (1H, d, J=17.9 Hz), 7.28-7.36 (2H, m), 7.40-7.49 (3H, m), 7.55-7.64 (3H, m), 8.90-8.98 (1H, m), 9.14 (1H, s)

Step 9 yield: 43.1%, $[\alpha]_D^{28}$+205.68 (c=0.10, CHCl$_3$)

$^1$HNMR (400 MHz, CDCl$_3$) δ: 2.27-2.41 (1H, m), 2.52-2.64 (2H, m), 2.70-2.81 (1H, m), 3.24 (3H, s), 3.95-4.043.93 (2H, m), 4.01 (3H, s), 4.57 (1H, d, J=17.5 Hz), 5.27 (2H, s), 5.30 (1H, d, J=2.2 Hz), 5.47 (1H, d, J=17.5 Hz), 7.21 (1H, s), 7.30 (1H, d, J=8.1 Hz), 7.41-7.48 (3H, m), 7.55-7.64 (3H, m), 8.00 (1H, d, J=8.1 Hz), 9.17 (1H, s)

Step 10 yield: 55.9%, $[\alpha]_D^{29}$+84.08 (c=0.11, CHCl$_3$)

$^1$HNMR (400 MHz, DMSO-d$_6$) δ: 1.75-1.93 (3H, m), 2.11-2.28 (1H, m), 2.30-2.46 (2H, m), 3.13 (3H, s), 3.20-3.35 (1H, m), 3.50 (1H, d, J=15.7 Hz), 3.88 (3H, s), 4.58 (1H, d, J=17.5 Hz), 4.60-4.66 (1H, m), 4.94 (1H, dd, J=2.1, 9.6 Hz), 7.22 (1H, s), 7.37 (1H, d, J=7.9 Hz), 7.40-7.49 (4H, m), 7.51-7.58 (1H, m), 7.62-7.68 (1H, m), 8.02 (1H, d, J=7.9 Hz), 9.07 (1H, s)

Step 11 yield: 61.2%, $[\alpha]_D^{28}$+88.17 (c=0.11, CHCl$_3$: CH$_3$OH=1:1)

$^1$HNMR (400 MHz, DMSO-d$_6$) δ: 1.75-1.91 (3H, m), 2.10-2.26 (1H, m), 2.28-2.45 (2H, m), 3.50 (1H, d, J=15.9 Hz), 3.91 (3H, s), 3.93 (3H, s), 4.10-4.15 (1H, m), 4.52-4.58 (1H, m), 4.59 (1H, d, J=15.9 Hz), 4.89 (1H, dd, J=2.0, 10.0 Hz), 7.06 (1H, d, J=7.8 Hz), 7.24 (1H, s), 7.36 (1H, t, J=7.8 Hz), 7.64-7.75 (1H, m), 7.84 (1H, d, J=7.8 Hz), 9.48 (1H, s), 10.45 (1H, brs)

Synthesis Example 5

A compound having the following groups at R$^1$ to R$^6$ was synthesized. The operations and the yield of each step are shown below.

TABLE 4

| | | Compound 3 | | | |
|---|---|---|---|---|---|
| R$^1$ | R$^2$ | R$^3$ | R$^4$ | R$^5$ | R$^6$ |
| H | CH$_3$CH$_2$ | H | H | OCH$_3$ | OCH$_3$ |

Step 1
  yield: 92%
  $^1$HNMR (400 MHz, CDCl$_3$) δ: 1.27 (3H, t, J=7.6 Hz), 2.71 (2H, q, J=7.6 Hz), 3.93 (3H, s), 3.96 (3H, s), 6.92 (1H, d, J=8.8 Hz), 7.15 (1H, d, J=2.4 Hz), 7.26 (1H, dd, J=8.8 Hz, 2.4 Hz), 7.29 (2H, d, J=8.4 Hz), 7.41 (1H, s), 7.81 (2H, d, J=8.4 Hz)
Step 2
  yield: 71%
  $^1$HNMR (400 MHz, CDCl$_3$) δ: 1.40 (3H, t, J=7.8 Hz), 2.95 (2H, q, J=7.8 Hz), 4.11 (3H, s), 4.16 (3H, s), 7.49 (1H, dd, J=1.5 Hz, 7.8 Hz), 7.60 (1H, s), 7.84 (1H, d, J=8.3), 8.00 (1H, s), 7.14 (1H, s), 8.30 (1H, s)
Step 3
  yield: quant
  $^1$HNMR (400 MHz, CDCl$_3$) δ: 1.44 (3H, t, J=7.58 Hz), 2.96 (2H, q, J=7.58 Hz), 4.12 (3H, s), 4.16 (3H, s), 7.49 (1H, dd, J=8.28 Hz, 1.48 Hz), 7.96 (1H, d, J=8.28 Hz), 8.02 (1H, s), 8.15 (1H, s), 8.32 (1H, s), 8.98 (1H, s), 10.30 (1H, s)
Step 4
  yield: 97.0%
  $^1$HNMR (400 MHz, CDCl$_3$) δ: 1.38 (3H, t, J=7.60), 2.92 (2H, q, J=7.60 Hz), 4.08 (3H, s), 4.15 (3H, s), 5.14-5.16 (2H, m), 7.41 (1H, dd, J=8.18 Hz, 1.34 Hz), 7.57 (1H, s), 7.66 (1H, s), 7.79 (1H, d, J=8.18 Hz), 8.05 (1H, s), 8.275-8.30 (1H, m)
Step 5
  yield: 91.8%
  $^1$HNMR (400 MHz, CDCl$_3$) δ: 1.38 (3H, t, J=7.56 Hz), 2.91 (2H, q, J=7.56 Hz), 4.11 (3H, s), 4.15 (3H, s), 4.99 (2H, s), 7.41 (1H, dd, J=8.04 Hz, 1.48 Hz), 7.55 (1H, s), 7.74 (1H, s), 7.77 (1H, d, J=8.04 Hz), 8.04 (1H, s), 8.27 (1H, s)
Step 6
  yield: 79.3%, 98.83% ee (HPLC condition A), [α]$_D^{25}$+95.37 (c=0.10, CHCl$_3$)
  $^1$HNMR (400 MHz, CDCl$_3$) δ: 1.19 (3H, d, J=6.36 Hz), 1.21 (3H, d, J=6.36 Hz), 1.39 (3H, t, J=7.56 Hz), 1.90-2.65 (4H, m), 2.92 (2H, q, J=7.56 Hz), 3.71 (1H, dd, J=3.64 Hz, 9.24 Hz), 4.04 (3H, s), 4.14 (3H, s), 4.42 (1H, d, J=14.4 Hz), 5.02 (1H, heptet, J=6.36 Hz), 5.64 (1H, d, J=14.4 Hz), 7.40 (1H, dd, J=8.08 Hz, 1, 44 Hz), 7.46 (1H, s), 7.62 (1H, s), 7.73 (1H, d, J=8.08 Hz), 8.02 (1H, s), 8.28 (1H, s)
<Enantiomer>
  yield: 88.1%, 99.64% ee, [α]$_D^{28}$-86.07 (c=0.12, CHCl$_3$)
Step 7
  yield: 81.4%
  $^1$HNMR (400 MHz, DMSO-d$_6$) δ: 1.39 (3H, t, J=7.56 Hz), 2.00-2.68 (4H, m), 2.92 (2H, q, J=7.56 Hz), 3.86 (1H, dd, J=3.44 Hz, 9.04 Hz), 4.05 (3H, s), 4.14 (3H, s), 4.34 (1H, d, J=14.4 Hz), 5.69 (1H, d, J=14.4 Hz), 7.42 (1H, dd, J=1.44 Hz, 8.08 Hz), 7.52 (1H, s), 7.62 (1H, s), 7.77 (1H, d, J=8.08 Hz), 8.03 (1H, s)
Step 8
  yield: 64.1%, 99.12% ee (HPLC analysis condition B), [α]$_D^{28}$+147.10 (c=0.09, CHCl$_3$)
  $^1$HNMR (400 MHz, CDCl$_3$) δ: 1.39 (3H, t, J=7.56 Hz), 2.52-2.66 (4H, m), 2.92 (2H, q, J=7.56 Hz), 4.09 (3H, s), 4.18 (3H, s), 4.42-4.47 (1H, m), 4.71 (1H, d, J=18.08 Hz), 5.75 (1H, d, J=18.08 Hz), 7.34 (1H, s), 7.52 (1H, dd, J=1.82 Hz, 8.80 Hz), 8.02 (1H, s), 8.30 (1H, s), 9.29 (1H, d, J=8.80 Hz)
<Enantiomer>
  yield: 68.6%, 91.12% ee, [α]$_D^{28}$-122.46 (c=0.086, CHCl$_3$)
Step 9
  yield: 26.4%, 98.2% ee (HPLC analysis condition A), [α]$_D^{27}$+177.18 (c=0.06, CHCl$_3$)
  $^1$HNMR (400 MHz, CDCl$_3$) δ: 1.38 (3H, t, J=7.6 Hz), 2.26-2.78 (4H, m), 2.91 (2H, q, J=7.6 Hz), 3.95-3.99 (1H, m), 4.02 (3H, s), 4.13 (3H, s), 4.54 (1H, d, J=17.6 Hz), 5.29 (1H, d, J=2.4 Hz), 5.43 (1H, d, J=17.6 Hz), 7.50 (1H, dd, J=1.7 Hz, 8.8 Hz), 7.18 (1H, s), 8.01 (1H, s), 8.19 (1H, d, J=8.8 Hz), 8.31 (1H, s)
<Enantiomer>
  yield: 26.7%, 96.4% ee, [α]$_D^{28}$-172.91 (c=0.06, CHCl$_3$)
Step 10
  yield: 22.4%, 99.9% ee (HPLC condition B), [α]$_D^{29}$+91.29 (c=0.02, CHCl$_3$)
  $^1$HNMR (400 MHz, DMSO-d$_6$) δ: 1.32 (3H, t, J=7.8 Hz), 1.80-1.88 (3H, brs), 2.10-2.46 (3H, m), 2.86 (2H, q, J=7.8 Hz), 3.29-3.38 (1H, m), 3.49 (1H, d, J=15.64 Hz), 3.93 (3H, s), 4.02 (3H, s), 4.58 (1H, d, J=15.64 Hz), 4.62 (1H, d, J=10.24 Hz), 4.91-4.99 (1H, m), 7.23 (1H, s), 7.40-7.48 (1H, m), 8.15 (1H, s), 8.32 (1H, d, J=8.8 Hz), 8.52 (1H, s)
  The yield and the specific optical rotation of the compound 4 are shown below.
<Enantiomer> (compound 4)
  yield: 33.6%, 98.62% ee, [α]$_D^{29}$-89.30 (c=0.07, CHCl$_3$)

Synthesis Example 6

A compound having the following groups at R$^1$ to R$^6$ was synthesized. The operation and the yield of each operation are shown below.

TABLE 5

| | | Compound 5 | | | |
|---|---|---|---|---|---|
| R$^1$ | R$^2$ | R$^3$ | R$^4$ | R$^5$ | R$^6$ |
| H | F | H | H | OCH$_3$ | OCH$_3$ |

Step 1
  yield: 95%
  $^1$HNMR (400 MHz, CDCl$_3$) δ: 3.94 (3H, s), 3.96 (3H, s), 6.93 (1H, d, J=8.4 Hz), 7.14 (1H, d, J=2.4 Hz), 7.11-7.20 (1H, m), 7.26 (1H, dd, J=2.4 Hz, 8.4 Hz), 7.82-7.92 (2H, m)
Step 2
  yield: 69%
  $^1$HNMR (400 MHz, CDCl$_3$) δ: 4.12 (3H, s), 4.14 (3H, s), 7.33-7.42 (1H, m), 7.60 (1H, s), 7.84 (1H, s), 7.88-7.96 (1H, m), 8.09-8.16 (1H, m), 8.14 (1H, s)
Step 3
  yield: 81%
  $^1$HNMR (400 MHz, CDCl$_3$) δ: 4.12 (3H, s), 4.14 (3H, s), 7.32-7.42 (1H, m), 7.85 (1H, s), 8.00-8.08 (1H, m), 8.11-8.18 (1H, m), 8.15 (1H, s), 8.97 (1H, s), 10.30 (1H, s)
Step 4
  yield: 93%
  $^1$HNMR (400 MHz, CDCl$_3$) δ: 4.08 (3H, s), 4.13 (3H, s), 5.15 (2H, s), 7.25-7.30 (1H, m), 7.56 (1H, s), 7.68 (1H, s), 7.81-7.87 (1H, m), 7.88 (1H, s), 8.08-8.14 (1H, m)
Step 5
  yield: 89.3%
  $^1$HNMR (400 MHz, CDCl$_3$) δ: 4.12 (3H, s), 4.13 (3H, s), 4.98 (2H, s), 7.26-7.32 (1H, m), 7.55 (1H, s), 7.74 (1H, s), 7.80-7.86 (1H, m), 7.88 (1H, s), 8.05-8.15 (1H, m)

Step 6
  yield: 70.5%, 99.2% ee (HPLC condition A), $[\alpha]_D^{27}$+83.31 (c=0.12, CHCl$_3$)
  $^1$HNMR (400 MHz, CDCl$_3$) δ: 1.17 (3H, d, J=6.36 Hz), 1.18 (3H, d, J=6.36 Hz), 1.90-2.64 (4H, m), 3.70-3.75 (1H, m), 4.05 (3H, s), 4.12 (3H, s), 4.37 (1H, d, J=14.52 Hz), 5.00 (1H, heptet, V6.36 Hz), 5.59 (1H, d, J=14.52 Hz), 7.26-7.32 (1H, m), 7.47 (1H, s), 7.65 (1H, s), 7.75-7.80 (1H, m), 7.86 (1H, s), 8.05-8.15 (1H, m)
  <Enantiomer>
    yield: 66.5%, 99.6% ee, $[\alpha]_D^{29}$-80.38 (c=0.11, CHCl$_3$)
Step 7
  $^1$HNMR (400 MHz, DMSO-d$_6$) δ: 1.85-2.44 (4H, m), 3.65-3.73 (1H, m), 3.88 (3H, s), 4.01 (3H, s), 4.28 (1H, d, J=14.52 Hz), 5.39 (1H, d, J=14.52 Hz), 7.40-7.46 (1H, m), 7.55 (1H, s), 7.58 (1H, s), 7.95-8.00 (1H, m), 8.14 (1H, s), 8.50-8.65 (1H, m)
  yield: 89.0%
Step 8
  yield: 60.0%, 99.9% ee (HPLC condition B), $[\alpha]_D^{27}$+187.74 (c=0.10, CHCl$_3$)
  $^1$HNMR (400 MHz, CDCl$_3$) δ: 2.50-2.68 (4H, m), 4.11 (3H, s), 4.17 (3H, s), 4.41-4.48 (1H, m), 4.72 (1H, d, J=18.04 Hz), 5.76 (1H, d, J=18.04 Hz), 7.35 (1H, s), 7.36-7.42 (1H, m), 7.86 (1H, s), 8.10-8.15 (1H, m), 9.40-9.46 (1H, m)
  <Enantiomer>
    yield: 57.4%, 99.9% ee, $[\alpha]_D^{28}$-187.93 (c=0.10, CHCl$_3$)
Step 9
  yield: 94.9%, 100% ee (HPLC condition A), $[\alpha]_D^{27}$+214.61 (c=0.10, CHCl$_3$)
  $^1$HNMR (400 MHz, CDCl$_3$) δ: 2.30-2.80 (4H, m), 3.75-4.00 (1H, m), 4.00 (3H, s), 4.13 (3H, s), 4.52 (1H, d, J=17.56 Hz), 5.26 (1H, d, J=1.76 Hz), 5.39 (1H, d, J=17.56 Hz), 7.14 (1H, s), 7.35-7.42 (1H, m), 7.84 (1H, s), 8.13-8.17 (1H, m), 8.25-8.31 (1H, m)
  <Enantiomer>
    yield: 86.1%, 99.62% ee, $[\alpha]_D^{27}$-210.93 (c=0.11, CHCl$_3$)
Step 10
  yield: 79.8%, 100% ee (HPLC condition B), $[\alpha]_D^{27}$+159.42 (c=0.34, CHCl$_3$)
  $^1$HNMR (400 MHz, DMSO-d$_6$) δ: 1.84 (3H, brs), 2.10-2.52 (3H, m), 3.30-3.33 (1H, m), 3.50 (1H, d, J=15.6 Hz), 3.94 (3H, s), 4.01 (3H, s), 4.61 (1H, d, J=15.6 Hz), 4.75 (1H, d, J=9.76 Hz), 4.93-4.99 (1H, m), 7.27 (1H, s), 7.41-7.48 (1H, m), 8.11 (1H, s), 8.30-8.37 (1H, m), 8.55-8.61 (1H, m)

The yield and the specific optical rotation of the compound 6 are shown below.
  <Enantiomer> (compound 6)
    yield: 64.8%, 100% ee, $[\alpha]_D^{28}$-154.04 (c=0.21, CHCl$_3$)

Reference Example 1

A compound having the following groups at $R^1$ to $R^6$ was synthesized as an acyl precursor. The operation and the yield of each operation are shown below.

TABLE 6

| Known compound 1 As an acyl precursor | | | | | |
| --- | --- | --- | --- | --- | --- |
| $R^1$ | $R^2$ | $R^3$ | $R^4$ | $R^5$ | $R^6$ |
| H | OH | H | H | OCH$_3$ | OCH$_3$ |

Step 1
  yield: 93%
  $^1$H-NMR (400 MHz, CDCl$_3$) δ: 3.93 (3H, s), 3.96 (3H, s), 5.14 (2H, s), 6.92 (1H, d, J=8.3 Hz), 7.03-7.06 (1H, m), 7.13 (1H, d, J=2.2 Hz), 7.24 (1H, dd, J=2.2, 8.3 Hz), 7.35-7.47 (5H, m), 7.36 (1H, s), 7.85-7.88 (1H, m)
Step 2
  yield: 69.0%
  $^1$H-NMR (400 MHz, CDCl$_3$) δ: 4.10 (3H, s), 4.11 (3H, s), 5.32 (2H, s), 7.28-7.55 (6H, m), 7.58 (1H, s), 7.80 (1H, s), 7.85 (1H, d, J=9.0 Hz), 7.91-7.92 (1H, m), 8.10 (1H, s)
Step 3
  yield: 86%
  $^1$H-NMR (400 MHz, CDCl$_3$) δ: 4.11 (6H, s), 5.34 (2H, s), 7.34 (1H, dd, J=2.3, 8.8 Hz), 7.38-7.46 (3H, m), 7.54-7.56 (2H, m), 7.81 (1H, s), 7.94 (1H, d, J=2.3 Hz), 7.96 (1H, d, J=8.8 Hz), 8.99 (1H, s), 10.26 (1H, s)
Step 4
  yield: 96%
  $^1$H-NMR (400 MHz, CDCl$_3$) δ: 4.07 (3H, s), 4.10 (3H, s), 5.12 (2H, d, J=5.9 Hz), 5.29 (2H, s), 7.25-7.29 (1H, m), 7.36-7.38 (1H, m), 7.41-7.45 (2H, m), 7.52-7.55 (2H, m), 7.57 (1H, m), 7.62 (1H, s), 7.79 (1H, d, J=8.8 Hz), 7.86 (1H, s), 7.94 (1H, d, J=2.2 Hz)
Steps 5 and 6
  yield: 79%, 99.6% ee (HPLC condition A)
  $^1$H-NMR (400 MHz, CDCl$_3$) δ: 1.19 (6H, t, J=5.9 Hz), 1.92-2.64 (4H, m), 3.72 (1H, dd, J=3.7, 9.0 Hz), 4.04 (3H, s), 4.09 (3H, s), 4.31 (1H, d, J=14.6 Hz), 4.98-5.04 (1H, m), 5.29 (2H, s), 5.60 (1H, d, J=14.6 Hz), 7.25-7.28 (1H, m), 7.34-7.45 (4H, m), 7.53-7.55 (2H, m), 7.60 (1H, s), 7.72 (1H, d, J=8.8 Hz), 7.83 (1H, s), 7.92-7.93 (1H, m)
  <Enantiomer>
    yield: 99%, $[\alpha]_D^{32}$-55.2° (c=0.1, CHCl$_3$)
Step 7
  yield: 99%
  $^1$H-NMR (400 MHz, CDCl$_3$) δ: 2.00-2.65 (4H, m), 3.84-3.88 (1H, m), 4.04 (3H, s), 4.09 (3H, s), 4.33 (1H, d, J=14.4 Hz), 5.27 (2H, s), 5.64 (1H, d, J=14.4 Hz), 7.24-7.54 (7H, m), 7.61 (1H, s), 7.76 (1H, d, J=8.8 Hz), 7.83 (1H, s), 7.92-7.93 (1H, m)
Step 8
  yield: 60%, 100% ee (HPLC condition B)
  $^1$H-NMR (400 MHz, CDCl$_3$) δ: 2.52-2.63 (4H, m), 4.08 (3H, s), 4.12 (3H, s), 4.41-4.44 (1H, m), 4.67 (1H, d, J=8.1 Hz), 5.30 (2H, s), 5.71 (1H, d, J=18.1 Hz), 7.30 (1H, s), 7.35-7.45 (4H, m), 7.53-7.55 (2H, m), 7.80 (1H, s), 7.93 (1H, d, J=2.4 Hz), 9.35 (1H, d, J=9.3 Hz)
  <Enantiomer>
    yield: 39%, $[\alpha]_D^{32}$-94.0° (c=0.06, CHCl$_3$)
Step 9
  yield: 74%
  $^1$H-NMR (400 MHz, CDCl$_3$) δ: 2.30-2.76 (4H, m), 3.97-4.02 (1H, m), 4.02 (3H, s), 4.10 (3H, s), 4.52 (1H, d, J=17.6 Hz), 5.25-5.27 (1H, m), 5.31 (2H, s), 5.41 (1H, d, J=17.6 Hz), 7.35-7.45 (5H, m), 7.52-7.55 (2H, m), 7.82 (1H, s), 7.98 (1H, d, J=2.4 Hz), 8.21 (1H, d, J=9.3 Hz)
  <Enantiomer>
    yield: 48%, $[\alpha]_D^{32}$-94.0° (c=0.1, CHCl$_3$)
Step 10
  yield: 93%
  $^1$H-NMR (400 MHz, DMSO-d$_6$) δ: 1.80-1.85 (3H, br), 2.12-2.14 (1H, m), 2.33-2.43 (2H, m), 3.28-3.30 (1H, m), 3.48 (1H, d, J=15.1 Hz), 3.93 (3H, s), 4.02 (3H, s), 4.57 (1H, d, J=15.1 Hz), 4.61-4.63 (1H, m), 4.92-4.94 (1H, m), 5.36 (2H, s), 7.23 (1H, s), 7.31 (1H, dd, J=2.6, 9.2 Hz), 7.33-7.35

(1H, m), 7.40-7.43 (2H, m), 7.56-7.58 (2H, m), 8.03 (1H, s), 8.15 (1H, d=2.6 Hz), 8.22 (1H, d=9.2 Hz)
<Enantiomer>
yield: quant, $[\alpha]_D^{32}$ −40.0° (c=0.06, CHCl$_3$)
Step 11
yield: 74%, 99.2% ee (HPLC condition B), $[\alpha]_D^{25}$+102.3 (c=0.12, CHCl$_3$: MeOH=1:1)
$^1$H-NMR (400 MHz, DMSO-d$_6$) δ: 1.75-1.88 (3H, br), 2.12-2.20 (1H, m), 2.30-2.42 (2H, m), 3.40-3.49 (2H, m), 3.92 (3H, m), 3.99 (3H, m), 4.53 (1H, d, J=16.1 Hz), 4.58-4.61 (1H, m), 4.90-4.92 (1H, m), 7.09 (1H, d, J=2.2, 9.0 Hz), 7.19 (1H, s), 7.91 (1H, s), 7.91 (1H, s), 8.12 (1H, d, J=9.0 Hz), 9.63 (1H, brs)
<Enantiomer>
yield: 52%, $[\alpha]_D^{31}$ −66.0° (c=0.1, CHCl$_3$-MeOH (1:1))

Synthesis Example 7

A compound having the following groups at R$^1$ to R$^6$ was synthesized. The operation and the yield of each operation are shown below.

TABLE 7

| | | | | | |
|---|---|---|---|---|---|
| | | | | | Compound 18 |
| R$^1$ | R$^2$ | R$^3$ | R$^4$ | R$^5$ | R$^6$ |
| H | (CH$_3$)$_2$CHCH$_2$O-C(O)-NH-⌇ | H | H | OCH$_3$ | OCH$_3$ |

Step 1
yield: 77.8%
$^1$HNMR (400 MHz, CDCl$_3$) δ: 3.93 (3H, s), 3.96 (3H, s), 6.79 (1H, brs), 6.87-7.89 (13H, m)
Step 2
yield: 36.9%
$^1$HNMR (400 MHz, CDCl$_3$) δ: 4.10 (3H, s), 4.12 (3H, s), 5.29 (2H, s), 7.05 (1H, brs), 7.35-7.53 (6H, m), 7.57 (1H, s), 7.84 (1H, d, J=8.8 Hz), 7.91 (1H, s), 8.08 (1H, s), 8.70-8.80 (1H, m)
Step 3
yield: 85.9%
$^1$HNMR (400 MHz, CDCl$_3$) δ: 1.02 (6H, d, J=6.8 Hz), 2.04 (1H, heptet, J=6.8 Hz), 4.05 (2H, d, J=6.8 Hz), 4.10 (3H, s), 4.13 (3H, s), 7.02 (1H, brs), 7.28-9.00 (6H, m), 10.26 (1H, s)
Step 4
yield: 54.3%
$^1$HNMR (400 MHz, CDCl$_3$) δ: 1.01 (6H, d, J=6.8 Hz), 2.03 (1H, heptet, J=6.8 Hz), 4.03 (2H, d, J=6.8 Hz), 4.05 (3H, s), 4.11 (3H, s), 5.10 (2H, s), 6.89 (1H, brs), 7.32-8.69 (6H, m)
Step 5
yield: 100%
$^1$HNMR (400 MHz, CDCl$_3$) δ: 1.01 (6H, d, J=6.8 Hz), 2.03 (1H, heptet, J=6.8 Hz), 4.03 (2H, d, J=6.8 Hz), 4.08-4.23 (6H, m), 4.97 (2H, s), 6.94 (1H, brs), 7.30-8.74 (6H, m)
Step 6
yield: 53.3%
$^1$HNMR (400 MHz, CDCl$_3$) δ: 1.01 (6H, d, J=6.8 Hz), 1.17 (3H, d, J=6.3 Hz), 1.19 (3H, d, J=6.3 Hz), 1.90-2.18 (3H, m), 2.32-2.46 (1H, m), 2.52-2.68 (1H, m), 3.73 (1H, dd, J=3.9, 9.3 Hz), 4.03 (2H, d, J=6.8 Hz), 4.04 (3H, s), 4.12 (3H, s), 4.34 (1H, d, J=14.4 Hz), 5.00 (1H, heptet, J=6.3 Hz), 5.60 (1H, d, J=14.4 Hz), 6.87-7.04 (1H, m), 7.34-8.75 (6H, m)

Step 7
yield: 92.0%
$^1$HNMR (400 MHz, DMSO-d$_6$) δ: 0.96 (6H, d, J=6.8 Hz), 1.80-1.94 (1H, m), 1.96 (1H, heptet, J=6.8 Hz), 2.06-2.21 (1H, m), 2.27-2.47 (2H, m), 3.67 (1H, dd, J=3.4, 9.3 Hz), 3.87 (3H, s), 3.93 (2H, d, J=6.8 Hz), 3.98 (3H, s), 4.23 (1H, d, J=14.9 Hz), 5.38 (1H, d, J=14.9 Hz), 7.35-8.75 (6H, m), 9.80-10.10 (1H, m)
Step 8
yield: 35.5%, 98.9% ee (HPLC condition B), $[\alpha]_D^{27}$+ 151.489 (c=0.1, CHCl$_3$)
$^1$HNMR (400 MHz, CDCl$_3$) δ: 1.01 (6H, d, J=6.6 Hz), 2.04 (1H, heptet, J=6.6 Hz), 2.48-2.68 (4H, m), 4.03 (2H, d, J=6.6 Hz), 4.09 (3H, s), 4.17 (3H, s), 4.40-4.49 (1H, m), 4.68 (1H, d, J=17.8 Hz), 5.73 (1H, d, J=17.8 Hz), 6.91 (1H, brs), 7.31 (1H, s), 7.41 (1H, dd, J=2.2, 9.3 Hz), 7.96 (1H, s), 8.80-8.96 (1H, m), 9.34 (1H, d, J=9.3 Hz)
Step 9
yield: 88.1%, 99.9% ee (HPLC condition A), $[\alpha]_D^{26}$+ 158.238 (c=0.11, CHCl$_3$)
$^1$HNMR (400 MHz, CDCl$_3$) δ: 1.02 (6H, d, J=6.6 Hz), 2.04 (1H, heptet, J=6.6 Hz), 2.25-2.41 (1H, m), 2.54-2.65 (2H, m), 2.67-2.82 (1H, m), 3.90-4.04 (1H, m), 4.01 (3H, s), 4.02 (2H, d, J=6.6 Hz), 4.08 (3H, s), 4.49 (1H, d, J=17.8 Hz), 5.23 (1H, d, J=2.2 Hz), 5.36 (1H, d, J=17.8 Hz), 7.03 (1H, brs), 7.11 (1H, s), 7.59 (1H, dd, J=2.2, 9.0 Hz), 7.84 (1H, s), 8.19 (1H, d, J=9.0 Hz), 8.65-8.76 (1H, m)
Step 10
yield: 93%, 99.9% ee (HPLC condition B), $[\alpha]_D^{26}$+83.565 (c=0.1, CHCl$_3$)
$^1$H-NMR (400 MHz, DMSO-d$_6$) δ: 1.80-1.85 (3H, m), 2.12-2.14 (1H, m), 2.33-2.43 (2H, m), 3.28-3.30 (1H, m), 3.48 (1H, d, J=15.1 Hz), 3.93 (3H, m), 4.02 (3H, s), 4.57 (1H, d, J=15.1 Hz), 4.61-4.63 (1H, m), 4.92-4.94 (1H, m), 5.36 (2H, s), 7.23 (1H, s), 7.31 (1H, dd, J=2.6, 9.2 Hz), 7.33-7.35 (1H, m), 7.40-7.43 (2H, m), 7.56-7.58 (2H, m), 8.03 (1H, s), 8.15 (1H, d=2.6 Hz), 8.22 (1H, d=9.2 Hz)

Synthesis Example 8

A compound having the following groups at R$^1$ to R$^6$ was synthesized. The operation and the yield of each operation are shown below.

TABLE 8

| | | | | | |
|---|---|---|---|---|---|
| | | | Compound 26 | | |
| R$^1$ | R$^2$ | R$^3$ | R$^4$ | R$^5$ | R$^6$ |
| H | NHZ | H | H | OCH$_3$ | OCH$_3$ |

Step 3
yield: 72.2%
$^1$HNMR (400 MHz, CDCl$_3$) δ: 4.10 (3H, s), 4.12 (3H, s), 5.30 (2H, s), 7.09 (1H, brs), 7.32-7.48 (4H, m), 4.53 (1H, dd, J=2.0, 8.8 Hz), 7.92 (1H, s), 7.95 (1H, d, J=8.8 Hz), 8.09 (1H, s), 8.68-8.74 (1H, m), 8.96 (1H, s), 10.26 (1H, s)
Step 4
yield: 74.1%
$^1$HNMR (400 MHz, CDCl$_3$) δ: 4.05 (3H, s), 4.08-4.13 (3H, m), 5.11 (2H, s), 5.28 (2H, s), 6.97 (1H, brs), 7.31-7.49 (6H, m), 7.52 (1H, s), 7.59 (1H, s), 7.76 (1H, J=8.5 Hz), 7.88-7.95 (1H, m), 8.58-8.67 (1H, m)
Step 5
yield: quant
$^1$HNMR (400 MHz, CDCl$_3$) δ: 4.10 (6H, s), 4.98 (2H, s), 5.28 (2H, s), 6.97 (1H, brs), 7.35-7.48 (6H, m), 7.53 (1H, s), 7.69 (1H, s), 7.77 (1H, d, J=8.5 Hz), 7.92-7.98 (1H, m), 8.62-8.71 (1H, m)

Step 6
yield: 40.4%

$^1$HNMR (400 MHz, CDCl$_3$) δ: 1.17 (3H, d, J=6.5 Hz), 1.19 (3H, d, J=6.5 Hz), 1.90-2.01 (1H, m), 2.08-2.16 (1H, m), 2.32-2.46 (1H, m), 2.52-2.65 (1H, m), 3.73 (1H, dd, J=3.7, 9.0 Hz), 4.04 (3H, s), 4.11 (3H, s), 4.34 (1H, d, J=14.4 Hz), 5.00 (1H, heptet, 6.5 Hz), 5.28 (2H, s), 5.60 (1H, d, J=14.4 Hz), 6.97 (1H, brs), 7.32-7.49 (7H, m), 7.61 (1H, s), 7.79 (1H, d, J=8.5 Hz), 7.94 (1H, s), 8.63-8.69 (1H, m)

Step 7
yield: 91.6%

$^1$HNMR (400 MHz, DMSO-d$_6$) δ: 1.82-1.92 (1H, m), 2.06-2.18 (1H, m), 2.28-2.45 (2H, m), 3.66 (1H, dd, J=3.4, 9.0 Hz), 3.87 (3H, s), 3.97 (3H, s), 4.23 (1H, d, J=14.4 Hz), 5.22 (2H, s), 5.39 (1H, d, J=14.4 Hz), 7.32-7.37 (1H, m), 7.38-7.43 (2H, m), 7.44-7.49 (3H, m), 7.54 (1H, s), 7.82 (1H, d, J=8.8 Hz), 7.89 (1H, s), 8.71-8.72 (1H, m), 10.03 (1H, brs)

Step 8
yield: 80.6%

$^1$HNMR (400 MHz, CDCl$_3$) δ: 2.50-2.67 (4H, m), 4.10 (3H, s), 4.12-4.18 (3H, m), 4.40-4.47 (1H, m), 4.69 (1H, d, J=18.1 Hz), 5.29 (2H, s), 5.74 (1H, d, J=18.1 Hz), 6.99 (1H, brs), 7.30-7.48 (7H, m), 7.92-7.98 (1H, m), 8.81-8.89 (1H, m), 9.34 (1H, d, J=9.3 Hz)

Step 9
yield: 47.6%

$^1$HNMR (400 MHz, CDCl$_3$) δ: 2.26-2.39 (1H, m), 2.53-2.64 (2H, m), 2.70-2.81 (1H, m), 3.97-4.04 (1H, m), 3.98 (6H, s), 4.47 (1H, d, J=18.1 Hz), 5.21 (1H, d, J=2.2 Hz), 5.29 (2H, s), 5.33 (1H, d, J=18.1 Hz), 7.03-7.09 (1H, m), 7.15-7.23 (1H, m), 7.33-7.48 (5H, m), 7.52 (1H, dd, J=2.2, 9.0 Hz), 7.70-7.77 (1H, m), 8.17 (1H, d, J=9.0 Hz), 8.60-8.70 (1H, m)

Step 10
yield: 56.2%

$^1$HNMR (400 MHz, DMSO-d$_6$) δ: 1.75-1.90 (3H, m), 2.09-2.26 (1H, m), 2.28-2.46 (2H, m), 3.25-3.35 (1H, m), 3.48 (1H, d, J=14.9 Hz), 3.94 (3H, s), 3.97 (3H, s), 4.58 (1H, d, J=14.9 Hz), 4.63-4.70 (1H, m), 4.91-4.97 (1H, m), 5.22 (2H, s), 7.20-7.26 (1H, m), 7.32-7.49 (5H, m), 7.66-7.74 (1H, m), 7.88 (1H, s), 8.21 (1H, d, J=9.0 Hz), 8.69-8.76 (1H, m), 9.91-10.02 (1H, m)

Synthesis Example 9

A compound having the following groups at $R^1$ to $R^6$ was synthesized. The operation and the yield of each operation are shown below.

TABLE 9

| Compound 25 | | | | | |
|---|---|---|---|---|---|
| $R^1$ | $R^2$ | $R^3$ | $R^4$ | $R^5$ | $R^6$ |
| H | NH$_2$ | H | H | OCH$_3$ | OCH$_3$ |

This compound is obtainable via hydrogenolysis of benzyl carbamate produced in the aforementioned step 10 (the reaction conditions are the same as those of step 11).

yield: 46.5%

$^1$HNMR (400 MHz, DMSO-d$_6$) δ: 1.75-1.88 (3H, m), 2.10-2.24 (1H, m), 2.29-2.42 (2H, m), 3.25-3.35 (1H, m), 3.42 (1H, d, J=14.9 Hz), 3.91 (3H, s), 3.96 (3H, s), 4.46 (1H, d, J=10.0 Hz), 4.52 (1H, d, J=14.9 Hz), 4.87 (1H, dd, J=2.5, 10.0 Hz), 5.29 (2H, s), 6.93 (1H, dd, J=2.0, 8.8 Hz), 7.16 (1H, s), 7.68 (1H, d, J=2.0 Hz), 7.86 (1H, s), 7.98 (1H, d, J=8.8 Hz)

Phenanthroindolizidine alkaloid having an alkylcarbonyloxy group at $R^2$ or $R^8$ was synthesized by acylation of phenanthroindolizidine alkaloid having a corresponding hydroxyl group. The synthetic pathway is shown in the following step 12 or 13.

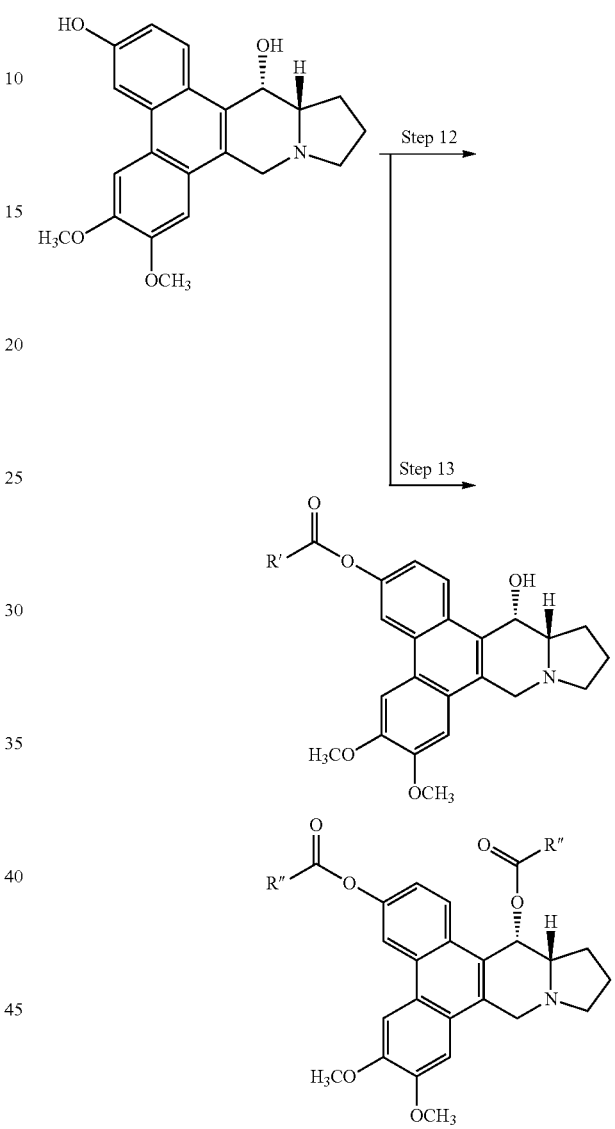

Synthesis Example 10

A compound having CH$_3$ at R', which is obtained through the aforementioned step 12, was synthesized. The operation and the yield of each operation are shown below (compound 7).

Step 12: Acylation of a Phenolic Hydroxyl Group

In a round-bottom flask, triethylamine (35 μl, 3.0 eq.) and acetic anhydride (36 μl, 2.2 eq.) were added to a suspension of raw materials (52 mg, 0.12 mmol) in methylene chloride (1 mL) under an argon atmosphere while stirring with cooling on ice. Dimethylaminopyridine (1.5 mg, 0.1 eq.) was further added, followed by stirring for six hours. The disappearance of the raw materials was confirmed, and then the resulting reaction liquid was concentrated and then purified through column chromatography (CHCl$_3$:MeOH=300:1) to give 12 mg (21.0%) of a yellow solid.

[α]$_D^{27}$+102.72 (c=0.016, CHCl$_3$)

$^1$HNMR (400 MHz, DMSO-d$_6$) δ: 1.78-1.92 (3H, m), 2.15-2.25 (1H, m), 2.30-3.05 (2H, m), 2.36 (3H, s), 3.25-3.40 (1H, m), 3.48-3.63 (1H, m), 3.94 (3H, m), 4.01 (3H, m), 4.59-5.05 (3H, m), 7.26 (1H, s), 7.35 (1H, dd, J=2.20 Hz, 9.03 Hz), 8.08 (1H, s), 8.32 (1H, d, J=9.03 Hz), 8.48 (1H, d, J=2.20 Hz)

Hereinbelow, compounds were synthesized using corresponding acid chloride in a similar manner as Synthesis Example 18.

Synthesis Example 11

A compound having CH$_3$CH$_2$ at R', which is obtained through the aforementioned step 12, was synthesized. The operation and the yield of each operation are shown below (compound 15).

yield: 90.2%, 99.6% ee (HPLC condition B), [α]$_D^{27}$+113.479 (c=0.12, CHCl$_3$)

$^1$HNMR (400 MHz, DMSO-d$_6$) δ: 1.20 (3H, t, J=7.4 Hz), 1.78-1.92 (3H, m), 2.15-2.25 (1H, m), 2.30-2.45 (2H, m), 2.70 (2H, q, J=7.4 Hz), 3.33-3.40 (1H, m), 3.48 (1H, d, J=15.9 Hz), 3.93 (3H, s), 4.00 (3H, s), 4.57 (1H, d, J=15.9 Hz), 4.75 (1H, d, J=9.8 Hz), 4.96 (1H, dd, J=2.0, 9.8 Hz), 7.34 (1H, dd, J=2.4, 9.2 Hz), 7.23 (1H, s), 8.01 (1H, s), 8.32 (1H, d, J=9.2 Hz), 8.45 (1H, d, J=2.4 Hz)

Synthesis Example 12

A compound having (CH$_3$)$_2$CH at R', which is obtained through the aforementioned step 12, was synthesized. The operation and the yield of each operation are shown below (compound 9).

yield: 93.1%, 99.3% ee (HPLC condition B), [α]$_D^{29}$+92.777 (c=0.1, CHCl$_3$)

$^1$HNMR (400 MHz, DMSO-d$_6$) δ: 1.32 (6H, d, J=7.0 Hz), 1.75-1.92 (3H, m), 2.10-2.26 (1H, m), 2.32-2.49 (2H, m), 2.91 (1H, heptet, J=7.0 Hz), 3.33-3.40 (1H, m), 3.50 (1H, d, J=15.6 Hz), 3.93 (3H, s), 4.01 (3H, s), 4.59 (1H, d, J=15.6 Hz), 4.75 (1H, d, J=9.8 Hz), 4.97 (1H, dd, J=2.1, 9.8 Hz), 7.25 (1H, s), 7.32 (1H, dd, J=2.2, 9.0 Hz), 8.08 (1H, s), 8.33 (1H, d, J=9.0 Hz), 8.43 (1H, d, J=2.2 Hz)

Synthesis Example 13

A compound having (CH$_3$)$_3$C at R', which is obtained through the aforementioned step 12, was synthesized. The operation and the yield of each operation are shown below (compound 10).

yield: 80.6%, 99.3% ee (HPLC condition B), [α]$_D^{30}$+89.723 (c=0.1, CHCl$_3$)

$^1$HNMR (400 MHz, DMSO-d$_6$) E: 1.39 (9H, s), 1.75-1.88 (3H, m), 2.10-2.26 (1H, m), 2.32-2.49 (2H, m), 3.33-3.40 (1H, m), 3.50 (1H, d, J=15.6 Hz), 3.94 (3H, s), 4.02 (3H, s), 4.59 (1H, d, J=15.6 Hz), 4.75 (1H, d, J=9.8 Hz), 4.97 (1H, dd, J=2.1, 9.8 Hz), 7.25 (1H, s), 7.30 (1H, dd, J=2.2, 9.0 Hz), 8.08 (1H, s), 8.33 (1H, d, J=9.0 Hz), 8.39 (1H, d, J=2.2 Hz)

Synthesis Example 14

A compound having

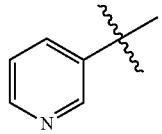 [SMILES: *c1cccnc1]

at R', which is obtained through the aforementioned step 12, was synthesized. The operation and the yield of each operation are shown below (compound 11).

yield: 85.0%, 99.9% ee (HPLC condition B), [α]$_D^{29}$+64.279 (c=0.1, CHCl$_3$)

$^1$HNMR (400 MHz, DMSO-d$_6$) δ: 1.80-1.92 (3H, m), 2.14-2.29 (1H, m), 2.32-2.49 (2H, m), 3.33-3.40 (1H, m), 3.50 (1H, d, J=15.6 Hz), 3.94 (3H, s), 3.99 (3H, s), 4.60 (1H, d, J=15.6 Hz), 4.80 (1H, d, J=10.0 Hz), 5.00 (1H, dd, J=2.2, 10.0 Hz), 7.26 (1H, s), 7.54 (1H, dd, J=2.4, 9.0 Hz), 7.70 (1H, ddd, J=1.0, 4.9, 8.2 Hz), 8.11 (1H, s), 8.39 (1H, d, J=9.0 Hz), 8.57 (1H, ddd, J=1.7, 2.2, 7.8 Hz), 8.71 (1H, d, J=2.4 Hz), 8.93 (1H, dd, J=1.7, 4.9 Hz), 9.36 (1H, dd, J=1.0, 2.2 Hz)

Synthesis Example 15

A compound having

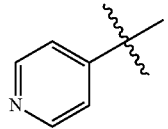 [SMILES: *c1ccncc1]

at R', which is obtained through the aforementioned step 12, was synthesized. The operation and the yield of each operation are shown below (compound 12).

yield: 82.9%, 99.9% ee (HPLC condition B), [α]$_D^{27}$+68.677 (c=0.1, CHCl$_3$)

$^1$HNMR (400 MHz, DMSO-d$_6$) δ: 1.80-1.92 (3H, m), 2.14-2.29 (1H, m), 2.32-2.49 (2H, m), 3.33-3.40 (1H, m), 3.52 (1H, d, J=15.6 Hz), 3.95 (3H, s), 3.98 (3H, s), 4.61 (1H, d, J=15.6 Hz), 4.91 (1H, d, J=10.0 Hz), 5.00 (1H, dd, J=2.1, 10.0 Hz), 7.27 (1H, s), 7.55 (1H, dd, J=2.2, 9.0 Hz), 8.04-8.14 (3H, m), 8.50 (1H, d, J=9.0 Hz), 8.71 (1H, d, J=2.2 Hz), 8.90-8.97 (2H, m)

Synthesis Example 16

A compound having

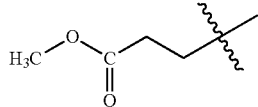 [SMILES: *CCC(=O)OC]

at R', which is obtained through the aforementioned step 12, was synthesized. The operation and the yield of each operation are shown below (compound 16).

yield: 81.4%, 99.2% ee (HPLC condition B), [α]$_D^{30}$+77.88 (c=0.1, CHCl$_3$)

$^1$HNMR (400 MHz, DMSO-d$_6$) δ: 1.80-1.92 (3H, m), 2.14-2.29 (1H, m), 2.32-2.49 (2H, m), 2.74 (2H, t, J=6.6 Hz), 2.95 (2H, t, J=6.6 Hz), 3.33-3.40 (1H, m), 3.49 (1H, d, J=16.1 Hz), 3.65 (3H, s), 3.94 (3H, s), 4.01 (3H, s), 4.58 (1H, d, J=16.1 Hz), 4.76 (1H, d, J=9.5 Hz), 4.97 (1H, d, J=9.5 Hz), 7.24 (1H, s), 7.32 (1H, dd, J=2.0, 9.3 Hz), 8.33 (1H, d, J=9.3 Hz), 8.44 (1H, d, J=2.0 Hz)

Synthesis Example 17

A compound having CH$_3$O at R', which is obtained through the aforementioned step 12, was synthesized. The operation and the yield of each operation are shown below (compound 17).

yield: 79.2%, 99.4% ee (HPLC condition B), [α]$_D^{26}$+ 118.53 (c=0.1, CHCl$_3$)

$^1$HNMR (400 MHz, DMSO-d$_6$) δ: 1.80-1.92 (3H, m), 2.14-2.29 (1H, m), 2.32-2.49 (2H, m), 3.33-3.40 (1H, m), 3.50 (1H, d, J=16.1 Hz), 3.88 (3H, s), 3.94 (3H, s), 4.01 (3H, s), 4.58 (1H, d, J=16.1 Hz), 4.80 (1H, d, J=9.5 Hz), 4.97 (1H, d, J=9.5 Hz), 7.24 (1H, s), 7.45 (1H, dd, J=2.0, 9.3 Hz), 8.11 (1H, s), 8.34 (1H, d, J=9.3 Hz), 8.63 (1H, d, J=2.0 Hz)

Synthesis Example 18

A compound having

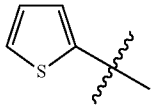 [SMILES: *c1cccs1]

at R', which is obtained through the aforementioned step 12, was synthesized. The operation and the yield of each operation are shown below (compound 19).

yield: 79.2%, 92.9% ee (HPLC condition B), [α]$_D^{28}$+ 52.894 (c=0.1, CHCl$_3$)

$^1$HNMR (400 MHz, DMSO-d$_6$) δ: 1.80-1.92 (3H, m), 2.14-2.29 (1H, m), 2.32-2.49 (2H, m), 3.33-3.40 (1H, m), 3.52 (1H, d, J=15.9 Hz), 3.94 (3H, s), 3.99 (3H, s), 4.61 (1H, d, J=15.9 Hz), 4.79 (1H, d, J=9.8 Hz), 5.00 (1H, d, J=9.8 Hz), 7.26 (1H, s), 7.35 (1H, dd, J=3.7, 4.9 Hz), 7.49 (1H, dd, J=2.2, 9.0 Hz), 8.11 (1H, dd, J=1.2, 3.7 Hz), 8.13 (1H, s), 8.13 (1H, dd, J=1.2, 3.7 Hz), 8.37 (1H, d, J=9.0 Hz), 8.67 (1H, d, J=2.2 Hz)

Synthesis Example 19

A compound having

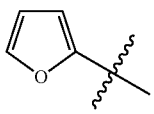 [SMILES: *c1ccco1]

at R', which is obtained through the aforementioned step 12, was synthesized. The operation and the yield of each operation are shown below (compound 20).

yield: 66.5%, 94.4% ee (HPLC condition B), [α]$_D^{26}$+ 46.929 (c=0.1, CHCl$_3$)

$^1$HNMR (400 MHz, DMSO-d$_6$) δ: 1.76-1.91 (3H, m), 2.10-2.29 (1H, m), 2.32-2.49 (2H, m), 3.33-3.40 (1H, m), 3.49 (1H, d, J=16.0 Hz), 3.94 (3H, s), 3.99 (3H, s), 4.57 (1H, d, J=15.9 Hz), 4.81 (1H, d, J=9.8 Hz), 4.98 (1H, dd, J=2.0, 9.8 Hz), 7.24 (1H, s), 7.48 (1H, dd, J=2.4, 9.0 Hz), 7.65 (1H, dd, J=0.7, 3.7 Hz), 8.11 (1H, s), 8.15 (1H, dd, J=0.7, 2.0 Hz), 8.37 (1H, d, J=9.0 Hz), 8.66 (1H, d, J=2.4 Hz)

Synthesis Example 20

A compound having (CH$_3$)$_2$N at R', which is obtained through the aforementioned step 12, was synthesized. The operation and the yield of each operation are shown below (compound 21).

yield: 86.8%, 86.0% ee (HPLC condition B), [α]$_D^{27}$+ 74.724 (c=0.1 CHCl$_3$)

$^1$HNMR (400 MHz, DMSO-d$_6$) δ: 1.75-1.92 (3H, m), 2.14-2.29 (1H, m), 2.32-2.49 (2H, m), 2.96 (3H, s), 3.14 (3H, s), 3.33-3.40 (1H, m), 3.51 (1H, d, J=15.6 Hz), 3.94 (3H, s), 4.01 (3H, s), 4.62 (1H, d, J=15.6 Hz), 4.72 (1H, d, J=9.8 Hz), 4.97 (1H, dd, J=2.0, 9.8 Hz), 7.27 (1H, s), 7.33 (1H, dd, J=2.2, 9.0 Hz), 8.08 (1H, s), 8.29 (1H, d, J=9.0 Hz), 8.44 (1H, d, J=2.2 Hz)

Synthesis Example 21

A compound having

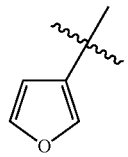 [SMILES: *c1ccoc1]

at R', which is obtained through the aforementioned step 12, was synthesized. The operation and the yield of each operation are shown below (compound 22).

yield: 43.6%, 95.0% ee (HPLC condition B), [α]$_D^{26}$+58.45 (c=0.08, CHCl$_3$)

$^1$HNMR (400 MHz, DMSO-d$_6$) δ: 1.80-1.92 (3H, m), 2.14-2.29 (1H, m), 2.32-2.49 (2H, m), 3.33-3.40 (1H, m), 3.51 (1H, d, J=15.6 Hz), 3.94 (3H, s), 3.99 (3H, s), 4.61 (1H, d, J=15.6 Hz), 4.77 (1H, d, J=9.8 Hz), 5.01 (1H, dd, J=2.0, 9.8 Hz), 7.00-7.04 (1H, m), 7.26 (1H, s), 7.45 (1H, dd, J=2.2, 9.0 Hz), 7.92-7.98 (1H, m), 8.11 (1H, s), 8.36 (1H, d, J=9.0 Hz), 8.62 (1H, d, J=2.2 Hz), 8.70-8.73 (1H, m)

Synthesis Example 22

A compound having

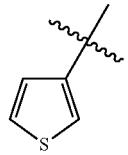 [SMILES: *c1ccsc1]

at R', which is obtained through the aforementioned step 12, was synthesized. The operation and the yield of each operation are shown below (compound 23).

yield: 42.1%, 99.5% ee (HPLC condition B), [α]$_D^{29}$+ 53.654 (c=0.1, CHCl$_3$)

$^1$HNMR (400 MHz, DMSO-d$_6$) δ: 1.76-1.92 (3H, m), 2.10-2.29 (1H, m), 2.35-2.49 (2H, m), 3.33-3.40 (1H, m), 3.52 (1H, d, J=15.9 Hz), 3.95 (3H, s), 3.99 (3H, s), 4.63 (1H, d, J=15.9 Hz), 4.76 (1H, d, J=9.8 Hz), 5.01 (1H, dd, J=2.0, 9.8

Hz), 7.28 (1H, s), 7.47 (1H, dd, J=2.2, 9.0 Hz), 7.69 (1H, dd, J=1.2, 5.1 Hz), 7.78 (1H, dd, J=3.0, 5.1 Hz), 8.12 (1H, s), 8.37 (1H, d, J=9.0 Hz), 8.64 (1H, d, J=2.2 Hz), 8.69 (1H, dd, J=1.2, 3.0 Hz)

Synthesis Example 23

A compound having

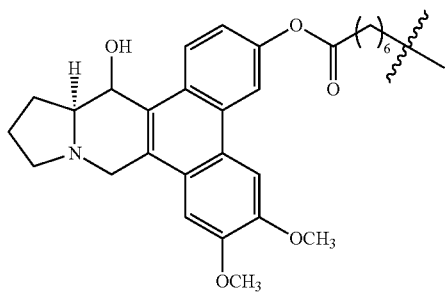

at R', which is obtained through the aforementioned step 12, was synthesized. The operation and the yield of each operation are shown below (compound 24).

yield: 42.8%

$^1$HNMR (400 MHz, DMSO-d$_6$) δ: 1.30-1.46 (4H, m), 1.47-1.57 (4H, m), 1.74-1.90 (6H, m), 2.11-2.25 (2H, m), 2.29-2.45 (4H, m), 2.62-2.75 (4H, m), 3.25-3.35 (2H, m), 3.47 (1H, d, J=15.6 Hz), 3.51 (1H, d, J=15.6 Hz), 3.93 (3H, s), 3.94 (3H, s), 3.99 (3H, s), 4.01 (3H, s), 4.57 (1H, d, J=15.6 Hz), 4.59 (1H, d, J=15.6 Hz), 4.71 (1H, d, J=10.2 Hz), 4.74 (1H, d, J=10.2 Hz), 4.84-4.91 (1H, m), 4.92-4.99 (1H, m), 7.22 (1H, s), 7.25 (1H, s), 7.31 (1H, dd, J=2.4, 9.0 Hz), 7.33 (1H, d, J=2.4, 9.0 Hz), 8.02 (1H, s), 8.07 (1H, s), 8.27 (1H, d, J=9.0 Hz), 8.31 (1H, d, J=9.0 Hz), 8.41 (1H, d, J=2.4 Hz), 8.44 (1H, d, J=2.4 Hz)

Synthesis Example 24

A compound having

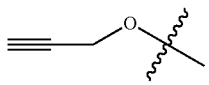

at R', which is obtained through the aforementioned step 12, was synthesized. The operation and the yield of each operation are shown below (compound 27).

yield: 75.1%, [α]$_D^{28}$+91.68

$^1$HNMR (400 MHz, DMSO-d$_6$) δ: 1.78-1.90 (3H, m), 2.12-2.27 (1H, m), 2.34-2.50 (2H, m), 3.27-3.34 (1H, m), 3.41 (1H, d, J=15.5 Hz), 3.75 (1H, t, J=2.4 Hz), 3.95 (3H, s), 4.01 (3H, s), 4.62 (1H, d, J=15.5 Hz), 4.76 (1H, d, J=9.8 Hz), 4.95 (2H, d, J=2.4 Hz), 4.98 (1H, dd, J=2.2, 9.8 Hz), 7.27 (1H, s), 7.46 (1H, dd, J=2.4, 9.0 Hz), 8.12 (1H, s), 8.35 (1H, d, J=9.0 Hz), 8.66 (1H, d, J=2.4 Hz)

Synthesis Example 25

A compound in which R' is CH$_3$CH$_2$O, which is obtained through the aforementioned step 12, was synthesized. The operation and the yield of each operation are shown below (compound 28).

yield: 52.3%, [α]$_D^{28}$+90.54

$^1$HNMR (400 MHz, DMSO-d$_6$) δ: 1.33 (3H, t, J=7.1 Hz), 1.79-1.89 (3H, m), 2.13-2.27 (1H, m), 2.30-2.48 (2H, m), 3.26-3.35 (1H, m), 3.50 (1H, d, J=15.6 Hz), 3.94 (3H,), 4.01 (3H, s), 4.30 (2H, q, J=7.1 Hz), 4.59 (1H, d, J=15.6 Hz), 4.76 (1H, d, J=9.8 Hz), 4.97 (1H, dd, J=2.2, 9.8 Hz), 7.25 (1H, s), 7.45 (1H, dd, J=2.4, 9.0 Hz), 8.11 (1H, s), 8.33 (1H, d, J=9.0 Hz), 8.62 (1H, d, J=2.4 Hz)

Synthesis Example 26

A compound having

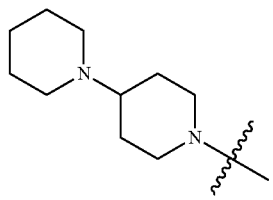 [SMILES: *N1CCC(N2CCCCC2)CC1]

at R', which is obtainable through the aforementioned step 12, was synthesized. The operation and the yield of each operation are shown below (compound 13).

yield: 93.0%, [α]$_D^{27}$+47.265 (c=0.1, CHCl$_3$)

$^1$HNMR (400 MHz, DMSO-d$_6$) δ: 1.30-1.64 (6H, m), 1.75-1.93 (7H, m), 2.10-2.26 (1H, m), 2.32-2.49 (2H, m), 2.75-2.90 (2H, m), 2.90-3.07 (2H, m), 3.10-3.22 (1H, m), 3.33-3.40 (1H, m), 3.50 (1H, d, J=15.6 Hz), 3.94 (3H, s), 4.00-4.27 (4H, m), 4.02 (3H, s), 4.59 (1H, d, J=15.6 Hz), 4.75 (1H, d, J=9.8 Hz), 4.97 (1H, dd, J=2.1, 9.8 Hz), 7.25 (1H, s), 7.30 (1H, dd, J=2.2, 9.0 Hz), 8.08 (1H, s), 8.33 (1H, d, J=9.0 Hz), 8.39 (1H, d, J=2.2 Hz)

Synthesis Example 26

A compound in which R" is CH$_3$, which is obtained through the aforementioned step 13, was synthesized. The operation and the yield of each operation are shown below (compound 8).

Step 13: Diacylation of Hydroxyl Groups of R$^2$ and R$^8$

In a 100 mL round-bottom flask, triethylamine (1.4 mL, 40 eq.), acetic anhydride (0.95 mL, 40 eq.), and dimethylaminopyridine (3 mg, 0.1 eq.) were added to a suspension of raw materials (90 mg, 0.25 mmol) in methylene chloride (15 mL) under an argon atmosphere while stirring with cooling on ice, followed by stirring for six hours. The disappearance of the raw materials was confirmed, and then the resulting reaction liquid was concentrated and purified through column chromatography (CHCl$_3$ only) to give 47 mg (41.9%) of a light yellow solid.

$^1$HNMR (400 MHz, DMSO-d$_6$) δ: 1.48-1.77 (2H, m), 1.86-2.12 (2H, m), 2.16 (3H, s), 2.41 (3H, s), 2.40-2.52 (1H, m), 2.67-2.79 (1H, m), 3.50-3.58 (1H, m), 3.66 (1H, d, J=15.38 Hz), 4.07 (3H, s), 4.12 (3H, s), 4.81 (1H, d, J=15.38 Hz), 6.73 (1H, brs), 7.23 (1H, s), 7.31 (1H, dd, J=2.20, 9.03 Hz), 7.89 (1H, s), 7.95 (1H, d, J=9.03 Hz), 8.21 (1H, d, J=2.20 Hz)

99% ee (HPLC analysis condition B), [α]$_D^{29}$+156.9 (c=0.12, CHCl$_3$)

The synthetic method for a compound resulting from reductive removal of a hydroxyl group of the compound obtained through the step 9 (a hydroxyl group at the position R$^8$ in the general formula (1) or (2)) will be described. The synthesis was carried out in accordance with the following steps 14 and 15.

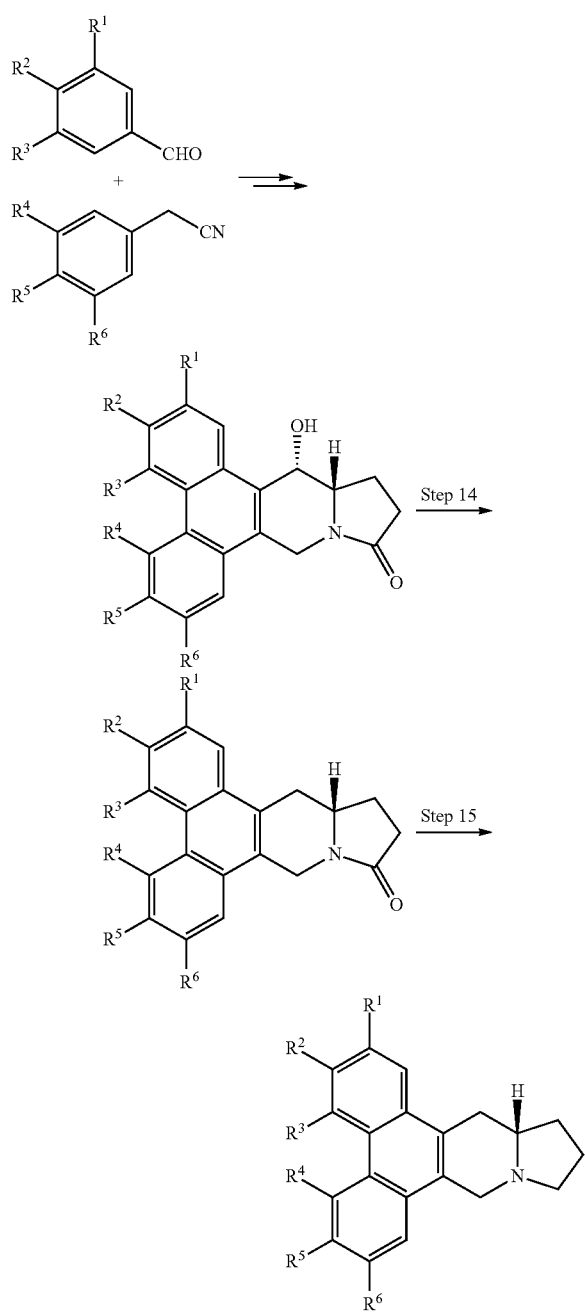

Reference Example 2

A compound having the following groups at $R^1$ to $R^6$ was synthesized as a precursor through the steps 15 and 16. The operation and the yield of each operation are shown below.

TABLE 10

| Compound 67 (as a precursor) | | | | | |
|---|---|---|---|---|---|
| $R^1$ | $R^2$ | $R^3$ | $R^4$ | $R^5$ | $R^6$ |
| H | OH | H | H | $OCH_3$ | $OCH_3$ |

Step 14: Reductive Removal of a Hydroxyl Group

In a round-bottom flask, 293 μL (2.31 mmol, 1.5 eq.) of a boron trifluoride•diethyl ether complex was added to a solution of 719 mg (1.54 mmol) of alcohol in 10 mL of methylene chloride at 0° C. under an argon atmosphere. After five minutes, 984 μL (6.16 mmol, 4.0 eq.) of triethylsilane was added. After four hours, the disappearance of the raw materials was confirmed, and a solution of chloroform-methanol=4:1 was added to give a complete solution. And then, the organic layer was separated and the aqueous layer was extracted with a solution of chloroform-methanol=4:1. The organic layer was combined and the resulting mixture was dried over magnesium sulfate. The solvent was then removed under reduced pressure. The residual product was purified by column chromatography (chloroform-methanol=50:1) to give 516 mg (740) of a white solid.

$[\alpha]_D^{30}$+185.34 (c=0.1, $CHCl_3$)

$^1$HNMR (400 MHz, $CDCl_3$) δ: 1.92-2.08 (1H, m), 2.48-2.68 (3H, m), 2.89 (1H, dd, J=11.0, 16.0 Hz), 3.58 (1H, dd, J=4.2, 16.0 Hz), 3.88-4.03 (1H, m), 4.06 (3H, s), 4.09 (3H, s), 4.57 (1H, d, J=17.5 Hz), 5.30 (2H, s), 5.33 (1H, d, J=17.5 Hz), 7.19 (1H, s), 7.31 (1H, dd, J=2.6, 9.2 Hz), 7.33-7.38 (1H, m), 7.38-7.46 (2H, m), 7.51-7.58 (2H, m), 7.85 (1H, s), 7.93 (1H, d, J=9.2 Hz), 7.99 (1H, d, J=2.6 Hz)

<Enantiomer>

$[\alpha]_D^{27}$-196.52 (c=0.1, $CHCl_3$)

Step 15: Reduction of Lactam (the Operation was Carried out in the Similar Manner as the Step 10)

yield: 74%, $[\alpha]_D^{30}$+90.40 (c=0.1, $CHCl_3$)

$^1$HNMR (400 MHz, DMSO-$d_6$) δ: 1.53-1.70 (1H, m), 1.75-1.94 (2H, m), 2.07-2.23 (1H, m), 2.26-2.44 (2H, m), 2.71-2.83 (1H, m), 3.26-3.42 (2H, m), 3.52 (1H, d, J=15.1 Hz), 3.93 (3H, s), 4.01 (3H, s), 4.55 (1H, d, J=15.1 Hz), 5.35 (2H, s), 7.20 (1H, s), 7.30 (1H, dd, J=2.4, 9.0 Hz), 7.32-7.37 (1H, m), 7.39-7.46 (2H, m), 7.52-7.61 (2H, m), 7.93 (1H, d, J=9.0 Hz), 8.17 (1H, d, J=2.4 Hz)

The specific optical rotation of the enantiomer $[\alpha]_D^{29}$-103.88 (c=0.1, $CHCl_3$)

Synthesis Example 27

A compound having the following groups at $R^1$ to $R^6$ was synthesized through steps 14 and 15, and by deprotection in step 11. The operation and the yield of each operation are shown below.

TABLE 11

| Compound 33 | | | | | |
|---|---|---|---|---|---|
| $R^1$ | $R^2$ | $R^3$ | $R^4$ | $R^5$ | $R^6$ |
| OH | H | H | H | $OCH_3$ | $OCH_3$ |

Step 14 yield: 78.3%

$^1$HNMR (400 MHz, $CDCl_3$) δ: 1.92-2.08 (1H, m), 2.48-2.68 (3H, m), 2.86 (1H, dd, J=10.5, 15.6 Hz), 3.47 (1H, dd, J=4.2, 15.6 Hz), 3.88-4.03 (1H, m), 4.06 (3H, s), 4.11 (3H, s), 4.60 (1H, d, J=17.5 Hz), 5.25 (2H, s), 5.37 (1H, d, J=17.5 Hz), 7.20 (1H, s), 7.31-7.46 (5H, m), 7.50-7.56 (2H, m), 7.95 (1H, s), 8.49 (1H, d, J=9.3 Hz)

Step 15 yield: 79.9%

$^1$HNMR (400 MHz, DMSO-$d_6$) δ: 1.53-1.70 (1H, m), 1.75-1.94 (2H, m), 2.07-2.23 (1H, m), 2.26-2.44 (2H, m), 2.76 (1H, dd, J=10.3, 15.6 Hz), 3.26-3.42 (2H, m), 3.55 (1H, d, J=15.4 Hz), 3.92 (3H, s), 3.98 (3H, s), 4.59 (1H, d, J=15.4 Hz), 5.29 (2H, s), 7.21 (1H, s), 7.29 (1H, dd, J=2.6, 9.2 Hz), 7.32-7.37 (1H, m), 7.39-7.46 (2H, m), 7.47 (1H, d, J=2.6 Hz), 7.51-7.57 (2H, m), 8.68 (1H, d, J=9.2 Hz)

Step 11: Deprotection of a Benzyl Group yield: 66.9%

$^1$HNMR (400 MHz, DMSO-d$_6$) δ: 1.52-1.68 (1H, m), 1.75-1.94 (2H, m), 2.07-2.23 (1H, m), 2.26-2.44 (2H, m), 2.63-2.75 (1H, m), 3.14-3.25 (1H, m), 3.26-3.42 (1H, m), 3.53 (1H, d, J=15.7 Hz), 3.90 (3H, s), 3.97 (3H, s), 4.56 (1H, d, J=15.7 Hz), 7.10 (1H, dd, J=2.4, 8.8 Hz), 7.18 (1H, s), 7.24 (1H, d, J=2.4 Hz), 8.02 (1H, s), 8.57 (1H, d, J=8.8 Hz), 9.6 (1H, s)

Synthesis Example 28

A compound having the following groups at R$^1$ to R$^6$ was synthesized through steps 14 and 15, and by deprotection in step 11. The operation and the yield of each operation are shown below.

TABLE 12

| Compound 40 | | | | | |
| --- | --- | --- | --- | --- | --- |
| R$^1$ | R$^2$ | R$^3$ | R$^4$ | R$^5$ | R$^6$ |
| H | H | OH | H | OCH$_3$ | OCH$_3$ |

Step 14 yield: 98.6%

$^1$HNMR (400 MHz, CDCl$_3$) δ: 1.97-2.12 (1H, m), 2.48-2.68 (3H, m), 2.85-3.00 (1H, m), 3.25 (3H, s), 3.50-3.61 (1H, m), 3.90-3.99 (1H, m), 4.02 (3H, s), 4.59 (1H, d, J=17.5 Hz), 5.22-5.30 (2H, m), 5.36 (1H, d, J=17.5 Hz), 7.20 (1H, s), 7.26-7.31 (1H, m), 7.38-7.46 (3H, m), 7.51-7.62 (2H, m), 7.59 (1H, dd, J=1.7, 7.8 Hz), 7.69 (1H, d, J=7.8 Hz), 9.16 (1H, s)

Steps 15 and 11 yield: 56.1%

$^1$HNMR (400 MHz, DMSO-d$_6$) δ: 1.58-1.68 (1H, m), 1.75-1.94 (2H, m), 2.07-2.23 (1H, m), 2.26-2.44 (2H, m), 2.71-2.83 (1H, m), 3.26-3.42 (2H, m), 3.56 (1H, d, J=15.1 Hz), 3.90 (3H, s), 3.93 (3H, s), 4.57 (1H, d, J=15.1 Hz), 7.08 (1H, d, J=7.8 Hz), 7.23 (1H, s), 7.36 (1H, t, J=7.8 Hz), 7.49 (1H, d, J=7.8 Hz), 9.45 (1H, s), 10.50 (1H, s)

Synthesis Example 29

A compound having the following groups at R$^1$ to R$^6$ was synthesized through steps 14 and 15. The operation and the yield of each operation are shown below.

TABLE 13

| Compound 32 | | | | | |
| --- | --- | --- | --- | --- | --- |
| R$^1$ | R$^2$ | R$^3$ | R$^4$ | R$^5$ | R$^6$ |
| H | H | H | H | OCH$_3$ | OCH$_3$ |

Step 14 yield: 85.8%

$^1$HNMR (400 MHz, CDCl$_3$) δ: 1.96-2.10 (1H, m), 2.48-2.68 (3H, m), 2.92 (1H, dd, J=10.7, 16.1 Hz), 3.61 (1H, dd, J=4.3, 16.1 Hz), 3.88-4.03 (1H, m), 4.07 (3H, s), 4.13 (3H, s), 4.61 (1H, d, J=17.7 Hz), 5.38 (1H, d, J=17.7 Hz), 7.23 (1H, s), 7.56-7.67 (2H, m), 7.98-8.04 (1H, m), 8.05 (1H, s), 8.53-8.61 (1H, m)

Step 15 yield: 84.6%

$^1$HNMR (400 MHz, DMSO-d$_6$) δ: 1.58-1.70 (1H, m), 1.75-1.94 (2H, m), 2.07-2.23 (1H, m), 2.31-2.44 (2H, m), 2.81 (1H, dd, J=10.5, 15.9 Hz), 3.26-3.44 (2H, m), 3.57 (1H, d, J=15.5 Hz), 3.94 (3H, s), 4.00 (3H, s), 4.60 (1H, d, J=15.5 Hz), 7.24 (1H, s), 7.53-7.64 (2H, m), 7.97-8.04 (1H, m), 8.16 (1H, s), 8.72-8.78 (1H, m)

Synthesis Example 30

A compound having the following groups at R$^1$ to R$^6$ was synthesized through steps 14 and 15. The operation and the yield of each operation are shown below.

TABLE 14

| Compound 41 | | | | | |
| --- | --- | --- | --- | --- | --- |
| R$^1$ | R$^2$ | R$^3$ | R$^4$ | R$^5$ | R$^6$ |
| H | CH$_3$CH$_2$ | H | H | OCH$_3$ | OCH$_3$ |

Step 14 yield: 89.0%

$^1$HNMR (400 MHz, CDCl$_3$) δ: 1.39 (3H, t, J=7.6 Hz), 1.96-2.10 (1H, m), 2.48-2.68 (3H, m), 2.89 (1H, dd, J=11.0, 15.9 Hz), 2.92 (2H, q, J=7.6 Hz), 3.58 (1H, dd, J=4.3, 15.9 Hz), 3.88-4.03 (1H, m), 4.06 (3H, s), 4.14 (3H, s), 4.58 (1H, d, J=17.3 Hz), 5.34 (1H, d, J=17.3 Hz), 7.20 (1H, s), 7.46 (1H, dd, J=1.7, 8.5 Hz), 7.93 (1H, d, J=8.5 Hz), 8.04 (1H, s), 8.33 (1H, d, J=1.7 Hz)

Step 15 yield: 71.3%

$^1$HNMR (400 MHz, DMSO-d$_6$) δ: 1.32 (3H, t, J=7.7 Hz), 1.58-1.70 (1H, m), 1.75-1.94 (2H, m), 2.07-2.23 (1H, m), 2.31-2.44 (2H, m), 2.86 (2H, q, J=7.7 Hz), 3.26-3.42 (2H, m), 3.55 (1H, d, J=15.1 Hz), 3.93 (3H, s), 4.01 (3H, s), 4.58 (1H, d, J=15.1 Hz), 7.22 (1H, s), 7.45 (1H, d, J=8.3 Hz), 7.92 (1H, d, J=8.30 Hz), 8.15 (1H, s), 8.54 (1H, s)

Synthesis Example 31

A compound having the following groups at R$^1$ to R$^6$ was synthesized through steps 14 and 15. The operation and the yield of each operation are shown below.

TABLE 15

| Compound 31 | | | | | |
| --- | --- | --- | --- | --- | --- |
| R$^1$ | R$^2$ | R$^3$ | R$^4$ | R$^5$ | R$^6$ |
| H | F | H | H | OCH$_3$ | OCH$_3$ |

Step 14 yield: 85.0%

$^1$HNMR (400 MHz, CDCl$_3$) δ: 1.96-2.10 (1H, m), 2.48-2.68 (3H, m), 2.90 (1H, dd, J=10.7, 15.9 Hz), 3.56 (1H, dd, J=4.3, 15.9 Hz), 3.88-4.03 (1H, m), 4.07 (3H, s), 4.13 (3H, s), 4.58 (1H, d, J=17.3 Hz), 5.35 (1H, d, J=17.3 Hz), 7.21 (1H, s), 7.28-7.37 (1H, m), 7.87 (1H, s), 7.95-8.03 (1H, m), 8.12-8.20 (1H, m)

Step 15 yield: 54.9%

$^1$HNMR (400 MHz, DMSO-d$_6$) δ: 1.53-1.70 (1H, m), 1.75-1.94 (2H, m), 2.07-2.23 (1H, m), 2.31-2.44 (2H, m), 2.71-2.83 (1H, m), 3.26-3.42 (2H, m), 3.54 (1H, d, J=15.4

Hz), 3.94 (3H, s), 4.00 (3H, s), 4.58 (1H, d, J=15.4 Hz), 7.23 (1H, s), 7.43 (1H, ddd, J=2.7, 8.8, 11.5 Hz), 8.05 (1H, dd, J=6.1, 8.8 Hz), 8.11 (1H, s), 8.59 (1H, dd, J=2.7, 11.5 Hz)

Synthesis Example 32

A compound having the following groups at $R^1$ to $R^6$ was synthesized. The operation and the yield of each operation are shown below.

TABLE 16

| colspan="6" | Compound 42 |
| --- | --- | --- | --- | --- | --- |
| $R^1$ | $R^2$ | $R^3$ | $R^4$ | $R^5$ | $R^6$ |
| H |  | H | H | $OCH_3$ | $OCH_3$ |

The synthetic pathway of the above compound (compound 42) is shown below.

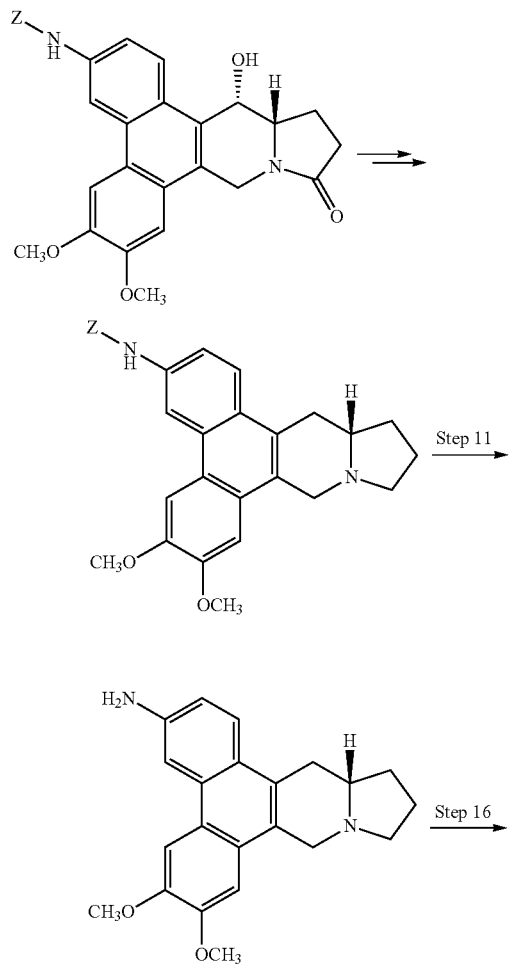

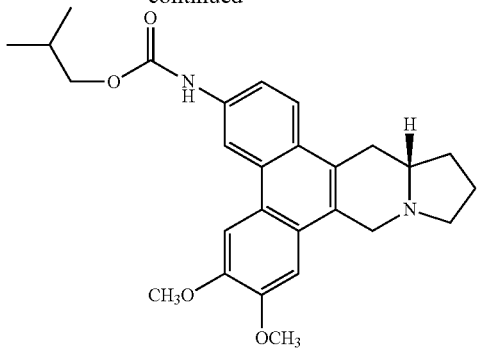

Benzyl carbamate obtained in accordance with the steps 14 and 15 was hydrogenated under similar conditions as those of the step 11, whereby it was converted into unsubstituted amine. The amino group of the unsubstituted amine was converted to isobutyl carbamate to give a target compound.

Step 14 yield: 72.7%

$^1$HNMR (400 MHz, CDCl$_3$) δ: 1.92-2.08 (1H, m), 2.48-2.68 (3H, m), 2.86 (1H, dd, J=10.6, 15.7 Hz), 3.54 (1H, dd, J=4.5, 15.7 Hz), 3.88-4.03 (1H, m), 4.06 (3H, s), 4.11 (3H, s), 4.56 (1H, d, J=17.5 Hz), 5.29 (2H, s), 5.32 (1H, d, J=17.5 Hz), 6.95-7.03 (1H, m), 7.17 (1H, s), 7.33-7.48 (5H, m), 7.52-7.61 (1H, m), 7.91 (1H, s), 7.93-7.98 (1H, m), 8.62-8.70 (1H, m)

Step 15

(compound 54)

yield: 76.3%

$^1$HNMR (400 MHz, DMSO-d$_6$) δ: 1.53-1.70 (1H, m), 1.75-1.94 (2H, m), 2.07-2.23 (1H, m), 2.33-2.44 (2H, m), 2.71-2.83 (1H, m), 3.26-3.42 (2H, m), 3.53 (1H, d, J=15.4 Hz), 3.94 (3H, s), 3.96 (3H, s), 4.57 (1H, d, J=15.4 Hz), 5.22 (2H, s), 7.22 (1H, s), 7.32-7.39 (1H, m), 7.36-7.43 (2H, m), 7.44-7.49 (2H, m), 7.67-7.77 (1H, m), 7.88 (1H, s), 7.94 (1H, d, J=9.0 Hz), 8.70-8.77 (1H, m), 9.98 (1H, s)

Step 11 yield: quant $^1$HNMR (400 MHz, DMSO-d$_6$) δ: 1.53-1.70 (1H, m), 1.75-1.94 (2H, m), 2.07-2.23 (1H, m), 2.26-2.44 (2H, m), 2.64-2.78 (1H, m), 3.23-3.42 (2H, m), 3.47 (1H, d, J=15.0 Hz), 3.91 (3H, s), 3.96 (3H, s), 4.49 (1H, d, J=15.0 Hz), 5.31 (2H, s), 6.90-6.97 (1H, m), 7.13 (1H, s), 7.67-7.73 (2H, m), 7.86 (1H, s)

Step 16: Carbamoylation of an Amino Group

Under an argon atmosphere at 0° C., 109 μL (0.78 mmol, 3.0 eq.) of triethylamine and 101 μL (0.78 mmol, 3.0 eq.) of isobutyl chloroformate were added to a solution of 90 mg (0.26 mmol) of raw materials in 10 mL of methylene chloride. After three hours, the disappearance of the raw materials was confirmed, and the resulting reaction liquid was directly purified through column chromatography (chloroform:methanol=200:1) to give 49 mg (42.3%) of a white solid.

$^1$HNMR (400 MHz, DMSO-d$_6$) δ: 0.96 (6H, d, J=6.6 Hz), 1.56-1.68 (1H, m), 1.75-1.90 (2H, m), 1.96 (1H, nonet, J=6.6 Hz), 2.10-2.23 (1H, m), 2.32-2.56 (2H, m), 2.71-2.83 (1H, m), 3.20-3.42 (2H, m), 3.53 (1H, d, J=15.5 Hz), 3.93 (2H, d, J=6.6 Hz), 3.94 (3H, s), 3.98 (3H, s), 4.57 (1H, d, J=15.5 Hz), 7.22 (1H, s), 7.68-7.78 (1H, m), 7.89 (1H, s), 7.93 (1H, d, J=9.0 Hz), 8.67-8.86 (1H, m), 9.80 (1H, s)

A phenolic hydroxyl group of a compound in which a hydroxyl group at $R^8$ has been removed can also be acylated by applying the following step 12-2.

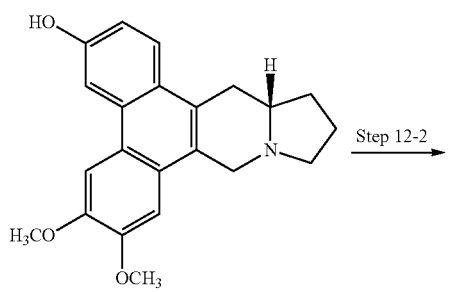

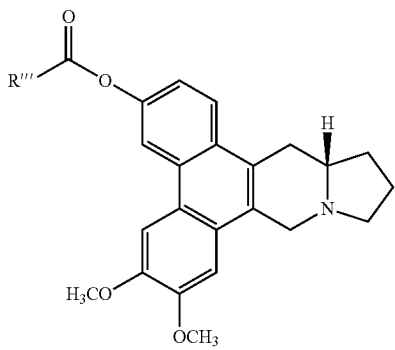

Synthesis Example 33

A compound having Ac at R''', which is obtained through the aforementioned step 12-2, was synthesized. The operation and the yield of each operation are shown below (compound 34).

yield: 59.80

$^1$HNMR (400 MHz, DMSO-$d_6$) δ: 1.58-1.70 (1H, m), 1.75-1.94 (2H, m), 2.07-2.23 (1H, m), 2.31-2.44 (2H, m), 2.35 (3H, s), 2.81 (1H, dd, J=11.2, 15.4), 3.27-3.42 (2H, m), 3.56 (1H, d, J=15.3 Hz), 3.94 (3H, s), 4.00 (3H, s), 4.60 (1H, d, J=15.3 Hz), 7.24 (1H, s), 7.35 (1H, dd, J=1.0, 9.0 Hz), 8.03 (1H, d, J=9.0 Hz), 8.07 (1H, s), 8.49 (1H, s)

Synthesis Example 34

A compound having (CH$_3$)$_3$C at R''', which is obtained through the aforementioned step 12-2, was synthesized. The operation and the yield of each operation are shown below (compound 35).

yield: 80.8%

$^1$HNMR (400 MHz, DMSO-$d_6$) δ: 1.39 (9H, s), 1.58-1.70 (1H, m), 1.75-1.94 (2H, m), 2.07-2.23 (1H, m), 2.31-2.44 (2H, m), 2.76-2.88 (1H, m), 3.27-3.42 (2H, m), 3.56 (1H, d, J=15.3 Hz), 3.95 (3H, s), 4.01 (3H, s), 4.60 (1H, d, J=15.3 Hz), 7.24 (1H, s), 7.29 (1H, dd, J=2.2, 9.0 Hz), 8.04 (1H, d, J=9.0 Hz), 8.08 (1H, s), 8.41 (1H, d, J=2.2)

Synthesis Example 35

A compound having

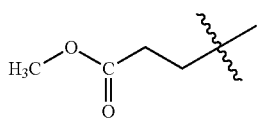 [SMILES: *CCC(=O)OC]

at R''', which is obtained through the aforementioned step 12-2, was synthesized. The operation and the yield of each operation are shown below (compound 36).

yield: 85.7%

$^1$HNMR (400 MHz, DMSO-$d_6$) δ: 1.58-1.70 (1H, m), 1.75-1.94 (2H, m), 2.07-2.23 (1H, m), 2.31-2.44 (2H, m), 2.74 (2H, t, J=6.7 Hz), 2.76-2.88 (1H, m), 2.94 (2H, t, J=6.7 Hz), 3.27-3.42 (2H, m), 3.56 (1H, d, J=15.0 Hz), 3.65 (3H, s), 3.95 (3H, s), 4.00 (3H, s), 4.60 (1H, d, J=15.0 Hz), 7.24 (1H, s), 7.32 (1H, dd, J=2.3, 8.9 Hz), 8.04 (1H, d, J=8.9 Hz), 8.06 (1H, s), 8.46 (1H, d, J=2.3)

Synthesis Example 36

A compound having CH$_3$O at R''', which is obtained through the aforementioned step 12-2, was synthesized. The operation and the yield of each operation are shown below (compound 37).

yield: 45.6%

$^1$HNMR (400 MHz, DMSO-$d_6$) δ: 1.58-1.70 (1H, m), 1.75-1.94 (2H, m), 2.07-2.23 (1H, m), 2.31-2.44 (2H, m), 2.76-2.88 (1H, m), 3.27-3.42 (2H, m), 3.56 (1H, d, J=15.9 Hz), 3.88 (3H, s), 3.94 (3H, s), 4.00 (3H, s), 4.60 (1H, d, J=15.9 Hz), 7.24 (1H, s), 7.45 (1H, dd, J=2.4, 9.0 Hz), 8.05 (1H, d, J=9.0 Hz), 8.11 (1H, s), 8.64 (1H, d, J=2.4)

Synthesis Example 37

A compound having

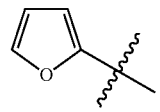 [SMILES: *c1ccco1]

at R''', which is obtained through the aforementioned step 12-2, was synthesized. The operation and the yield of each operation are shown below (compound 38).

yield: 35.6%

$^1$HNMR (400 MHz, DMSO-$d_6$) δ: 1.58-1.70 (1H, m), 1.75-1.94 (2H, m), 2.12-2.23 (1H, m), 2.31-2.44 (2H, m), 2.76-2.88 (1H, m), 3.27-3.42 (2H, m), 3.58 (1H, d, J=15.5 Hz), 3.95 (3H, s), 3.98 (3H, s), 4.62 (1H, d, J=15.5 Hz), 6.84 (1H, dd, J=1.3, 3.7 Hz), 7.25 (1H, s), 7.48 (1H, dd, J=2.3, 8.9 Hz), 7.65 (1H, d, J=3.7 Hz), 8.08 (1H, d, J=8.9 Hz), 8.12 (1H, s), 8.14 (1H, d, J=1.3 Hz), 8.68 (1H, d, J=2.3)

Synthesis Example 38

A compound having

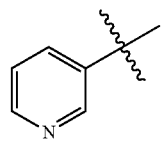 [SMILES: *c1cccnc1]

at R''', which is obtained through the aforementioned step 12-2, was synthesized. The operation and the yield of each operation are shown below (compound 39).

yield: 60.5%

$^1$HNMR (400 MHz, DMSO-$d_6$) δ: 1.58-1.70 (1H, m), 1.75-1.94 (2H, m), 2.12-2.23 (1H, m), 2.31-2.44 (2H, m), 2.76-2.88 (1H, m), 3.27-3.42 (2H, m), 3.58 (1H, d, J=14.8 Hz), 3.95 (3H, s), 3.98 (3H, s), 4.61 (1H, d, J=14.8 Hz), 7.25 (1H, s), 7.54 (1H, dd, J=1.3, 8.9 Hz), 7.69 (1H, dd, J=4.9, 8.1 Hz), 8.09 (1H, d, J=8.9 Hz), 8.11 (1H, s), 8.56 (1H, d, J=8.1 Hz), 8.71 (1H, d, J=1.3), 8.93 (1H, d, J=4.9 Hz), 9.36 (1H, t, J=1.0 Hz)

Synthesis Example 39

A compound having CH₃CH₂CH₂CH₂ at R''', which is obtained through the aforementioned step 12-2, was synthesized. The operation and the yield of each operation are shown below (compound 49).

yield: 69.2%

¹HNMR (400 MHz, DMSO-d₆) δ: 0.96 (3H, t, J=7.1 Hz), 1.39-1.52 (2H, m), 1.58-1.77 (3H, m), 1.78-1.95 (2H, m), 2.12-2.24 (1H, m), 2.30-2.45 (2H, m), 2.68 (2H, t, J=7.1 Hz), 2.76-2.88 (1H, m), 3.27-3.42 (2H, m), 3.57 (1H, d, J=15.7 Hz), 3.96 (3H, s), 4.01 (3H, s), 4.61 (1H, d, J=15.7 Hz), 7.25 (1H, s), 7.34 (1H, dd, J=1.6, 8.7 Hz), 8.04 (1H, d, J=8.7 Hz), 8.08 (1H, s), 8.47 (1H, d, J=1.6 Hz)

Synthesis Example 40

A compound having CH₃CH₂CH₂ at R''', which is obtained through the aforementioned step 12-2, was synthesized. The operation and the yield of each operation are shown below (compound 50).

yield: 62.0%

¹HNMR (400 MHz, DMSO-d₆) δ: 0.96 (3H, t, J=7.4 Hz), 1.58-1.77 (3H, m), 1.78-1.95 (2H, m), 2.12-2.24 (1H, m), 2.30-2.45 (2H, m), 2.61 (2H, t, J=7.4 Hz), 2.76-2.88 (1H, m), 3.27-3.42 (2H, m), 3.57 (1H, d, J=15.7 Hz), 3.96 (3H, s), 4.01 (3H, s), 4.61 (1H, d, J=15.7 Hz), 7.25 (1H, s), 7.34 (1H, dd, J=1.6, 8.7 Hz), 8.04 (1H, d, J=8.7 Hz), 8.08 (1H, s), 8.47 (1H, d, J=1.6 Hz)

Synthesis Example 41

A compound having CH₃CH₂₂ at R''', which is obtained through the aforementioned step 12-2, was synthesized. The operation and the yield of each operation are shown below (compound 51).

yield: 74.0%

¹HNMR (400 MHz, DMSO-d₆) δ: 1.20 (3H, t, J=7.4 Hz), 1.58-1.70 (1H, m), 1.75-1.94 (2H, m), 2.07-2.23 (1H, m), 2.31-2.44 (2H, m), 2.76-2.88 (1H, m), 2.70 (2H, q, J=7.4 Hz), 3.27-3.42 (2H, m), 3.57 (1H, d, J=15.7 Hz), 3.96 (3H, s), 4.01 (3H, s), 4.61 (1H, d, J=15.7 Hz), 7.25 (1H, s), 7.34 (1H, dd, J=1.6, 8.7 Hz), 8.04 (1H, d, J=8.7 Hz), 8.08 (1H, s), 8.47 (1H, d, J=1.6 Hz)

A compound having an amino group at R² can also be synthesized by a Pd-catalyzed aromatic amination reaction. Bromide which serves as a substrate in the palladium-catalyzed aromatic amination reaction was synthesized through the aforementioned steps 1 to 9 and 14.

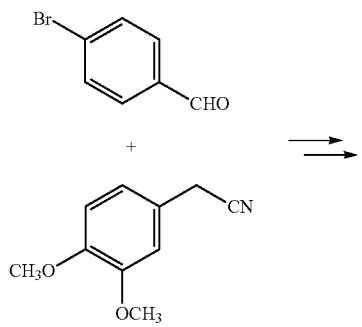

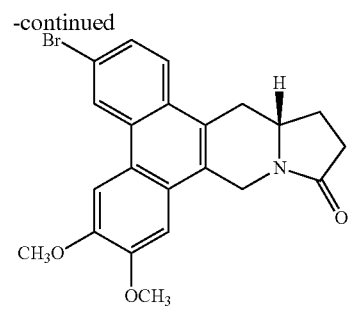

Step 1
yield: 95%
¹HNMR (400 MHz, CDCl₃) δ: 3.93 (3H, s), 3.96 (3H, s), 6.92 (1H, d, J=8.4 Hz), 7.14 (1H, d, J=2.3 Hz), 7.26 (1H, dd, J=2.3, 8.4 Hz), 7.36 (1H, s), 7.56-7.63 (2H, m), 7.70-7.77 (2H, m)

Step 2
yield: 94%
¹HNMR (400 MHz, CDCl₃) δ: 4.11 (3H, s), 4.16 (3H, s), 7.59 (1H, s), 7.70 (1H, dd, J=1.6, 8.6 Hz), 7.78 (1H, d, J=8.6 Hz), 7.88 (1H, s), 8.11 (1H, s), 8.65 (1H, d, J=1.6 Hz)

Step 3
yield: quant.
¹HNMR (400 MHz, CDCl₃) δ: 4.12 (3H, s), 4.15 (3H, s), 7.71 (1H, dd, J=1.8, 8.4 Hz), 7.89 (1H, d, J=8.4 Hz), 7.89 (1H, s), 8.12 (1H, s), 8.66 (1H, d, J=1.8 Hz), 8.95 (1H, s), 10.31 (1H, s)

Step 4
yield: 69%
¹HNMR (400 MHz, CDCl₃) δ: 4.07 (3H, s), 4.14 (3H, s), 5.14 (2H, s), 7.53 (1H, s), 7.73 (1H, dd, J=1.7, 8.4 Hz), 7.65 (1H, s), 7.73 (1H, d, J=8.4 Hz), 7.91 (1H, s), 8.62 (1H, d, J=1.7 Hz)

Steps 5 and 6
yield: 70%
¹HNMR (400 MHz, CDCl₃) δ: 1.17 (3H, d, J=6.2 Hz), 1.18 (3H, d, J=6.2 Hz), 1.91-2.02 (1H, m), 2.06-2.20 (1H, m), 2.32-2.44 (1H, m), 2.54-2.64 (1H, m), 3.69-3.75 (1H, m), 4.05 (3H, s), 4.13 (3H, s), 4.37 (1H, d, J=14.6 Hz), 4.99 (1H, heptet, J=6.2 Hz), 5.58 (1H, d, J=14.6 Hz), 7.44 (1H, s), 7.61 (1H, dd, J=1.9, 8.6 Hz), 7.64 (1H, s), 7.67 (1H, d, J=86 Hz), 7.90 (1H, s), 8.62 (1H, d, J=1.9 Hz)

Step 7
yield: 87%
¹HNMR (400 MHz, DMSO-d₆) δ: 1.83-1.91 (1H, m), 2.08-2.23 (1H, m), 2.26-2.44 (2H, m), 3.67-3.74 (1H, m), 3.88 (3H, s), 4.03 (3H, s), 4.29 (1H, d, J=14.5 Hz), 5.37 (1H, d, J=14.5 Hz), 7.55 (1H, s), 7.56 (1H, s), 7.68 (1H, dd, J=2.0, 8.6 Hz), 7.87 (1H, d, J=8.6 Hz), 8.19 (1H, s), 9.01 (1H, d, J=2.0 Hz)

Step 8
yield: 82%
¹HNMR (400 MHz, CDCl₃) δ: 2.48-2.72 (4H, m), 4.10 (3H, s), 4.18 (3H, s), 4.41-4.48 (1H, m), 4.69 (1H, d, J=18.1 Hz), 5.74 (1H, d, J=18.1 Hz), 7.34 (1H, s), 7.72 (1H, dd, J=1.8, 9.3 Hz), 7.89 (1H, s), 8.62 (1H, d, J=1.8 Hz), 9.29 (1H, d, J=9.3 Hz)

Steps 9 and 14
yield: 79%
¹HNMR (400 MHz, CDCl₃) δ: 1.97-2.12 (1H, m), 2.52-2.65 (3H, m), 2.82-2.94 (1H, m), 3.49-3.58 (1H, m), 3.90-4.02 (1H, m), 4.07 (3H, s), 4.14 (3H, s), 4.56 (1H, d, J=17.6

Hz), 5.34 (1H, d, J=17.6 Hz), 7.21 (1H, s), 7.67 (1H, dd, J=2.0, 8.8 Hz), 7.86 (1H, d, J=8.8 Hz), 7.91 (1H, s), 8.66 (1H, d, J=2.0 Hz)

As shown above, a compound having a bromine atom at $R^2$ was synthesized. Using this compound as a substrate, an amino group was introduced to $R^2$ by a palladium-catalyzed aromatic amination reaction (step 17).

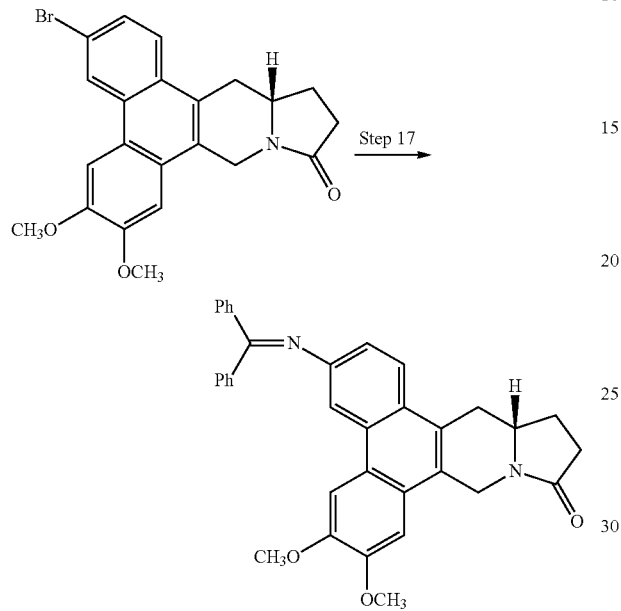

Step 17: Palladium-catalyzed amination reaction on aromatic bromide

Under an argon atmosphere at room temperature, 110 mg (0.12 mmol, 0.25 eq.) of trisdibenzylideneacetone dipalladium, 143 mg (0.18 mmol, 0.38 eq.) of di-tert-butylbiphenyl phosphine, 200 mg (0.47 mmol) of raw materials, and toluene (3 mL) were added to a round-bottom flask. Subsequently, 60 mg (0.62 mmol, 1.3 eq.) of sodium tert-butoxide and 175 µl (1.05 mmol, 2.2 eq.) of benzophenoneimine were added at 80° C., followed by stirring while heating. After 90 minutes, the disappearance of the raw materials was confirmed, and the resulting reaction liquid was cooled on ice. Purified water was then added to quench the reaction, and a solution of chloroform:methanol=4:1 was added to dissolve a solid. The organic layer was separated and the aqueous layer was extracted with a solution of chloroform:methanol=4:1. The organic layer was combined and dried over magnesium sulfate. The solvent was then removed under reduced pressure and the residual product was purified by column chromatography (chloroform:methanol=50:1) to give 270 mg (quant.) of a yellow solid.

$^1$HNMR (400 MHz, CDCl$_3$) δ: 1.96-2.10 (1H, m), 2.50-2.66 (3H, m), 2.81-2.93 (1H, m), 3.47-3.58 (1H, m), 3.89-4.02 (1H, m), 4.07 (3H, s), 4.14 (3H, s), 4.55 (1H, d, J=17.4 Hz), 5.33 (1H, d, J=17.4 Hz), 7.20 (1H, s), 7.36-7.64 (10H, m), 7.66 (1H, dd, J=2.0, 8.8 Hz), 7.85 (1H, d, J=8.8 Hz), 7.91 (1H, s), 8.65 (1H, d, J=2.0 Hz)

Using the imine obtained by the palladium-catalyzed reaction as a substrate, various derivatives were synthesized through steps 18, 10, and 16.

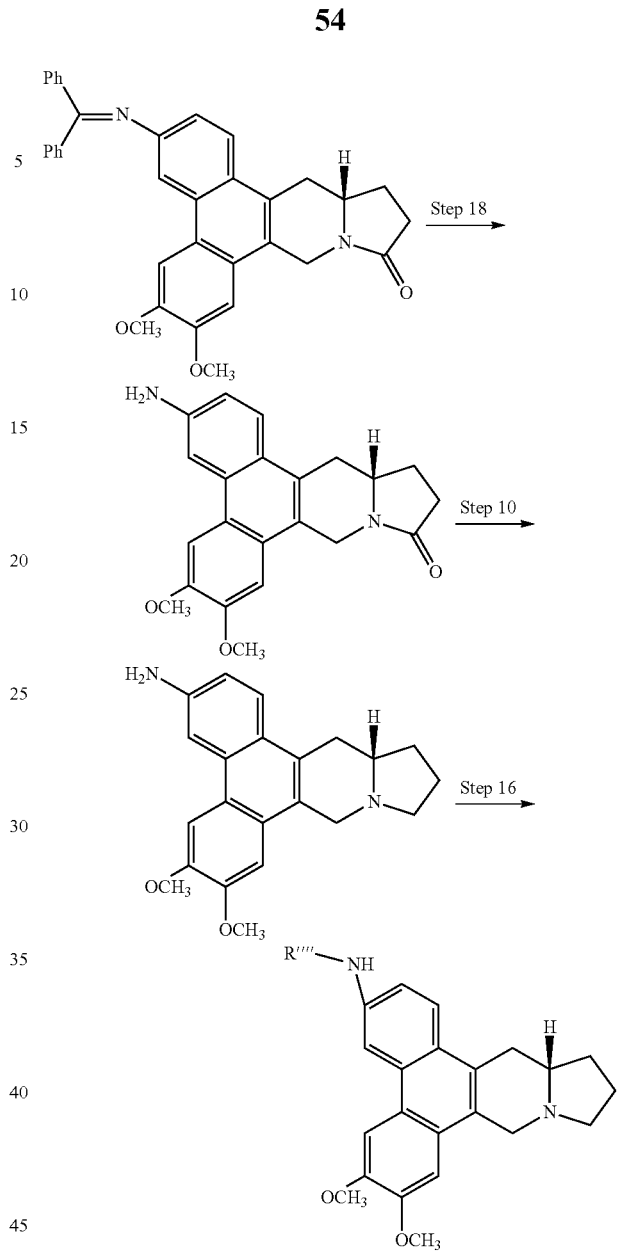

Synthesis Example 42

Step 18: Hydrolysis of Imine

While stirring at room temperature, 10 mL of 1 M hydrochloric acid was added to 270 mg (0.51 mmol) of raw materials, and then 20 mL of 1,4-dioxane was added to prepare a solution, followed by stirring. After 4 hours, the disappearance of the raw materials was confirmed, and saturated sodium bicarbonate water was added to the resulting reaction liquid to make it weakly basic. A solution of chloroform:methanol=4:1 was then added to separate the reaction liquid into two layers. The organic layer was separated and the aqueous layer was extracted with a solution of chloroform:methanol=4:1. The organic layer was combined and then dried over anhydrous magnesium sulfate. The solvent was removed under reduced pressure and then purified by column chromatography (chloroform:methanol=50:1) to give 69 mg (yield 37%) of a light yellow solid.

¹HNMR (400 MHz, CDCl₃) δ: 1.95-2.07 (1H, m), 2.49-2.63 (3H, m), 2.78-2.90 (1H, m), 3.46-3.58 (1H, m), 3.88-4.03 (3H, m), 4.06 (3H, s), 4.11 (3H, s), 4.54 (1H, d, J=16.6 Hz), 5.30 (1H, d, J=16.6 Hz), 7.01 (1H, dd, J=2.2, 8.8 Hz), 7.16 (1H, s), 7.74 (1H, d, J=2.2 Hz), 7.82 (1H, d, J=8.8 Hz), 7.89 (1H, s)

Step 10
(compound 54)
yield: 78%
¹HNMR (400 MHz, DMSO-d₆) δ: 1.50-1.70 (1H, m), 1.73-1.92 (2H, m), 2.07-2.21 (1H, m), 2.27-2.43 (2H, m), 2.64-2.77 (1H, m), 3.22-3.38 (2H, m), 3.48 (1H, d, J=14.7 Hz), 3.91 (3H, s), 3.96 (3H, s), 4.50 (1H, d, J=14.7 Hz), 5.32 (2H, brs), 6.92 (1H, dd, J=2.1, 8.9 Hz), 7.13 (1H, s), 7.69 (1H, d, J=2.1 Hz), 7.69 (1H, d, J=8.9 Hz), 7.86 (1H, s)

The amino group can be substituted by various substituents by reacting the resulting compound having an unsubstituted amino group at R² with various acid chloride in accordance with the step 16. The operation and the yield of each operation are shown below for each of the substituents used (R"").

Step 16
R""=CF₃CO (compound 60)
yield: 45.4%
¹HNMR (400 MHz, DMSO-d₆) δ: 1.58-1.71 (1H, m), 1.78-1.94 (2H, m), 2.12-2.23 (1H, m), 2.32-2.45 (2H, m), 2.76-2.88 (1H, m), 3.28-3.45 (2H, m), 3.57 (1H, d, J=15.3 Hz), 3.96 (3H, s), 4.01 (3H, s), 4.61 (1H, d, J=15.3 Hz), 7.27 (1H, s), 7.94 (1H, dd, J=1.8, 9.0 Hz), 7.96 (1H, s), 8.06 (1H, d, J=9.0 Hz), 8.89 (1H, d, J=1.9 Hz), 11.48 (1H, brs)

R""=CH₃SO₂ (compound 63)
yield: 59.6%
¹HNMR (400 MHz, DMSO-d₆) δ: 1.56-1.71 (1H, m), 1.78-1.96 (2H, m), 2.10-2.25 (1H, m), 2.30-2.45 (2H, m), 2.72-2.85 (1H, m), 3.05 (3H, s), 3.35-3.45 (2H, m), 3.56 (1H, d, J=16.3 Hz), 3.95 (3H, s), 3.99 (3H, s), 4.60 (1H, d, J=16.3 Hz), 7.24 (1H, s), 7.51 (1H, d, J=9.0 Hz), 7.91 (1H, s), 8.00 (1H, d, J=9.0 Hz), 8.41 (1H, s), 9.88 (1H, brs)

R""=CH₃OCO (compound 62)
yield: 19.9%
¹HNMR (400 MHz, DMSO-d₆) δ: 1.56-1.71 (1H, m), 1.76-1.94 (2H, m), 2.12-2.23 (1H, m), 2.32-2.47 (2H, m), 2.71-2.84 (1H, m), 3.28-3.45 (2H, m), 3.55 (1H, d, J=15.5 Hz), 3.73 (3H, s), 3.95 (3H, s), 3.99 (3H, s), 4.59 (1H, d, J=15.5 Hz), 7.23 (1H, s), 7.71 (1H, dd, J=1.7, 8.8 Hz), 7.90 (1H, s), 7.95 (1H, d, J=8.8 Hz), 8.74 (1H, d, J=1.9 Hz), 9.85 (1H, brs)

R""=HCO (compound 64)
yield: 58.9%
¹HNMR (400 MHz, DMSO-d₆) δ: 1.60-1.78 (1H, m), 1.82-2.00 (2H, m), 2.15-2.33 (1H, m), 2.40-2.52 (2H, m), 2.78-2.97 (1H, m), 3.38-3.53 (2H, m), 3.61-3.81 (1H, m), 3.92-4.05 (6H, m), 4.50-4.81 (1H, m), 7.20-8.16 (4H, m), 8.37-8.56 (1H, m), 8.85-9.16 (1H, m), 10.27-10.48 (1H, m)

R""=C₆H₅CO (compound 65)
yield: 46.5%
¹HNMR (400 MHz, DMSO-d₆) δ: 1.56-1.74 (1H, m), 1.76-1.97 (2H, m), 2.12-2.23 (1H, m), 2.32-2.47 (2H, m), 2.75-2.89 (1H, m), 3.28-3.45 (2H, m), 3.58 (1H, d, J=15.5 Hz), 3.96 (3H, s), 4.02 (3H, s), 4.61 (1H, d, J=15.5 Hz), 7.26 (1H, s), 7.54-7.67 (3H, m), 7.96-8.16 (5H, m), 9.02 (1H, s), 10.50 (1H, s)

R""=CH₃CO (compound 56)
yield: 86%
¹HNMR (400 MHz, DMSO-d₆) δ: 1.55-1.70 (1H, m), 1.75-1.94 (2H, m), 2.07-2.23 (1H, m), 2.12 (3H, s), 2.30-2.45 (2H, m), 2.70-2.84 (1H, m), 3.26-3.44 (2H, m), 3.55 (1H, d, J=15.4 Hz), 3.94 (3H, s), 3.98 (3H, s), 4.58 (1H, d, J=15.4 Hz), 7.23 (1H, s), 7.83 (1H, dd, J=1.8, 8.9 Hz), 7.89 (1H, s), 7.94 (1H, d, J=8.9 Hz), 8.81 (1H, d, J=1.8 Hz), 10.19 (1H, brs)

Synthesis Example 43

By reducing a compound in which R"" is CH₃CO in accordance with the step 10, a compound in which R"" is CH₃CH₂ (compound 61) was synthesized.

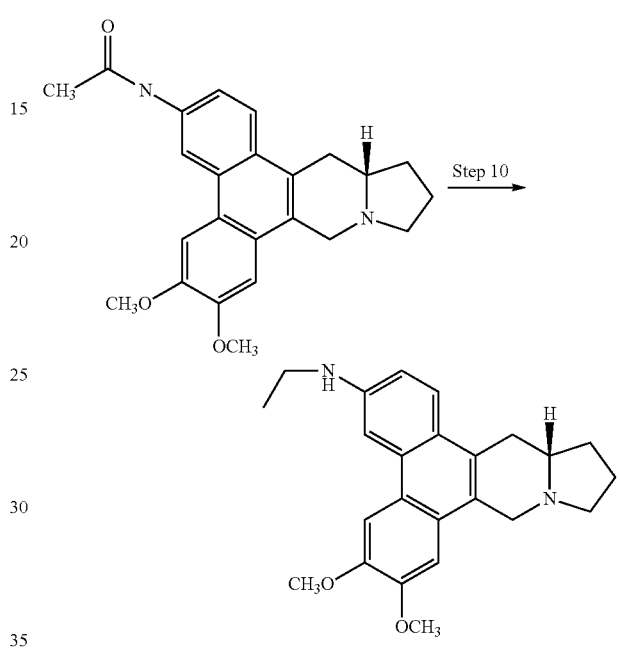

yield: 31.3%
¹HNMR (400 MHz, DMSO-d₆) δ: 1.26 (3H, t, J=7.1 Hz), 1.55-1.71 (1H, m), 1.76-1.94 (2H, m), 2.08-2.23 (1H, m), 2.30-2.45 (2H, m), 2.65-2.79 (1H, m), 3.27 (2H, q, J=7.1 Hz), 3.28-3.45 (2H, m), 3.49 (1H, d, J=15.1 Hz), 3.92 (3H, s), 3.98 (3H, s), 4.52 (1H, d, J=15.1 Hz), 5.72-5.80 (1H, m), 6.97 (1H, dd, J=2.2, 8.0 Hz), 7.15 (1H, s), 7.55 (1H, d, J=2.2 Hz), 7.74 (1H, d, J=8.0 Hz), 7.93 (1H, s)

Synthesis Example 44

Alkyl-substituted amine (compound 58) is obtained by reducing the imine obtained by the palladium-catalyzed amination reaction in accordance with the step 10.

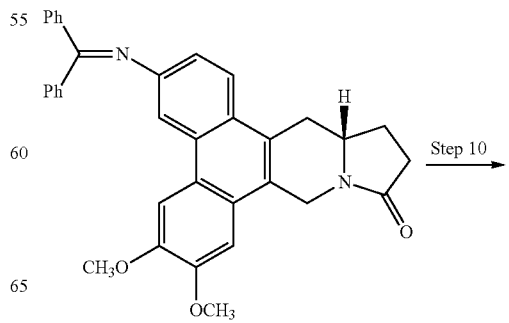

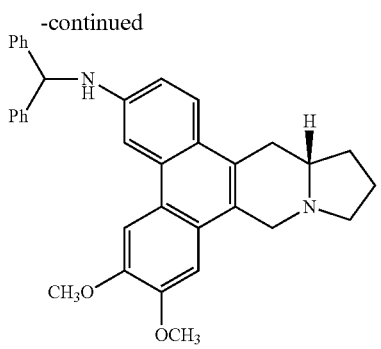

yield: 49%

¹HNMR (400 MHz, DMSO-d$_6$) δ: 1.50-1.68 (1H, m), 1.72-1.93 (2H, m), 2.04-2.20 (1H, m), 2.22-2.36 (2H, m), 2.60-2.74 (1H, m), 3.21-3.37 (2H, m), 3.44 (1H, d, J=15.0 Hz), 3.89 (3H, s), 3.91 (3H, s), 4.48 (1H, d, J=15.0 Hz), 5.90 (1H, d, J=6.1 Hz), 6.73 (1H, d, J=6.1 Hz), 7.08-7.62 (14H, m), 7.68 (1H, d, J=9.0 Hz)

Synthesis Example 45

Under the conditions of step 17, a compound having a heterocyclic group was synthesized by changing the amine used from benzophenone imine to pyrrolidine. And then, a ketone group was reduced by the step 10 (compound 57).

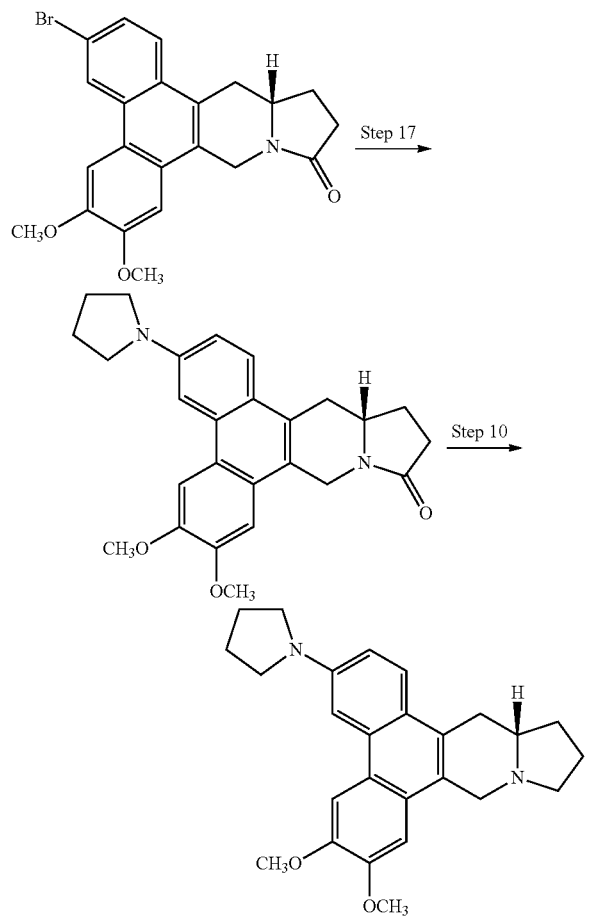

Step 17 yield: 84%

¹HNMR (400 MHz, CDCl$_3$) δ: 1.92-2.07 (1H, m), 2.07-2.15 (4H, m), 2.47-2.65 (3H, m), 2.77-2.93 (1H, m), 3.46-3.58 (5H, m), 3.89-4.00 (1H, m), 4.05 (3H, s), 4.11 (3H, s), 4.54 (1H, d, J=17.3 Hz), 5.29 (1H, d, J=17.3 Hz), 6.99 (1H, dd, J=2.3, 9.2 Hz), 7.16 (1H, s), 7.43 (1H, d, J=2.3 Hz), 7.85 (1H, d, J=9.2 Hz), 7.93 (1H, s)

Step 10 yield: 44%

¹HNMR (400 MHz, DMSO-d$_6$) δ: 1.50-1.80 (1H, m), 1.81-2.12 (6H, m), 2.20-2.68 (3H, m), 2.70-3.07 (1H, m), 3.21-3.37 (2H, m), 3.40-3.54 (5H, m), 3.93 (3H, s), 4.00 (3H, s), 4.51-4.64 (1H, m), 7.00 (1H, dd, J=1.9, 9.0 Hz), 7.15 (1H, s), 7.48 (1H, d, J=1.9 Hz), 7.84 (1H, d, J=9.0 Hz), 8.00 (1H, s)

Synthesis Example 46

A compound having a fluorine atom at R$^8$ (compound 14) was synthesized in accordance with step 19.

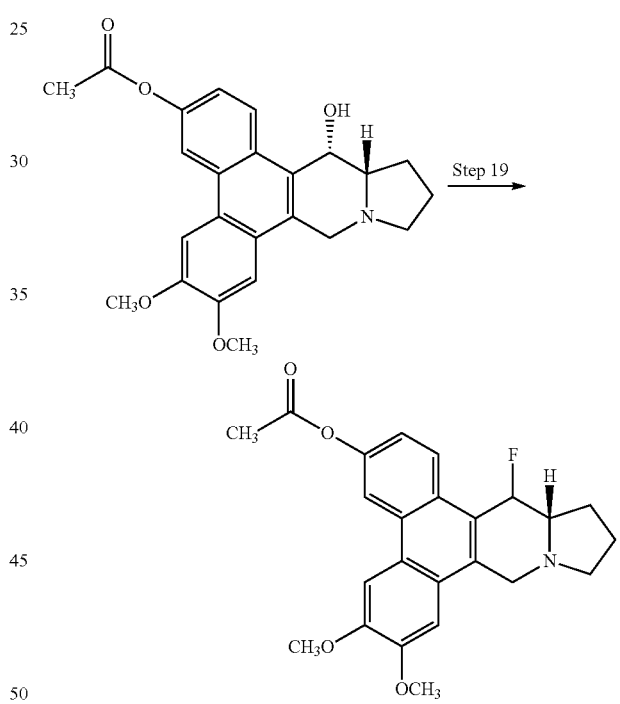

Step 19: Conversion of a Hydroxyl Group to a Fluorine Atom

In a round-bottom flask, 107 µl (0.81 mmol, 1.3 eq.) of diethylaminosulfur trifluoride was added to a solution of raw materials (250 mg, 0.62 mmol) in methylene chloride (15 ml) under an argon atmosphere while stirring with cooling on ice, followed by further stirring. After two hours, the disappearance of the raw materials was confirmed, and the resulting reaction liquid was directly purified by column chromatography (CHCl$_3$ only) to give 65 mg (25.6%) of a light yellow solid.

$[\alpha]_D^{27}$+112.67 (c=0.1, CHCl$_3$)

¹HNMR (400 MHz, DMSO-d$_6$) δ: 1.80-1.93 (2H, m), 1.95-2.16 (2H, m), 2.30-2.70 (2H, m), 2.36 (3H, s), 3.33-3.40 (1H, m), 3.55 (1H, dd, J=10.0, 15.4 Hz), 3.96 (3H, s), 4.03 (3H, s), 4.74 (1H, dd, J=4.8, 15.4 Hz), 4.76 (1H, d, J=9.8 Hz), 6.15 (1H, dd, J=1.7, 51.0 Hz), 7.35 (1H, s), 7.41 (1H, dd, J=2.2, 9.0 Hz), 8.11 (1H, s), 8.21 (1H, dd, J=2.4, 9.0 Hz), 8.54 (1H, d, J=2.2 Hz)

Synthesis Example 47

A compound having a hydroxymethyl group at $R^2$ (compound 59) was synthesized as shown below.

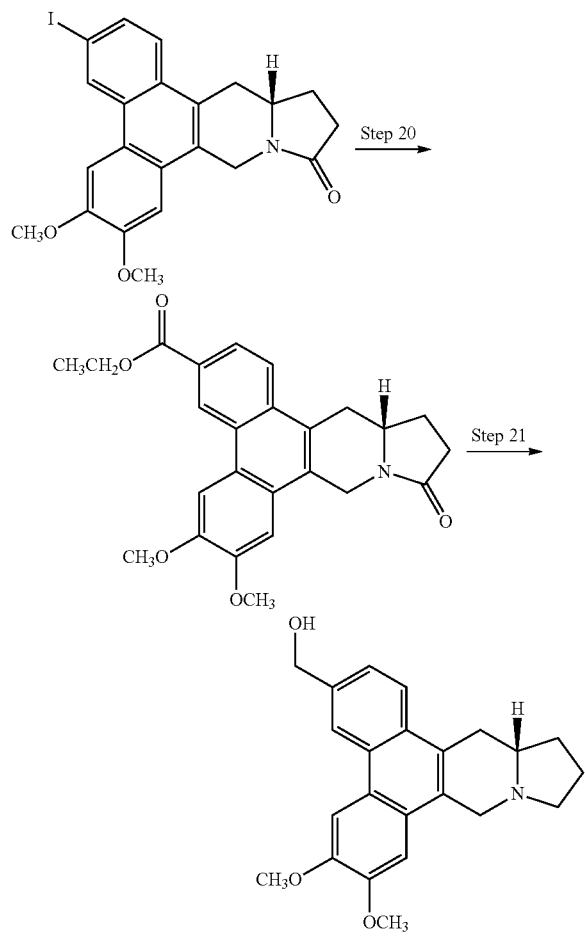

Step 20: Palladium-Catalyzed Carbonylation Reaction of Aromatic Halide

In a round-bottom flask, 6 mg (0.03 mmol, 0.07 eq.) of palladium acetate and 106 mg (0.77 mmol, 1.8 eq.) of potassium carbonate were added to a suspension of 200 mg (0.43 mmol) of raw materials in ethanol (15 mL), followed by stirring while heating at 80° C. under a carbon monoxide atmosphere. After four hours, the disappearance of the raw materials was confirmed. The resulting reaction liquid was cooled on ice and water was then added to quench the reaction. The aqueous layer was extracted with a solution of chloroform:methanol=4:1, and the organic layer was dried over anhydrous magnesium sulfate. The solvent was removed and the residual product was purified by column chromatography to give 112 mg (62.0%) of a light yellow solid.

$^1$HNMR (400 MHz, CDCl$_3$) δ: 1.49 (3H, t, J=7.1 Hz), 1.98-2.13 (1H, m), 2.52-2.66 (3H, m), 2.87-2.99 (1H, m), 3.61 (1H, dd, J=4.0, 16.0 Hz), 3.91-4.02 (1H, m), 4.08 (3H, s), 4.17 (3H, s), 4.50 (2H, q, J=7.1 Hz), 4.61 (1H, d, J=17.4 Hz), 5.39 (1H, d, J=17.4 Hz), 7.24 (1H, s), 8.04 (1H, d, J=8.6 Hz), 8.12 (1H, s), 8.19 (1H, dd, J=1.6, 8.6 Hz), 9.29 (1H, s)

Step 21: Reduction of Ester and Lactam

Under an argon atmosphere, a 1.3 mL of 1.0 M solution of diisobutylaluminum hydride in toluene (1.3 mmol, 6.0 eq.) was added to a solution of 90 mg (0.22 mmol) of raw materials in 5 mL of methylene chloride while stirring with cooling on ice. After two hours, the disappearance of the raw materials was confirmed, and 1 M hydrochloric acid was added to quench the reaction. Saturated sodium bicarbonate water was added to the resulting mixture to make it weakly basic. After that, the aqueous layer was extracted with a solution of chloroform:methanol=4:1, and the organic layer was dried over anhydrous magnesium sulfate. The solvent was removed under reduced pressure and the residual product was purified by column chromatography (chloroform:methanol=25:1) to give 32 mg (40.1%) of a white solid.

$^1$HNMR (400 MHz, DMSO-d$_6$) δ: 1.57-1.71 (1H, m), 1.76-1.94 (2H, m), 2.09-2.24 (1H, m), 2.32-2.45 (2H, m), 2.74-2.85 (1H, m), 3.31-3.43 (2H, m), 3.57 (1H, d, J=15.4 Hz), 3.94 (3H, s), 4.01 (3H, s), 4.59 (1H, d, J=15.4 Hz), 4.75 (2H, d, J=5.8 Hz), 5.30 (1H, t, J=5.8 Hz), 7.23 (1H, s), 7.56 (1H, d, J=8.5 Hz), 7.97 (1H, d, J=8.5 Hz), 8.13 (1H, s), 8.62 (1H, s) 7.96 (1H, d, J=2.4 Hz)

HPLC Analysis Condition

<HPLC Condition A>
Column: Daicel CHIRALPAK AS-RH (5 μm, 4.6×150 mm)
Mobile phase: a mixed solution of H$_2$O/acetonitrile (40:60)
Flow rate: 0.5 mL/min
Detection: 254 nm
Column temperature: 40° C.
Measurement time: 30 minutes <HPLC Condition B>
Column: Daicel CHIRALCEL OD-RH (5 μm, 4.6×150 mm)
Mobile phase: a mixed solution of a 20 mM (sodium) phosphate buffer (pH=5.6)/acetonitrile (40:60)
Flow rate: 0.5 mL/min
Detection: 254 nm
Temperature: 40° C.
Measurement time: 30 minutes <HPLC Condition C>
Column: Daicel CHIRALPAK AS-RH (5 μm, 4.6×150 mm)
Mobile phase: a mixed solution of H$_2$O/CH$_3$CN (1:4)
Flow rate: 0.5 ml/min
Detection: 254 nm
Column temperature: 40° C.

<HPLC Condition D>
Column: Daicel CHIRALCEL OD-RH (5 μm, 4.6×150 mm)
Mobile phase: a mixed solution of a 20 mM (sodium) phosphate buffer (pH=5.6)/CH$_3$CN (1:4)
Flow rate: 0.5 ml/min
Detection: 254 nm
Column temperature: 40° C.

In in vivo studies, each compound was used in the form of a salt. The solubilities are shown below.

TABLE 17

| Compound | Solubility (mg/mL)* |
|---|---|
| Compound 43 | 11.2 |
| Compound 44 | 10.3 |
| Compound 45 | 9.7 |
| Compound 46 | 11.3 |
| Compound 47 | 8.7 |
| Compound 48 | 10.1 |
| Compound 49 | 10.9 |

*the solubility in an aqueous solution of 5% glucose

The phenanthroindolizidine alkaloid compound of the present invention exhibited good solubility in a solvent. Particularly, when its methanesulfonate salt was dissolved in an aqueous solution of 5% glucose, it exhibited a sufficient solubility for administration (>8 mg/ml).

The compounds synthesized as above were used for biological activity tests in the form of an arbitrary salt. Specifically, the salts used were as follows.

It is to be noted that the compounds 43, 44, 45, 46, 47, 48, 52, 53, 55, and 66, and the aforementioned compounds 40, 31, 34, 36, 39, 35, 38, 32, 42, and 7 are each the same in structure, but only differ in the kind of salt; therefore, the synthetic method for the former compounds is in accordance with the aforementioned synthetic method.

TABLE 18

| Abbreviation | Compound Name |
| --- | --- |
| Compound 1 | (12aS,13S)-6,7-dimethoxy-9,10,11,12,12a,13-hexahydro-9a-aza-cyclopenta[b]triphenylene-13-ol hydrochloride |
| Compound 2 | (12aR,13R)-6,7-dimethoxy-9,10,11,12,12a,13-hexahydro-9a-aza-cyclopenta[b]triphenylene-13-ol hydrochloride |
| Compound 3 | (12aS,13S)-3-ethyl-6,7-dimethoxy-9,10,11,12,12a,13-hexahydro-9a-aza-cyclopenta[b]triphenylene-13-ol hydrochloride |
| Compound 4 | (12aR,13R)-3-ethyl-6,7-dimethoxy-9,10,11,12,12a,13-hexahydro-9a-aza-cyclopenta[b]triphenylene-13-ol hydrochloride |
| Compound 5 | (12aS,13S)-3-fluoro-6,7-dimethoxy-9,10,11,12,12a,13-hexahydro-9a-aza-cyclopenta[b]triphenylene-13-ol hydrochloride |
| Compound 6 | (12aR,13R)-3-fluoro-6,7-dimethoxy-9,10,11,12,12a,13-hexahydro-9a-aza-cyclopenta[b]triphenylene-13-ol hydrochloride |
| Compound 7 | acetic acid(12aS,13S)-13-hydroxy-6,7-dimethoxy-9,10,11,12,12a,13-hexahydro-9a-aza-cyclopenta[b]triphenylene-3-yl ester hydrochloride |
| Compound 8 | acetic acid(12aS,13S)-3-acetoxy-6,7-dimethoxy-9,10,11,12,12a,13-hexahydro-9a-aza-cyclopenta[b]triphenylene-13-yl ester hydrochloride |
| Compound 9 | isobutyric acid(12aS,13S)-13-hydroxy-6,7-dimethoxy-9,10,11,12,12a,13-hexahydro-9a-aza-cyclopenta[b]triphenylene-3-yl ester hydrochloride |
| Compound 10 | 2,2-dimethyl-propionic acid(12aS,13S)-13-hydroxy-6,7-dimethoxy-9,10,11,12,12a,13-hexahydro-9a-aza-cyclopenta[b]triphenylene-3-yl ester hydrochloride |

TABLE 19

| Abbreviation | Compound Name |
| --- | --- |
| Compound 11 | nicotinic acid(12aS,13S)-13-hydroxy-6,7-dimethoxy-9,10,11,12,12a,13-hexahydro-9a-aza-cyclopenta[b]triphenylene-3-yl ester hydrochloride |
| Compound 12 | isonicotinic acid(12aS,13S)-13-hydroxy-6,7-dimethoxy-9,10,11,12,12a,13-hexahydro-9a-aza-cyclopenta[b]triphenylene-3-yl ester hydrochloride |
| Compound 13 | [1,4']bipiperidinyl-1'-carboxylic acid(12aS,13S)-13-hydroxy-6,7-dimethoxy-9,10,11,12,12a,13-hexahydro-9a-aza-cyclopenta[b]triphenylene-3-yl ester |

TABLE 19-continued

| Abbreviation | Compound Name |
| --- | --- |
| Compound 14 | acetic acid(S)-13-fluoro-6,7-dimethoxy-9,10,11,12,12a,13-hexahydro-9a-aza-cyclopenta[b]triphenylene-3-yl ester hydrochloride |
| Compound 15 | propionic acid(12aS,13S)-13-hydroxy-6,7-dimethoxy-9,10,11,12,12a,13-hexahydro-9a-aza-cyclopenta[b]triphenylene-3-yl ester hydrochloride |
| Compound 16 | succinic acid(12aS,13S)-13-hydroxy-6,7-dimethoxy-9,10,11,12,12a,13-hexahydro-9a-aza-cyclopenta[b]triphenylene-3-yl ester methyl ester hydrochloride |
| Compound 17 | carbonic acid(12aS,13S)-13-hydroxy-6,7-dimethoxy-9,10,11,12,12a,13-hexahydro-9a-aza-cyclopenta[b]triphenylene-3-yl ester methyl ester hydrochloride |
| Compound 18 | ((12aS,13S)-13-hydroxy-6,7-dimethoxy-9,10,11,12,12a,13-hexahydro-9a-aza-cyclopenta[b]triphenylene-3-yl)-carbamic acid isobutyl ester hydrochloride |
| Compound 19 | thiophene-2-carboxylic acid(12aS,13S)-13-hydroxy-6,7-dimethoxy-9,10,11,12,12a,13-hexahydro-9a-aza-cyclopenta[b]triphenylene-3-yl ester hydrochloride |

TABLE 20

| Abbreviation | Compound name |
| --- | --- |
| Compound 20 | furan-2-carboxylic acid(12aS,13S)-13-hydroxy-6,7-dimethoxy-9,10,11,12,12a,13-hexahydro-9a-aza-cyclopenta[b]triphenylene-3-yl ester hydrochloride |
| Compound 21 | dimethyl-carbamic acid(12aS,13S)-13-hydroxy-6,7-dimethoxy-9,10,11,12,12a,13-hexahydro-9a-aza-cyclopenta[b]triphenylene-3-yl ester hydrochloride |
| Compound 22 | furan-3-carboxylic acid(12aS,13S)-13-hydroxy-6,7-dimethoxy-9,10,11,12,12a,13-hexahydro-9a-aza-cyclopenta[b]triphenylene-3-yl ester hydrochloride |
| Compound 23 | thiophene-3-carboxylic acid(12aS,13S)-13-hydroxy-6,7-dimethoxy-9,10,11,12,12a,13-hexahydro-9a-aza-cyclopenta[b]triphenylene-3-yl ester hydrochloride |
| Compound 24 | octanedionic acid(9S,12S)-13-hydroxy-6,7-dimethoxy-9,10,11,12,12a,13-hexahydro-9a-aza-cyclopenta[b]triphenylene-3-yl ester(12aS,13S)-13-hydroxy-6,7-dimethoxy-9,10,11,12,12a,13-hexahydro-9a-aza-cyclopenta[b]triphenylene-3-yl ester hydrochloride |
| Compound 25 | (12aS,13S)-3-amino-6,7-dimethoxy-9,10,11,12,12a,13-hexahydro-9a-aza-cyclopenta[b]triphenylene-13-ol hydrochloride |
| Compound 26 | ((12aS,13S)-13-hydroxy-6,7-dimethoxy-9,10,11,12,12a,13-hexahydro-9a-aza-cyclopenta[b]triphenylene-3-yl)-carbamic acid benzyl ester hydrochloride |

TABLE 21

| Abbreviation | Compound name |
| --- | --- |
| Compound 27 | carbonic acid(12aS,13S)-13-hydroxy-6,7-dimethoxy-9,10,11,12,12a,13-hexahydro-9a-aza-cyclopenta[b]triphenylene-3-yl ester-propyn-2-yl ester hydrochloride |
| Compound 28 | carbonic acid ethyl ester(12aS,13S)-13-hydroxy-6,7-dimethoxy-9,10,11,12,12a,13-hexahydro-9a-aza-cyclopenta[b]triphenylene-3-yl ester hydrochloride |

TABLE 21-continued

| Abbreviation | Compound name |
|---|---|
| Compound 29 | (12aS,13S)-6,7-dimethoxy-9,10,11,12,12a,13-hexahydro-9a-aza-cyclopenta[b]triphenylene-2,13-diol hydrochloride |
| Compound 30 | (12aS,13S)-6,7-dimethoxy-9,10,11,12,12a,13-hexahydro-9a-aza-cyclopenta[b]triphenylene-4,13-diol hydrochloride |
| Compound 31 | (S)-3-fluoro-6,7-dimethoxy-9,10,11,12,12a,13-hexahydro-9a-aza-cyclopenta[b]triphenylene hydrochloride |
| Compound 32 | (S)-6,7-dimethoxy-9,10,11,12,12a,13-hexahydro-9a-aza-cyclopenta[b]triphenylene hydrochloride |
| Compound 33 | (S)-6,7-dimethoxy-9,10,11,12,12a,13-hexahydro-9a-aza-cyclopenta[b]triphenylene-2-ol hydrochloride |
| Compound 34 | acetic acid(S)-6,7-dimethoxy-9,10,11,12,12a,13-hexahydro-9a-aza-cyclopenta[b]triphenylene-3-yl ester hydrochloride |
| Compound 35 | 2,2-dimethyl-propionic acid(S)-6,7-dimethoxy-9,10,11,12,12a,13-hexahydro-9a-aza-cyclopenta[b]triphenylene-3-yl ester hydrochloride |

TABLE 22

| Abbreviation | Compound name |
|---|---|
| Compound 36 | succinic acid(S)-6,7-dimethoxy-9,10,11,12,12a,13-hexahydro-9a-aza-cyclopenta[b]triphenylene-3-yl ester methyl ester hydrochloride |
| Compound 37 | carbonic acid(S)-6,7-dimethoxy-9,10,11,12,12a,13-hexahydro-9a-aza-cyclopenta[b]triphenylene-3-yl ester methyl ester hydrochloride |
| Compound 38 | furan-2-carboxylic acid(S)-6,7-dimethoxy-9,10,11,12,12a,13-hexahydro-9a-aza-cyclopenta[b]triphenylene-3-yl ester hydrochloride |
| Compound 39 | nicotinic acid(S)-6,7-dimethoxy-9,10,11,12,12a,13-hexahydro-9a-aza-cyclopenta[b]triphenylene-3-yl ester hydrochloride |
| Compound 40 | (S)-6,7-dimethoxy-9,10,11,12,12a,13-hexahydro-9a-aza-cyclopenta[b]triphenylene-4-ol hydrochloride |
| Compound 41 | (S)-3-ethyl-6,7-dimethoxy-9,10,11,12,12a,13-hexahydro-9a-aza-cyclopenta[b]triphenylene hydrochloride |
| Compound 42 | ((S)-6,7-dimethoxy-9,10,11,12,12a,13-hexahydro-9a-aza-cyclopenta[b]triphenylene-3-yl)-carbamic acid isobutyl ester hydrochloride |
| Compound 43 | (12aS,13S)-6,7-dimethoxy-9,10,11,12,12a,13-hexahydro-9a-aza-cyclopenta[b]triphenylene-4,13-diol methanesulfonate |

TABLE 23

| Abbreviation | Compound name |
|---|---|
| Compound 44 | (S)-3-fluoro-6,7-dimethoxy-9,10,11,12,12a,13-hexahydro-9a-aza-cyclopenta[b]triphenylene methanesulfonate |
| Compound 45 | acetic acid(S)-6,7-dimethoxy-9,10,11,12,12a,13-hexahydro-9a-aza-cyclopenta[b]triphenylene-3-yl ester methanesulfonate |
| Compound 46 | succinic acid(S)-6,7-dimethoxy-9,10,11,12,12a,13-hexahydro-9a-aza-cyclopenta[b]triphenylene-3-yl ester methyl ester methanesulfonate |

TABLE 23-continued

| Abbreviation | Compound name |
|---|---|
| Compound 47 | nicotinic acid(S)-6,7-dimethoxy-9,10,11,12,12a,13-hexahydro-9a-aza-cyclopenta[b]triphenylene-3-yl ester methanesulfonate |
| Compound 48 | 2,2-dimethyl-propionic acid(S)-6,7-dimethoxy-9,10,11,12,12a,13-hexahydro-9a-aza-cyclopenta[b]triphenylene-3-yl ester methanesulfonate |
| Compound 49 | pentanoic acid(S)-6,7-dimethoxy-9,10,11,12,12a,13-hexahydro-9a-aza-cyclopenta[b]triphenylene-3-yl ester methanesulfonate |
| Compound 50 | butyric acid(S)-6,7-dimethoxy-9,10,11,12,12a,13-hexahydro-9a-aza-cyclopenta[b]triphenylene-3-yl ester methanesulfonate |

TABLE 24

| Abbreviation | Compound name |
|---|---|
| Compound 51 | propionic acid(S)-6,7-dimethoxy-9,10,11,12,12a,13-hexahydro-9a-aza-cyclopenta[b]triphenylene-3-yl ester methanesulfonate |
| Compound 52 | furan-2-carboxylic acid(S)-6,7-dimethoxy-9,10,11,12,12a,13-hexahydro-9a-aza-cyclopenta[b]triphenylene-3-yl ester methanesulfonate |
| Compound 53 | (S)-6,7-dimethoxy-9,10,11,12,12a,13-hexahydro-9a-aza-cyclopenta[b]triphenylene methanesulfonate |
| Compound 54 | (S)-3-amino-6,7-dimethoxy-9,10,11,12,12a,13-hexahydro-9a-aza-cyclopenta[b]triphenylene methanesulfonate |
| Compound 55 | ((S)-6,7-dimethoxy-9,10,11,12,12a,13-hexahydro-9a-aza-cyclopenta[b]triphenylene-3-yl)-carbamic acid isobutyl ester methanesulfonate |
| Compound 56 | N-((S)-6,7-dimethoxy-9,10,11,12,12a,13-hexahydro-9a-aza-cyclopenta[b]triphenylene-3-yl)-acetamide methanesulfonate |
| Compound 57 | (S)-6,7-dimethoxy-3-pyrrolidine-9,10,11,12,12a,13-hexahydro-9a-aza-cyclopenta[b]triphenylene methanesulfonate |
| Compound 58 | benzhydryl-((S)-6,7-dimethoxy-3-pyrrolidine-9,10,11,12,12a,13-hexahydro-9a-aza-cyclopenta[b]triphenylene-3-yl)-amine methanesulfonate |

TABLE 25

| Abbreviation | Compound name |
|---|---|
| Compound 59 | ((S)-6,7-dimethoxy-9,10,11,12,12a,13-hexahydro-9a-aza-cyclopenta[b]triphenylene-3-yl)-methanol methanesulfonate |
| Compound 60 | N-((S)-6,7-dimethoxy-9,10,11,12,12a,13-hexahydro-9a-aza-cyclopenta[b]triphenylene-3-yl)-2,2,2-trifluoro-acetamide methanesulfonate |
| Compound 61 | ((S)-6,7-dimethoxy-9,10,11,12,12a,13-hexahydro-9a-aza-cyclopenta[b]triphenylene-3-yl)-ethyl-amine methanesulfonate |
| Compound 62 | ((S)-6,7-dimethoxy-9,10,11,12,12a,13-hexahydro-9a-aza-cyclopenta[b]triphenylene-3-yl)-carbamic acid methyl ester methanesulfonate |

TABLE 26

| Abbreviation | Compound name |
|---|---|
| Compound 63 | N-((S)-6,7-dimethoxy-9,10,11,12,12a,13-hexahydro-9a-aza-cyclopenta[b]triphenylene-3-yl)-methanesulfonamide methanesulfonate |
| Compound 64 | N-((S)-6,7-dimethoxy-9,10,11,12,12a,13-hexahydro-9a-aza-cyclopenta[b]triphenylene-3-yl)-formamide methanesulfonate |
| Compound 65 | N-((S)-6,7-dimethoxy-9,10,11,12,12a,13-hexahydro-9a-aza-cyclopenta[b]triphenylene-3-yl)-benzamide methanesulfonate |
| Compound 66 | acetic acid(12aS,13S)-13-hydroxy-6,7-dimethoxy-9,10,11,12,12a,13-hexahydro-9a-aza-cyclopenta[b]triphenylene-3-yl ester methanesulfonate |
| Compound 67 | (S)-6,7-dimethoxy-9,10,11,12,12a,13-hexahydro-9a-aza-cyclopenta[b]triphenylene-3-ol hydrochloride |

Example 1

Inhibitory Action on the NFκB Activity

The action of the phenanthroindolizidine alkaloid compound of the present invention on the NFκB activity was studied using a luciferase assay. Human colon cancer SW480 cells were transfected with pNFκB-Luc Plasmid (Stratagene), which is a reporter vector in which a five-time tandem repeat of the NFκB responsive element (NRE) is integrated into the upstream of the luciferase gene, using Lipofectamine 2000 (Invitrogen Corporation) in accordance with the attached operating procedure. Subsequently, the cells were cultured in an RPMI1640 medium containing 10% FBS, 100 U/mL penicillin, 100 µg/mL streptomycin, and 0.5 mg/mL G418 to produce SW480 cells having the luciferase gene, the expression of which is regulated by NRE, stably introduced therein (SW480/NRE-Luc cells). Likewise, SW480 cells were transfected with pGL3-Control Vector (Promega Corporation), which is a reporter vector in which the SV40 promoter is integrated into the upstream of the luciferase gene, to produce SW480 cells having the luciferase gene, the expression of which is regulated by the SV40 promoter, stably introduced therein (SW480/SV40-Luc cells). The SW480/NRE-Luc cells or the SW480/SV40-Luc cells were suspended in an RPMI1640 medium containing 10% FBS, 100 U/mL penicillin, and 100 µg/mL streptomycin (10% FBS/RPMI1640), and then seeded in a 96-well microplate, followed by culturing under conditions of 5% $CO_2$ and at 37° C. (5000 cells/well). After an overnight culture, the compound of the present invention was added, followed by culturing for one hour. Further, 50 ng/mL TNFα (Sigma-Aldrich Corporation) was added, followed by culturing for four hours. Subsequently, a Steady-Glo Luciferase Assay reagent (Promega Corporation) was added, and the luminescent intensity was detected by SpectraMax M5e (Molecular Devices, Inc.) to measure the intracellular luciferase activity. It is to be noted that the action of the compound of the present invention on the NFκB activity or the SV40 promoter activity was shown as $IC_{50}$ values (the concentration of a test compound needed for 50% inhibition of the induction of the luciferase expression). The results are shown in the following Tables 27 to 29.

As shown in the following Tables, the phenanthroindolizidine alkaloid compound of the present invention exhibited a potent inhibitory activity on the NFκB activity. While pyrrolidine dithiocarbamate (PDTC), which is known to have an NFκB inhibitory activity, was used as a positive control drug in the present experiment, all of the compounds of the present invention studied exhibited a stronger NFκB inhibitory activity than did PDTC. Meanwhile, it was shown that these compounds did not affect the SV40 promoter activity, indicating that they specifically acted on NFκB.

TABLE 27

| Compound | NFκB inhibitory activity $IC_{50}$(ng/mL) | SV40 promoter inhibitory activity $IC_{50}$(ng/mL) |
|---|---|---|
| Compound 1 | 2.7 | >1000 |
| Compound 2 | 386.6 | >10000 |
| Compound 3 | 104.8 | >10000 |
| Compound 4 | 200.6 | >10000 |
| Compound 5 | 20.7 | >1000 |
| Compound 6 | 165.6 | >10000 |
| Compound 7 | 0.25 | >100 |
| Compound 8 | 63.2 | >1000 |
| Compound 9 | 0.26 | >100 |
| Compound 10 | 0.49 | >100 |
| Compound 11 | 0.48 | >10 |
| Compound 12 | 0.33 | >100 |
| Compound 13 | 20.3 | >1000 |
| Compound 14 | 1.7 | >100 |
| Compound 15 | 0.20 | >100 |
| Compound 16 | 0.37 | >100 |
| Compound 17 | 0.83 | >100 |
| Compound 18 | 15.5 | >1000 |
| Compound 19 | 3.0 | >100 |
| Compound 20 | 0.46 | >100 |
| Compound 21 | 23.3 | >10000 |
| Compound 22 | 1.7 | >1000 |
| Compound 23 | 4.1 | >100 |
| Compound 24 | 0.90 | >100 |
| Compound 25 | 1.1 | >100 |
| Compound 26 | 19.9 | >1000 |

TABLE 28

| Compound | NFκB inhibitory activity $IC_{50}$(ng/mL) | SV40 promoter inhibitory activity $IC_{50}$(ng/mL) |
|---|---|---|
| Compound 27 | 0.37 | >10 |
| Compound 28 | 1.0 | >10 |
| Compound 29 | 1.4 | >1000 |
| Compound 30 | 0.017 | >1000 |
| Compound 31 | 28.8 | >1000 |
| Compound 32 | 27.8 | >100 |
| Compound 33 | 5.3 | >100 |
| Compound 34 | 0.026 | >100 |
| Compound 35 | 2.4 | >1000 |
| Compound 36 | 0.64 | >100 |
| Compound 37 | 2.9 | >100 |
| Compound 38 | 0.50 | >1000 |
| Compound 39 | 2.2 | >100 |
| Compound 40 | 2.4 | >1000 |
| Compound 41 | 281.4 | >10000 |
| Compound 42 | 116.6 | >10000 |
| Compound 43 | 2.7 | >1000 |
| Compound 44 | 36.8 | >1000 |

TABLE 29

| Compound | NFκB inhibitory activity $IC_{50}$(ng/mL) | SV40 promoter inhibitory activity $IC_{50}$(ng/mL) |
|---|---|---|
| Compound 45 | 0.41 | >100 |
| Compound 46 | 0.13 | >1000 |
| Compound 47 | 0.42 | >1000 |
| Compound 48 | 0.40 | >1000 |
| Compound 49 | 0.41 | >1000 |
| Compound 50 | 0.34 | >100 |
| Compound 51 | 0.80 | >100 |

TABLE 29-continued

| Compound | NFκB inhibitory activity IC$_{50}$(ng/mL) | SV40 promoter inhibitory activity IC$_{50}$(ng/mL) |
|---|---|---|
| Compound 52 | 0.61 | >1000 |
| Compound 53 | 19.1 | >10000 |
| Compound 54 | 2.0 | >10 |
| Compound 55 | 0.50 | >10000 |
| Compound 56 | 2.9 | >10 |
| Compound 57 | 0.67 | >10000 |
| Compound 58 | 16.2 | >10000 |
| PDTC | 2400 | >10000 |

Example 2

Inhibitory Action on the Proliferation of Cancer Cells

The action of the phenanthroindolizidine alkaloid compound of the present invention on the proliferation of human colon cancer SW480 cells, HT-29 cells, and human non-small cell lung cancer A549 cells was studied. The SW480 cells were suspended in a 10% FBS/RPMI1640 and then seeded in a 96-well microplate, followed by culturing in 5% CO$_2$ at 37° C. (2000 cells/well). The A549 cells and the HT-29 cells were each suspended in a DMEM medium containing 10% FBS, 100 U/mL penicillin, and 100 μg/mL streptomycin (10% FBS/DMEM) and a DMEM F-12 HAM medium containing 10% FBS, 100 U/mL penicillin, and 100 μg/mL streptomycin (10% FBS/DMEM F12 HAM), and then seeded in 96-well microplates, followed by culturing in 5% CO$_2$ at 37° C. (1000 cells/well). After an overnight culture, the compound of the present invention was added, followed by further culturing for 48 hours (SW480 cells) and 96 hours (A549 cells and HT-29 cells). After culturing, the number of viable cells was counted using TetraColor ONE (Seikagaku Corporation) in accordance with the attached operating procedure. The results were expressed as the concentration of a test compound needed for 50% inhibition of the proliferation of the cells (IC$_{50}$). As a result, as shown in the following Tables 30 to 32, the phenanthroindolizidine alkaloid compound of the present invention exhibited a potent inhibitory action on the proliferation of SW480 cells, HT-29 cells, and A549 cells.

TABLE 30

| Compound | SW480 proliferation inhibitory action IC$_{50}$(ng/mL) | HT-29 proliferation inhibitory action IC$_{50}$(ng/mL) | A549 proliferation inhibitory action IC$_{50}$(ng/mL) |
|---|---|---|---|
| Compound 1 | 5.1 | 3.7 | 2.6 |
| Compound 2 | 1016.0 | 204.0 | 211 |
| Compound 3 | 218.9 | 50.8 | 24.5 |
| Compound 4 | 513.2 | 121.0 | 101.0 |
| Compound 5 | 39.2 | 7.2 | 4.1 |
| Compound 6 | 566.9 | 38.8 | 34.1 |
| Compound 7 | 0.41 | 0.080 | 0.63 |
| Compound 8 | 17.0 | 5.8 | 1.5 |
| Compound 9 | 0.36 | 0.38 | 0.57 |
| Compound 10 | 0.73 | 0.47 | 0.14 |
| Compound 11 | 0.50 | 0.44 | 0.028 |
| Compound 12 | 0.51 | 0.62 | 0.19 |
| Compound 13 | 19.5 | 21.6 | 7.4 |
| Compound 14 | 2.1 | 0.62 | 0.23 |
| Compound 15 | 0.39 | 0.62 | 0.35 |
| Compound 16 | 0.76 | 0.17 | 0.59 |
| Compound 17 | 0.63 | 0.067 | 0.53 |
| Compound 18 | 27.6 | 18.1 | 16.2 |
| Compound 19 | 1.3 | 1.69 | 0.82 |
| Compound 20 | 0.67 | 0.76 | 0.42 |
| Compound 21 | 38.3 | 24.2 | 16.4 |
| Compound 22 | 2.8 | 1.9 | 1.1 |
| Compound 23 | 3.1 | 1.4 | 0.76 |
| Compound 24 | 0.77 | 0.24 | 0.18 |
| Compound 25 | 2.3 | 0.28 | 0.4 |
| Compound 26 | 37.3 | 6.7 | 8.8 |

TABLE 31

| Compound | SW480 proliferation inhibitory action IC$_{50}$(ng/mL) | HT-29 proliferation inhibitory action IC$_{50}$(ng/mL) | A549 proliferation inhibitory action IC$_{50}$(ng/mL) |
|---|---|---|---|
| Compound 27 | 0.66 | 0.055 | 0.025 |
| Compound 28 | 0.65 | 0.064 | 0.037 |
| Compound 29 | 4.0 | 2.5 | 1.7 |
| Compound 30 | 0.45 | 30.5 | 1.2 |
| Compound 31 | 50.2 | 10.6 | 1.5 |
| Compound 32 | 39.3 | 3.1 | 0.7 |
| Compound 33 | 10.8 | 6.4 | 0.97 |
| Compound 34 | 0.042 | 0.52 | 0.18 |
| Compound 35 | 4.1 | 3.7 | 1.2 |
| Compound 36 | 0.96 | 2.3 | 0.82 |
| Compound 37 | 0.68 | 1.6 | 0.65 |
| Compound 38 | 0.62 | 3.2 | 1.1 |
| Compound 39 | 1.3 | 2.6 | 0.97 |
| Compound 40 | 4.0 | 67.9 | 3.3 |
| Compound 41 | 391.1 | 167.1 | 112.2 |
| Compound 42 | 96.3 | 19.0 | 27.0 |
| Compound 43 | 6.2 | 100.3 | 4.4 |
| Compound 44 | 64.9 | 12.8 | 6.0 |
| Compound 45 | 0.76 | 1.5 | 0.64 |
| Compound 46 | 0.36 | 2.1 | 1.2 |
| Compound 47 | 0.38 | 1.9 | 1.1 |
| Compound 48 | 0.58 | 2.0 | 1.2 |
| Compound 49 | 0.62 | 2.0 | 1.1 |
| Compound 50 | 0.54 | 1.5 | 0.86 |
| Compound 51 | 1.1 | 1.6 | 0.78 |

TABLE 32

| Compound | SW480 proliferation inhibitory action IC$_{50}$(ng/mL) | HT-29 proliferation inhibitory action IC$_{50}$(ng/mL) | A549 proliferation inhibitory action IC$_{50}$(ng/mL) |
|---|---|---|---|
| Compound 52 | 0.51 | 2.0 | 1.3 |
| Compound 53 | 32.9 | 58.5 | 28.9 |
| Compound 54 | 3.9 | 4.15 | 2.8 |
| Compound 55 | 0.76 | 46.0 | 33.7 |
| Compound 56 | 4.8 | 2.4 | 2.2 |
| Compound 57 | 1.0 | 74.1 | 61.1 |
| Compound 58 | 42.3 | 52.2 | 20.7 |

Example 3

Antitumor Effect in Mice Transplanted with Mouse Fibrosarcoma Meth A Cells

The antitumor effect of the phenanthroindolizidine alkaloid compound of the present invention in vivo was studied using mice transplanted with mouse fibrosarcoma Meth A cells. Meth A cells were transplanted subcutaneously in the inguinal region of male 7-week-old BALB/c mice ($2.5 \times 10^5$ cells/mouse). Subsequently, on days 1, 5, and 9, the compound of the present invention was intravenously administered. To a control group, physiological saline, a solvent, was administered. On day 21 after the cell transplantation, tumor was excised and measured for its weight, and subsequently a tumor growth-inhibition rate IR (%) was obtained by the following formula.

Tumor growth-inhibition rate IR (%)=(1−the weight of the tumor in an administration group/the weight of the tumor in a control group)×100

The results thus obtained were shown in the following Table 33. The phenanthroindolizidine alkaloid compound of the present invention was shown to exhibit an antitumor effect in mice transplanted with mouse fibrosarcoma Meth A cells.

TABLE 33

| Compound | Total dose (mg/kg) | Tumor growth inhibition rate IR(%) |
|---|---|---|
| Compound 16 | 25 | 48.8* |
|  | 50 | 39.1 |
| Compound 17 | 25 | 54.2* |
|  | 50 | 50.0 |
| Compound 20 | 25 | 36.7 |
|  | 50 | 53.0* |
| Compound 40 | 25 | 25.8 |
|  | 50 | 45.1* |

*$P < 0.05$,
**$P < 0.01$; a significant difference in comparison with a solvent (Dunnett's test)

Example 4

Antitumor Effect in Mice Transplanted with Human Colon Cancer HCT116 Cells

The antitumor effect of the phenanthroindolizidine alkaloid compound of the present invention in vivo was studied using mice transplanted with human colon cancer HCT116 cells. HCT116 cells were transplanted subcutaneously in the inguinal region of male 6-week-old BALB/c nude mice ($2 \times 10^6$ cells/mouse). On days 1 to 5 and on days 8 to 12 after the time at which the estimated tumor volume obtained by $\frac{1}{2}ab^2$ (a and b indicate the major axis and the minor axis of tumor, respectively) reached approximately 100 mm$^3$ (day 0), the compound of the present invention was administered (intraperitoneal administration). To a control group, a 5% glucose solution, a solvent, was administered. On day 21, tumor was excised and measured for its weight, and subsequently a tumor proliferation-inhibition rate IR (%) was calculated. As a result, as shown in the following Table 34, the phenanthroindolizidine alkaloid compound of the present invention was shown to exhibit an antitumor effect in mice transplanted with human colon cancer HCT116 cells.

TABLE 34

| Compound | Total dose (mg/kg) | Tumor growth inhibition rate IR(%) |
|---|---|---|
| Compound 44 | 100 | 30.7** |
| Compound 45 | 200 | 34.7** |

TABLE 34-continued

| Compound | Total dose (mg/kg) | Tumor growth inhibition rate IR(%) |
|---|---|---|
| Compound 46 | 200 | 34.6** |
| Compound 56 | 50 | 39.1** |
|  | 100 | 68.9** |

*$P < 0.05$,
**$P < 0.01$,
***$P < 0.001$; a significant difference in comparison with a solvent (Dunnett's test)

Example 5

Animal Toxicity Test

In order to examine the toxicity of the phenanthroindolizidine alkaloid compound of the present invention in animals, the compound of the present invention was intravenously administered to mice transplanted with mouse fibrosarcoma Meth A cells (total doses were 25 and 50 mg/kg) on days 1, 5, and 9 after the day of transplantation (day 0), and its effect on the survival of the mice was observed for three weeks from the initiation of the administration. Also, the toxicity of known phenanthroindolizidine alkaloid compounds, namely (12aS,13S)-6,7-dimethoxy-9,10,11,12,12a,13-hexahydro-9a-aza-cyclopenta[b]triphenylene-3,13-diol (known compound 1; refer to WO01/023384) and (12aS,13S)-3,6,7-trimethoxy-9,10,11,12,12a,13-hexahydro-9a-aza-cyclopenta[b]triphenylene-13-ol (known compound 2; refer to Planta Med., 2002, 68: 186-188), was simultaneously studied. To a control group, a physiological saline solution, a solvent, was administered. As a result, as shown in the following Tables 35 and 36, all the mice survived in a group administered with the compound of the present invention. On the other hand, all the mice died in a group administered with 50 mg/kg of the known phenanthroindolizidine alkaloid compounds (known compounds 1 and 2). Particularly with the known compound 2, some of the mice also died in a group administered with 25 mg/kg of the compound. From the above results, the phenanthroindolizidine alkaloid compound of the present invention was shown to have reduced toxicity in animals compared to the known compounds 1 and 2.

TABLE 35

| Compound | Total dose (mg/kg) | Mortality rate |
|---|---|---|
| Solvent | 0 | 0/5 |
| Known compound 1 | 25 | 0/5 |
|  | 50 | 5/5 |
| Known Compound 2 | 25 | 2/5 |
|  | 50 | 5/5 |
| Compound 2 | 25 | 0/5 |
|  | 50 | 0/5 |
| Compound 4 | 25 | 0/5 |
|  | 50 | 0/5 |
| Compound 6 | 25 | 0/5 |
|  | 50 | 0/5 |
| Compound 7 | 25 | 0/5 |
|  | 50 | 0/5 |
| Compound 8 | 25 | 0/5 |
|  | 50 | 0/5 |
| Compound 13 | 25 | 0/5 |
|  | 50 | 0/5 |
| Compound 14 | 25 | 0/5 |
|  | 50 | 0/5 |
| Compound 19 | 25 | 0/5 |
|  | 50 | 0/5 |
| Compound 20 | 25 | 0/5 |
|  | 50 | 0/5 |

TABLE 36

| Compound | Total dose (mg/kg) | Mortality rate |
|---|---|---|
| Compound 21 | 25 | 0/5 |
| | 50 | 0/5 |
| Compound 27 | 25 | 0/5 |
| | 50 | 0/5 |
| Compound 28 | 25 | 0/5 |
| | 50 | 0/5 |
| Compound 29 | 25 | 0/5 |
| | 50 | 0/5 |
| Compound 31 | 25 | 0/5 |
| | 50 | 0/5 |
| Compound 32 | 25 | 0/5 |
| | 50 | 0/5 |

TABLE 37

| Compound | Total dose (mg/kg) | Mortality rate |
|---|---|---|
| Compound 33 | 25 | 0/5 |
| | 50 | 0/5 |
| Compound 34 | 25 | 0/5 |
| | 50 | 0/5 |
| Compound 36 | 25 | 0/5 |
| | 50 | 0/5 |
| Compound 37 | 25 | 0/5 |
| | 50 | 0/5 |
| Compound 38 | 25 | 0/5 |
| | 50 | 0/5 |
| Compound 39 | 25 | 0/5 |
| | 50 | 0/5 |
| Compound 40 | 25 | 0/5 |
| | 50 | 0/5 |

Example 6

Production of Tablets

The components shown below were mixed and the resulting mixture was tableted.

TABLE 38

| | |
|---|---|
| Compound 34 | 100 mg |
| Lactose | 100 mg |
| Potato starch | 39 mg |
| Microcrystalline cellulose | 30 mg |
| Synthetic aluminum silicate | 30 mg |
| Calcium stearate | 1 mg |
| Total (per tablet) | 300 mg |

The invention claimed is:

1. A compound represented by formula (1) or a salt thereof:

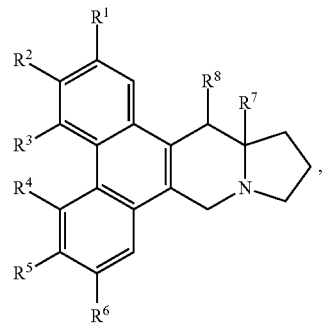

(1)

wherein:
$R^1$ represents a hydrogen atom, a lower alkyl group, a hydroxyl group, a lower alkyloxy group, or a halogen atom;
$R^2$ represents a hydrogen atom, a lower alkyl group, a halogen atom, a lower alkylcarbonyloxy group optionally having a substituent, a heterocyclic carbonyloxy group, a lower alkyloxycarbonyloxy group, a lower alkyl-substituted aminocarbonyloxy group, an amino group optionally having a substituent, a lower alkyl-substituted amino group optionally having a substituent, a heterocyclic group, a lower alkyloxycarbonylamino group optionally having a substituent, a lower alkylcarbonylamino group, a formamide group, or a hydroxy lower alkyl group;
$R^3$ represents a hydrogen atom, a lower alkyl group, a hydroxyl group, or a halogen atom;
$R^4$ represents a hydrogen atom or a lower alkyloxy group;
$R^5$ represents a lower alkyloxy group, a halogen atom, a hydroxyl group, or a methylenedioxy group formed together with $R^6$ or an isopropylidenedioxy group formed together with $R^6$;
$R^6$ represents a lower alkyloxy group, a methylenedioxy group formed together with $R^5$ or an isopropylidenedioxy group formed together with $R^5$;
$R^7$ represents a hydrogen atom or a lower alkyl group; and
$R^8$ represents a hydrogen atom, a hydroxyl group, an amino group, a lower alkylcarbonyloxy group, or a halogen atom.

2. The compound or salt of claim 1, wherein $R^1$ represents a hydrogen atom, an alkyl group with a carbon number of 1 to 6, a hydroxyl group, an alkyloxy group with a carbon number of 1 to 6, or a halogen atom;
$R^2$ represents a hydrogen atom, an alkyl group with a carbon number of 1 to 6, a halogen atom, an alkylcarbonyloxy group with a carbon number of 1 to 6 optionally having a substituent, a heterocyclic carbonyloxy group, an alkyloxycarbonyloxy group with a carbon number of 1 to 6, an alkyl-substituted aminocarbonyloxy group with a carbon number of 1 to 6, an amino group optionally having a substituent, an alkyl-substituted amino group with a carbon number of 1 to 6 optionally having a substituent, an alkyl-substituted amino group with a carbon number of 1 to 6 optionally having an aromatic group, a heterocyclic group, an alkyloxycarbonylamino group with a carbon number of 1 to 6 optionally having a substituent, an alkyloxycarbonylamino group with a carbon number of 1 to 6 optionally having an aromatic group, an alkylcarbonylamino group with a carbon number of 1 to 6, a formamide group, or a hydroxyalkyl group with a carbon number of 1 to 6;

$R^3$ represents a hydrogen atom, an alkyl group with a carbon number of 1 to 6, a hydroxyl group, or a halogen atom;

$R^4$ represents a hydrogen atom or an alkyloxy group with a carbon number of 1 to 6;

$R^5$ represents an alkyloxy group with a carbon number of 1 to 6, a halogen atom, a hydroxyl group, or a methylenedioxy group formed together with $R^6$ or an isopropylidenedioxy group formed together with $R^6$;

$R^6$ represents an alkyloxy group with a carbon number of 1 to 6, or a methylenedioxy group formed together with $R^5$ or an isopropylidenedioxy group formed by together with $R^5$;

$R^7$ represents a hydrogen atom or an alkyl group with a carbon number of 1 to 6; and $R^8$ represents a hydrogen atom, a hydroxyl group, an amino group, an alkylcarbonyloxy group with a carbon number of 1 to 6, or a halogen atom.

3. The compound or salt of claim 1, wherein $R^1$ represents a hydrogen atom, a methyl group, a hydroxyl group, a methoxy group, a chlorine atom, or a fluorine atom;

$R^2$ represents a hydrogen atom, an ethyl group, a fluorine atom, an acetoxy group, a propionyloxy group, an isobutyryloxy group, a valeroyloxy group, a 3-methoxycarbonylpropionyloxy group, a pivaloyloxy group, a butyryloxy group, a 6-carbo[(12aS,13S)-13-hydroxy-6,7-dimethoxy-9,10,11,12,12a,13-hexahydro-9a-aza-cyclopenta[b]triphenylene-3-yloxy]heptanoyloxy group, a nicotinoyloxy group, an isonicotinoyloxy group, a piperidinopiperidinylcarbonyloxy group, a 2-thiophenecarbonyloxy group, a 3-thiophenecarbonyloxy group, a 2-furoyloxy group, a 3-furoyloxy group, a methoxycarbonyloxy group, a 2-propynyloxycarbonyloxy group, an ethoxycarbonyloxy group, a dimethylaminocarbonyloxy group, an amino group, a methanesulfonamide group, a diphenylmethylamino group, an ethylamino group, a pyrrolidinyl group, an isobutyloxycarbonylamino group, a benzyloxycarbonylamino group, a methoxycarbonylamino group, an acetamide group, a trifluoroacetamide group, a benzamide group, a formamide group, or a hydroxymethyl group;

$R^3$ represents a hydrogen atom, a methyl group, a hydroxyl group, a fluorine atom, or a chlorine atom;

$R^4$ represents a hydrogen atom or a methoxy group;

$R^5$ represents a methoxy group, an ethoxy group, a fluorine atom, a hydroxyl group, or a methylenedioxy group formed together with $R^6$ or an isopropylidenedioxy group formed together with $R^6$;

$R^6$ represents a methoxy group, an ethoxy group, or a methylenedioxy group formed together with $R^5$ or an isopropylidenedioxy group formed together with $R^5$;

$R^7$ represents a hydrogen atom or a methyl group; and $R^8$ represents a hydrogen atom, a hydroxyl group, an amino group, an acetoxy group, or a fluorine atom.

4. The compound or salt of claim 1, wherein the compound represented by the formula (1) has a conformation represented by formula (2):

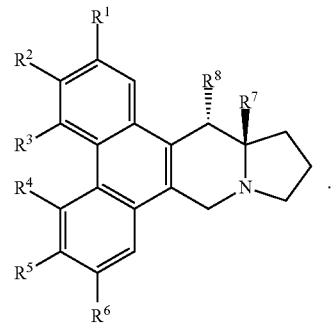

(2)

5. The compound or salt of claim 1, wherein the compound represented by formula (1) is a compound represented by formula (3):

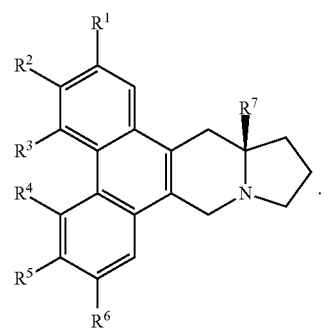

(3)

6. A compound or a salt thereof selected from the group consisting of:
(12aS,13S)-6,7-dimethoxy-9,10,11,12,12a,13-hexahydro-9a-aza-cyclopenta[b]triphenylene-13-ol;
(12aR,13R)-6,7-dimethoxy-9,10,11,12,12a,13-hexahydro-9a-aza-cyclopenta[b]triphenylene-13-ol;
(12aS,13S)-3-ethyl-6,7-dimethoxy-9,10,11,12,12a,13-hexahydro-9a-aza-cyclopenta[b]triphenylene-13-ol;
(12aR,13R)-3-ethyl-6,7-dimethoxy-9,10,11,12,12a,13-hexahydro-9a-aza-cyclopenta[b]triphenylene-13-ol;
(12aS,13S)-3-fluoro-6,7-dimethoxy-9,10,11,12,12a,13-hexahydro-9a-aza-cyclopenta[b]triphenylene-13-ol;
(12aR,13R)-3-fluoro-6,7-dimethoxy-9,10,11,12,12a,13-hexahydro-9a-aza-cyclopenta[b]triphenylene-13-ol;
acetic acid(12aS,13S)-13-hydroxy-6,7-dimethoxy-9,10,11,12,12a,13-hexahydro-9a-aza-cyclopenta[b]triphenylene-3-yl ester;
acetic acid(12aS,13S)-3-acetoxy-6,7-dimethoxy-9,10,11,12,12a,13-hexahydro-9a-aza-cyclopenta[b]triphenylene-13-yl ester;
isobutyric acid(12aS,13S)-13-hydroxy-6,7-dimethoxy-9,10,11,12,12a,13-hexahydro-9a-aza-cyclopenta[b]triphenylene-3-yl ester;
2,2-dimethyl-propionic acid(12aS,13S)-13-hydroxy-6,7-dimethoxy-9,10,11,12,12a,13-hexahydro-9a-aza-cyclopenta[b]triphenylene-3-yl ester;
nicotinic acid(12aS,13S)-13-hydroxy-6,7-dimethoxy-9,10,11,12,12a,13-hexahydro-9a-aza-cyclopenta[b]triphenylene-3-yl ester;
isonicotinic acid(12aS,13S)-13-hydroxy-6,7-dimethoxy-9,10,11,12,12a,13-hexahydro-9a-aza-cyclopenta[b]triphenylene-3-yl ester;

1,4]bipiperidinyl-1'-carboxylic acid(12aS,13S)-13-hydroxy-6,7-dimethoxy-9,10,11,12,12a,13-hexahydro-9a-aza-cyclopenta[b]triphenylene-3-yl ester;

acetic acid(S)-13-fluoro-6,7-dimethoxy-9,10,11,12,12a,13-hexahydro-9a-aza-cyclopenta[b]triphenylene-3-yl ester;

propionic acid(12aS,13S)-13-hydroxy-6,7-dimethoxy-9,10,11,12,12a,13-hexahydro-9a-aza-cyclopenta[b]triphenylene-3-yl ester;

succinic acid(12aS,13S)-13-hydroxy-6,7-dimethoxy-9,10,11,12,12a,13-hexahydro-9a-aza-cyclopenta[b]triphenylene-3-yl ester methyl ester;

carbonic acid(12aS,13S)-13-hydroxy-6,7-dimethoxy-9,10,11,12,12a,13-hexahydro-9a-aza-cyclopenta[b]triphenylene-3-yl ester methyl ester;

((12aS,13S)-13-hydroxy-6,7-dimethoxy-9,10,11,12,12a,13-hexahydro-9a-aza-cyclopenta[b]triphenylene-3-yl)-carbamic acid isobutyl ester;

thiophene-2-carboxylic acid(12aS,13S)-13-hydroxy-6,7-dimethoxy-9,10,11,12,12a,13-hexahydro-9a-aza-cyclopenta[b]triphenylene-3-yl ester;

furan-2-carboxylic acid(12aS,13S)-13-hydroxy-6,7-dimethoxy-9,10,11,12,12a,13-hexahydro-9a-aza-cyclopenta[b]triphenylene-3-yl ester;

dimethyl-carbamic acid(12aS,13S)-13-hydroxy-6,7-dimethoxy-9,10,11,12,12a,13-hexahydro-9a-aza-cyclopenta[b]triphenylene-3-yl ester;

furan-3-carboxylic acid(12aS,13S)-13-hydroxy-6,7-dimethoxy-9,10,11,12,12a,13-hexahydro-9a-aza-cyclopenta[b]triphenylene-3-yl ester;

thiophene-3-carboxylic acid(12aS,13S)-13-hydroxy-6,7-dimethoxy- 9,10,11,12,12a,13-hexahydro-9a-aza-cyclopenta[b]triphenylene-3-yl ester;

octanedionic acid(9S,12S)-13-hydroxy-6,7-dimethoxy-9,10,11,12,12a,13-hexahydro-9a-aza-cyclopenta[b]triphenylene-3-yl ester(12aS,13S)-13-hydroxy-6,7-dimethoxy-9,10,11,12,12a,13-hexahydro-9a-aza-cyclopenta[b]triphenylene-3-yl ester;

(12aS,13S)-3-amino-6,7-dimethoxy-9,10,11,12,12a,13-hexahydro-9a-aza-cyclopenta[b]triphenylene-13-ol;

((12aS,13S)-13-hydroxy-6,7-dimethoxy-9,10,11,12,12a,13-hexahydro-9a-aza-cyclopenta[b]triphenylene-3-yl)-carbamic acid benzyl ester;

carbonic acid(12aS,13S)-13-hydroxy-6,7-dimethoxy-9,10,11,12,12a,13-hexahydro-9a-aza-cyclopenta[b]triphenylene-3-yl ester-propyn-2-yl ester;

carbonic acid ethyl ester(12aS,13S)-13-hydroxy-6,7-dimethoxy-9,10,11,12,12a,13-hexahydro-9a-aza-cyclopenta[b]triphenylene-3-yl ester;

(12aS,13S)-6,7-dimethoxy-9,10,11,12,12a,13-hexahydro-9a-aza-cyclopenta[b]triphenylene-2,13-diol;

(12aS,13S)-6,7-dimethoxy-9,10,11,12,12a,13-hexahydro-9a-aza-cyclopenta[b]triphenylene-4,13-diol;

(S)-3-fluoro-6,7-dimethoxy-9,10,11,12,12a,13-hexahydro-9a-aza-cyclopenta[b]triphenylene;

(S)-6,7-dimethoxy-9,10,11,12,12a,13-hexahydro-9a-aza-cyclopenta[b]triphenylene;

(S)-6,7-dimethoxy-9,10,11,12,12a,13-hexahydro-9a-aza-cyclopenta[b]triphenylene-2-ol;

acetic acid(S)-6,7-dimethoxy-9,10,11,12,12a,13-hexahydro-9a-aza-cyclopenta[b]triphenylene-3-yl ester;

2,2-dimethyl-propionic acid(S)-6,7-dimethoxy-9,10,11,12,12a,13-hexahydro-9a-aza-cyclopenta[b]triphenylene-3-yl ester;

succinic acid(S)-6,7-dimethoxy-9,10,11,12,12a,13-hexahydro-9a-aza-cyclopenta[b]triphenylene-3-yl ester methyl ester;

carbonic acid(S)-6,7-dimethoxy-9,10,11,12,12a,13-hexahydro-9a-aza-cyclopenta[b]triphenylene-3-yl ester methyl ester;

furan-2-carboxylic acid(S)-6,7-dimethoxy-9,10,11,12,12a,13-hexahydro-9a-aza-cyclopenta[b]triphenylene-3-yl ester;

nicotinic acid(S)-6,7-dimethoxy-9,10,11,12,12a,13-hexahydro-9a-aza-cyclopenta[b]triphenylene-3-yl ester;

(S)-6,7-dimethoxy-9,10,11,12,12a,13-hexahydro-9a-aza-cyclopenta[b]triphenylene-4-ol;

(S)-3-ethyl-6,7-dimethoxy-9,10,11,12,12a,13-hexahydro-9a-aza-cyclopenta[b]triphenylene;

((S)-6,7-dimethoxy-9,10,11,12,12a,13-hexahydro-9a-aza-cyclopenta[b]triphenylene-3-yl)-carbamic acid isobutyl ester;

pentanoic acid(S)-6,7-dimethoxy-9,10,11,12,12a,13-hexahydro-9a-aza-cyclopenta[b]triphenylene-3-yl ester;

butyric acid(S)-6,7-dimethoxy-9,10,11,12,12a,13-hexahydro-9a-aza-cyclopenta[b]triphenylene-3-yl ester;

propionic acid(S)-6,7-dimethoxy-9,10,11,12,12a,13-hexahydro-9a-aza-cyclopenta[b]triphenylene-3-yl ester;

(S)-3-amino-6,7-dimethoxy-9,10,11,12,12a,13-hexahydro-9a-aza-cyclopenta[b]triphenylene;

N-((S)-6,7-dimethoxy-9,10,11,12,12a,13-hexahydro-9a-aza-cyclopenta[b]triphenylene-3-yl)-acetamide;

(S)-6,7-dimethoxy-3-pyrrolidine-9,10,11,12,12a,13-hexahydro-9a-aza-cyclopenta[b]triphenylene;

benzhydryl-((S)-6,7-dimethoxy-3 -pyrrolidine-9,10,11,12,12a,13-hexahydro-9a-aza-cyclopenta[b]triphenylene-3-yl)-amine;

((S)-6,7-dimethoxy-9,10,11,12,12a,13-hexahydro-9a-aza-cyclopenta[b]triphenylene-3-yl)-methanol;

N-((S)-6,7-dimethoxy-9,10,11,12,12a,13-hexahydro-9a-aza-cyclopenta[b]triphenylene-3-yl)-2,2,2-trifluoro-acetamide;

((S)-6,7-dimethoxy-9,10,11,12,12a,13-hexahydro-9a-aza-cyclopenta[b]triphenylene-3-yl)-ethylamine;

((S)-6,7-dimethoxy-9,10,11,12,12a,13-hexahydro-9a-aza-cyclopenta[b]triphenylene-3-yl)-carbamic acid methyl ester;

N-((S)-6,7-dimethoxy-9,10,11,12,12a,13-hexahydro-9a-aza-cyclopenta[b]triphenylene-3-yl)-methanesulfonamide;

N-((S)-6,7-dimethoxy-9,10,11,12,12a,13-hexahydro-9a-aza-cyclopenta[b]triphenylene-3-yl)-formamide; and N-((S)-6,7-dimethoxy-9,10,11,12,12a,13-hexahydro-9a-aza-cyclopenta[b]triphenylene-3-yl)-benzamide.

7. A medicine, comprising the compound or salt of claim 1 as an active ingredient.

8. An NFκB inhibitor, comprising the compound or salt of claim 1 as an active ingredient.

9. A therapeutic agent, comprising the compound or salt of claim 1 as an active ingredient, wherein the agent is suitable to treat colon cancer.

10. An agent for treating lung cancer, comprising the compound or salt of claim 1 as an active ingredient.

11. A pharmaceutical composition, comprising:
the compound or salt of claim 1; and
a pharmaceutically acceptable carrier.

12. A method for treating colon cancer in a subject in need thereof, comprising administering to said subject in need thereof, an effective amount of the compound or salt of claim 1.

13. A method for treating lung cancer in a subject in need thereof, comprising administering to said subject in need thereof, an effective amount of the compound or salt of claim 1.

14. A medicine, comprising the compound or salt of claim 6 as an active ingredient.

15. An NFκB inhibitor, comprising the compound or salt of claim 6 as an active ingredient.

16. A therapeutic agent, comprising the compound or salt of claim 6 as an active ingredient, wherein the agent is suitable to treat colon cancer.

17. An agent for treating lung cancer, comprising the compound or salt of claim 6 as an active ingredient.

18. A pharmaceutical composition, comprising:
compound or salt of claim 6; and
a pharmaceutically acceptable carrier.

19. A method for treating colon cancer in a subject in need thereof, comprising administering to said subject in need thereof, an effective amount of the compound or salt of claim 6.

20. A method for treating lung cancer in a subject in need thereof, comprising administering to said subject in need thereof, an effective amount of the compound or salt of claim 6.

* * * * *